United States Patent [19]

Bell

[11] Patent Number: 5,283,333

[45] Date of Patent: *Feb. 1, 1994

[54] CYCLIC COMPOUNDS FOR FORMING COMPLEXES WITH UREA, GUANIDINE AND AMIDINE DERIVATIVES

[75] Inventor: Thomas W. Bell, Stony Book, N.Y.

[73] Assignee: The Research Foundation of State University of New York, Albany, N.Y.

[*] Notice: The portion of the term of this patent subsequent to Jul. 9, 2008 has been disclaimed.

[21] Appl. No.: 705,733

[22] Filed: May 28, 1991

Related U.S. Application Data

[63] Continuation-in-part of Ser. No. 360,383, Jun. 2, 1989, Pat. No. 5,030,728, which is a continuation-in-part of Ser. No. 215,211, Jul. 5, 1988, abandoned.

[51] Int. Cl.$^5$ ............... C07D 471/00; C07D 491/00
[52] U.S. Cl. ............................ 546/27; 546/26; 546/32
[58] Field of Search ....................... 546/26, 32, 27

[56] References Cited

PUBLICATIONS

Thummel et al., Inorg. Chemical, 25, 1675–1679 (1986).
Thummel et al., J. Organic Chemical, 50, 2407–2412 (1985).
Bell et al., J. American Chemical Society, 108, 8109–8111 (1986).
Kelly et al., J. American Chemical Society, 109, 6549–6551 (1987).
Aarts et al., J. American Chemical Society, 108, 5035–5036 (1986).
Bell et al. Tetrahedron Lett., 28, 4817–4820 (1987).
Bell et al., J. American Chemical Society, 110, 3673–3674 (1988).
Bell et al., Third Chemical Congress of North America of the American Chemical Society, Jun. 5, 1988.
Bell et al., 196th American Chemical Society National Meeting, Sep. 18, 1988.
Bell, et al. 31st National Organic Symposium of the American Chemical Society, Jun. 18, 1989.
Bell, T. W., 72nd Canadian Chemical Conference and Exhibition of the Chemical Institute of Canada, Jun. 4, 1989.
Werner, et al., Simultaneous Determination Of Creatine, Uric Acid And Creatinine By High–Performance Liquid Chromatography With Direct Serum Injection And Multi–Wavelength Detection, Journal of Chromatography, 525 (1990) 265–275.
Hamilton, et al., Nucleotide Base Recognition: Synthesis Of Artificial Receptors Containing Two Distinct Binding Regions For The Complexation Of Bis-thymine Derivatives, J. Chem. Soc., Chem. Commun., (1990), 297–300.
Hamilton, et al., Nucleotide Base Recognition: Ditopic Binding Of Guanine To A Macrocyclic Receptor Containing Naphthyridine And Naphthalene Units, J. Chem. Soc., Chem. Commun.,(1988), 765–766.
Whitlock, et al., Concave Functionality: Design Criteria For Nonaqueous Binding Sites, J. Am. Chem. Soc.(1990), 112, 3910–3915.
Bell, et al., Torand Synthesis By Trimerization–New Receptors For Guanidinium, Angew. Chem. Int. Ed. Engl. 29 (1990) No. 8, 923–925.
Hunter, et al., The Nature of $\pi$—$\pi$ Interactions, J. Am. Chem. Soc. (1990), 112, 5525–5534.
Jeppesen, et al., Determination Of Creatinine In Undiluted Blood Serum By Enzymatic Flow Injection Analysis With Optosensing, Analytica Chimica Acta, 214, (1988) 147–159.
Bell, et al., Organic Synthesis, L. A. Paquette, Ed., vol. 69 (1990), pp. 226–237.

*Primary Examiner*—Cecilia Tsang
*Attorney, Agent, or Firm*—Hoffmann & Baron

[57] ABSTRACT

A chromophoric molecule capable of forming stable complexes with urea, guanidine or amidine compounds and the acid addition salts thereof which comprises a nucleous of heterocyclic rings.

36 Claims, No Drawings

CYCLIC COMPOUNDS FOR FORMING COMPLEXES WITH UREA, GUANIDINE AND AMIDINE DERIVATIVES

This invention was made with government support under Grant Number GM-32937 awarded by the National Institute of Health. The government has certain rights in the invention.

This application is a continuation in part of U.S. patent application Ser. No. 360,383, which was filed on Jun. 2, 1989, U.S. Pat. No. 5,030,728, which is a continuation-in-part of U.S. patent application Ser. No. 215,211, filed Jul. 5, 1980, now abandoned.

The biologically important compounds urea, guanidine, (shown below), their derivatives and their acid addition salts are present in human bodily fluids, such as serum and urine, where they serve as indications of various disorders. For example, the concentration of urea in blood serum, which is normally expressed as "blood urea nitrogen" (BUN), is used as an indication of renal dysfunction, such as uremia, and nitrogen metabolism; see, for example, (Wright, "Maintenance Hemodialysis", G. K. Hall: Boston (1981), Chpt. 1).

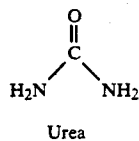
Urea

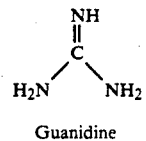
Guanidine

Guanidine and its derivatives, such as N-methylguanidine, guanidinoacetic acid, guanidinopropionic acid and guanidinosuccinic acid, are also found in bodily fluids. Assays for determining the concentration of guanidine and its derivatives in blood serum, urine and hemodialysate are useful in detecting certain metabolic disorders such as hyperargininemia and argininosuccinic aciduria; (Kobayashi, et al., Anal. Chem., 58, 1380-1383 (1986)). In the present specification, it will be understood that guanidine refers as well to guanidinium ion.

Amidine derivatives such as dibenzamidines are used as antiprotozoal drugs. Pentamidine isethionate is particularly useful in treating Pneumocystis pneumonia in AIDS patients. It is desirable to be able to assay amidine drugs in bodily fluids in order to optimize dosages. It will be understood in the present specification that amidine refers as well to amidinium ion.

Although it is generally desirable to be able selectively to bind urea, guanidine and amidine compounds and their salts in fluids such as bodily fluids, convenient methods are unavailable. In particular, complexing agents selective for these molecules are not known.

Monocyclic and polycyclic molecules such as crown ethers, cryptands, spherands and torands are known for selectively removing metal cations from solution (Bell, et al., *Journal of Inclusion Phenomena* 5 (1987), 149-152; Pedersen, *J. Am. Chem. Soc.* 1967, 89, 2495-2496; Dietrich et al., *Tetrahedron Lett.* 1969, 2885-2885; Cram et al., *J. Am. Chem. Soc.* 1979, 101, 6752-6754)). Complexing agents that are selective for organic molecules are, however, less readily available. Kelly, et al., has disclosed a complexing agent that is selective for uric acid. (J. Am. Chem. Soc., 109, 6549-6551 (1987)). Aarts et al. has disclosed a crown ether receptor that forms a complex with urea that is soluble in chloroform. (Aarts, et al., J. Am. Chem. Soc., 108, 5035-5036, (1986)). The stability of the urea complex disclosed by Aarts, et al., is insufficient, however, to provide the basis for medical diagnoses which require great selectivity and sensitivity.

Therefore, there is a need for complexing agents that selectively form strong complexes with urea, guanidine, amidines, their ions and derivatives. Urea, guanidine, amidine, their ions and derivatives are intended to include urea, thiourea, guanidine, guanidine monosubstituted on one nitrogen atom, guanidine disubstituted on one nitrogen atom, creatinine, arginine, and amidine compounds and addition salts thereof. The principal objective of the invention is to provide such complexing agents. Further objectives of the present invention are to provide methods for synthesizing such complexing agents in high yield and purity, and the complexes formed with such complexing agents. These and other objectives as will be apparent to those skilled in the art have been met by providing compounds that form stable complexes with urea, guanidine, and amidine compounds as well as their ions and derivatives. The compounds shown below have structures A-G, wherein:

C represents carbon atoms;
$C_1$ represents carbon atoms preferably bonded to acyclic oxygen, nitrogen or sulfur atoms;
A and G independently represent carbon, sulfur, nitrogen or oxygen atoms;
S independently represents carbon or nitrogen atoms;
D and T independently represent nitrogen, oxygen or sulfur atoms;
X independently represents $(A)_m$;
b independently represents 0-6;
d represents 0 or 1;
s independently represents 1-7, preferably 2-7;
$Z_1$ represents $(A)_p$;
$Z_2$ represents $(A)_q$;
m=0-5;
p and q=0-5 except p and q cannot both be 0;
wherein A, D, S, G or T atoms contain sufficient additional bonds to adjacent A, D, S, G or T atoms or to other atoms to lead to stable molecules; and
wherein an A, S and G atom that represents a sulfur, nitrogen or oxygen atom will not be adjacent to an A, D, S, G or T atom that also represents a sulfur, nitrogen or oxygen atom;

In compounds A-G:
A preferably represents carbon or nitrogen and more preferably carbon;
G preferably represents $sp^2$ hybridized nitrogen, oxygen or sulfur, and more preferably $sp^2$ hybridized nitrogen;
S preferably represents carbon;
D preferably represents $sp^2$ hybridized nitrogen;
T preferably represents oxygen or nitrogen;
$C_1$ preferably represents carbon bonded to acyclic oxygen.
b preferably represents 1-3;
d preferably represents 1;
m preferably represents 0-2;
s preferably represents 2-4;
p and q, independently, preferably represent 0-2.

In a more preferred embodiment of compounds A-G:
A represents carbon;
G represents $sp^2$ hybridized nitrogen;
S represents carbon
D represents $sp^2$ hybridized nitrogen;
T represents $sp^2$ hybridized oxygen $C_1$ is doubly bonded to acyclic oxygen b represents 2 m represents 1 d represents 1 s represents 3 p and q independently represent 1.

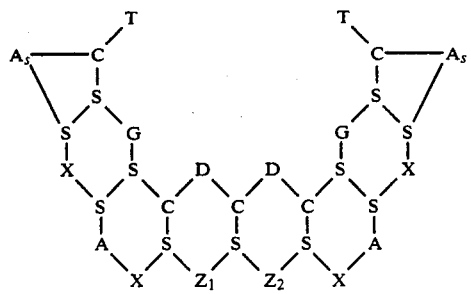

A

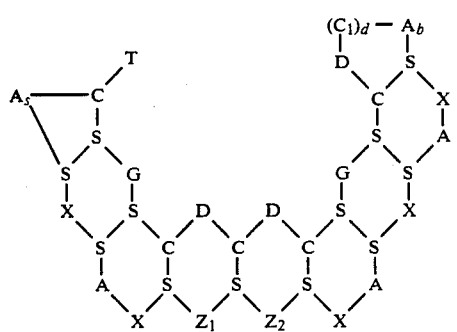

B

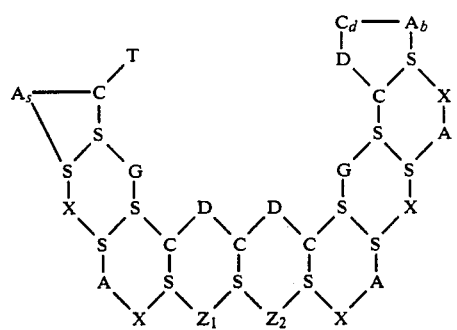

C

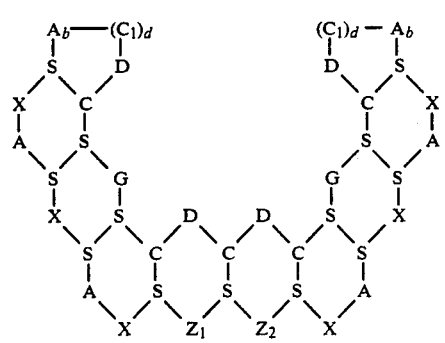

D

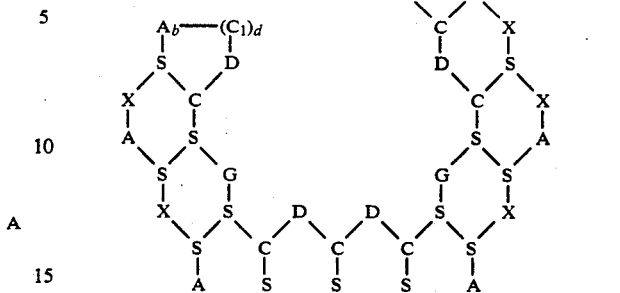

E

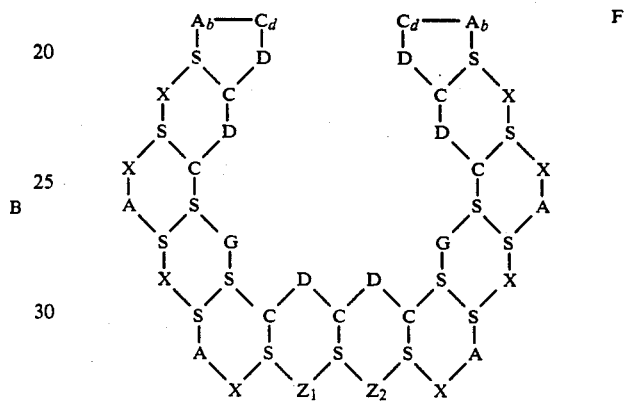

F

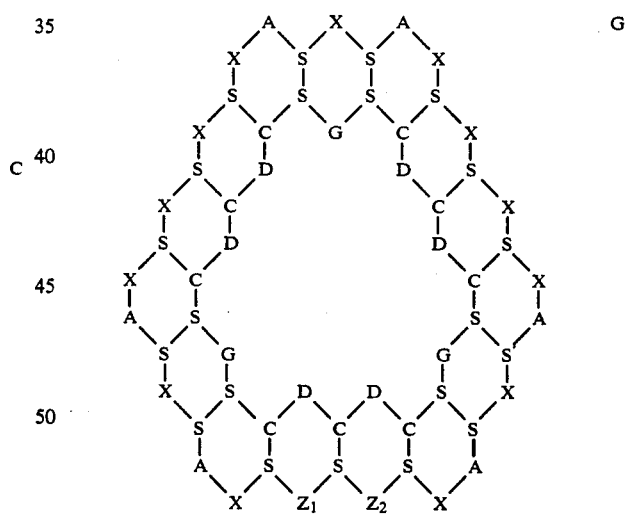

G

The structures shown above as A–G comprise the nucleus of atoms of the complexing agents of the present invention. Each atom indicated in the structure possesses a sufficient number of bonds either to adjacent atoms or to other atoms not shown in order to form stable compounds. Stable compounds are those with appreciable lifetimes at room temperature, preferably lifetimes more than one month and more preferably more than one year. The critical aspect of the claimed molecules is that they have D or T atoms in the positions shown. The basic molecules of the invention consist of the atoms shown in FIGS. A–G and as many additional hydrogen or other atoms to render the molecule stable. Any other atoms are possible, although they usually are carbon, oxygen, nitrogen, sulfur, phosphorus, fluorine, chlorine, bromine or iodine. These additional atoms may constitute any organic or inorganic moiety. Some suitable inorganic moieties include, for example, halo, a nitrogen oxide such as nitro, a sulfur oxide such as $SO_3H$, amino and the like.

Suitable organic moieties include, for example, alkyl, aryl, alkylaryl, arylalkyl, alkoxy, alkylthio and substituted amino. The alkyl groups may be branched or unbranched, cyclic or acyclic, and are preferably from 1–30 carbon atoms, preferably 2–20 carbon atoms, and more preferably 3–6 carbon atoms. The alkyl group may be fully saturated or may contain one or more multiple bonds. The carbon atoms of the alkyl group may be continuous or may be separated by one or more functional groups, such as an oxygen atom, a sulfur atom, a keto group, an amino group, an amido group, an oxycarbonyl group, and the like. The alkyl group may also be substituted with one or more aryl groups as disclosed below. Cyclic organic moieties may be aromatic or non-aromatic and may be fused to other rings, such as to any of the rings shown in structures A–G.

The aryl group may, for example, be a phenyl group, which may be unsubstituted or substituted with any of the inorganic or organic groups discussed above. The aryl group may also be a heteroaryl group, containing one or more ring oxygen, nitrogen or sulfur atom; be five, six or seven membered; and be fused to other saturated or unsaturated rings.

The amino group may be substituted by, for example, any alkyl or aryl group discussed above.

In general, substituents added to compounds A–G are useful in modifying the solubility properties of the complexing agents. For example, non-polar groups such as alkyl groups enhance the solubility of the compounds in non-polar solvents. Alternatively, polar substituents enhance the solubility of the molecules in polar solvents. Some suitable examples of non-polar substituents include, for example, $C_1$–$C_{10}$, preferably $C_2$–$C_8$, and more preferably $C_3$–$C_6$ alkyl such as methyl, ethyl, propyl, isopropyl, n-butyl, s-butyl, isobutyl, t-butyl, n-pentyl, n-hexyl and cyclohexyl. Some suitable examples of polar groups include, for example, hydroxyl, amino-$CO_2H$ and —$SO_3H$.

The substituents may occur anywhere on compounds A–G. Preferably, they do not occur on atoms forming the cavity of the molecules, where they might interfere with the guest urea, guanidine or amidine molecules in complexes of A–G and such guest molecules.

Some specific examples of molecules encompassed by formulas A–G are shown below as compounds IV, V, VI, VII, VIII, VIIIb, IX, IXb, IXc, IXe, X, XI, XII and XIII. These molecules form strong complexes with urea and guanidine compounds. Some structures of complexes formed between compounds IV–XIII as listed above and ligands such as urea, guanidine, amidines, their acid addition salts and the derivatives thereof are shown as complexes IVa, IVb, Va, VIa, VIIa, VIIIa, VIIIc, IXa, and IXd.

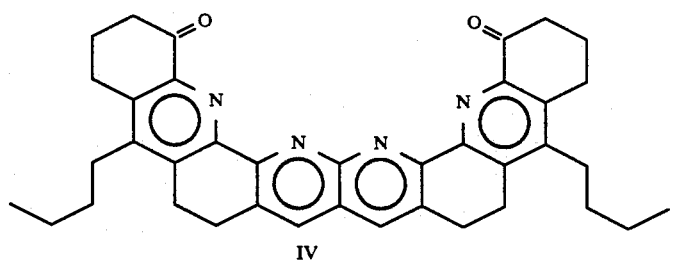

IV

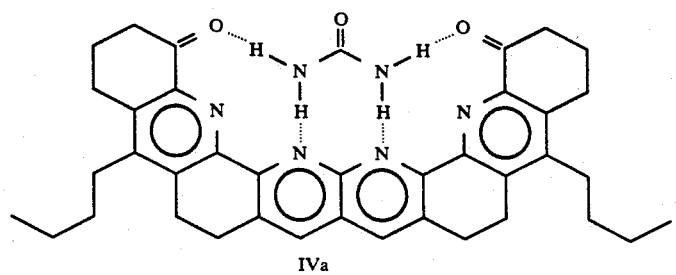

IVa

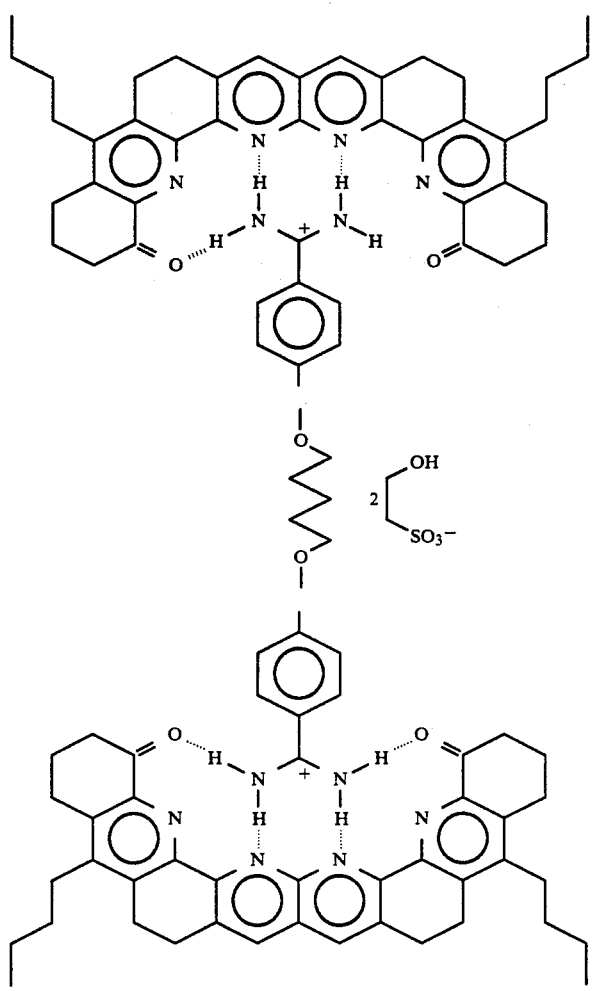
IVb
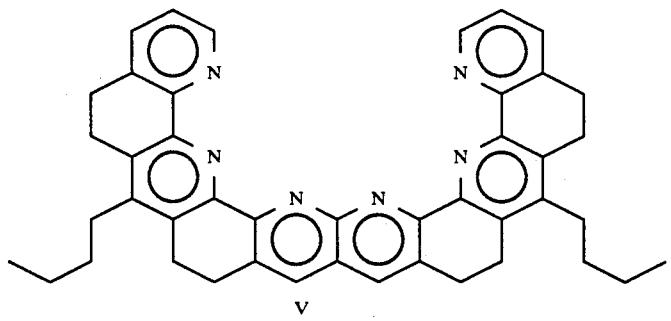
V
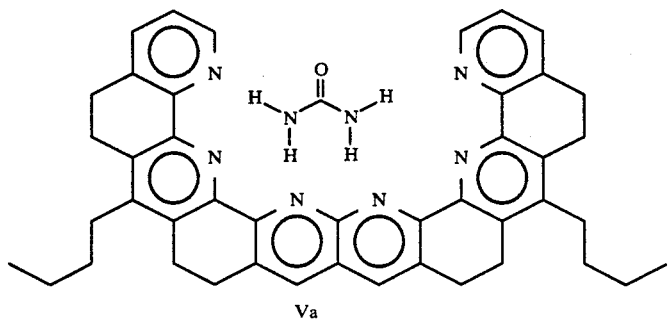
Va

-continued
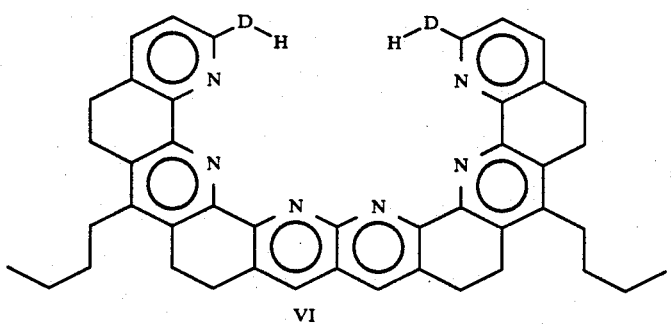
VI
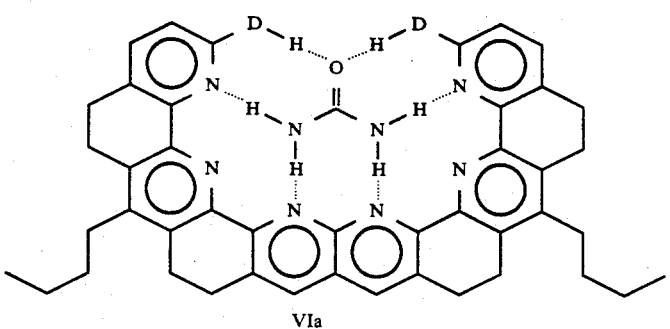
VIa
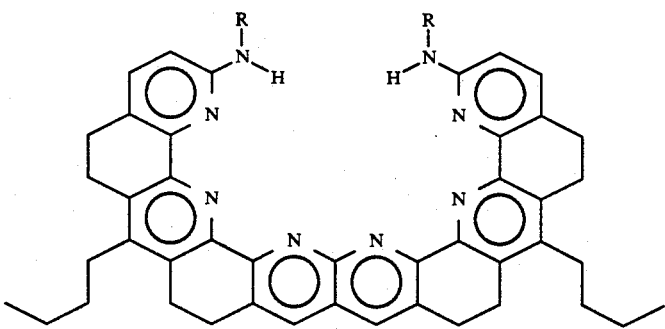
VII R = H
VIII R = COCH₃
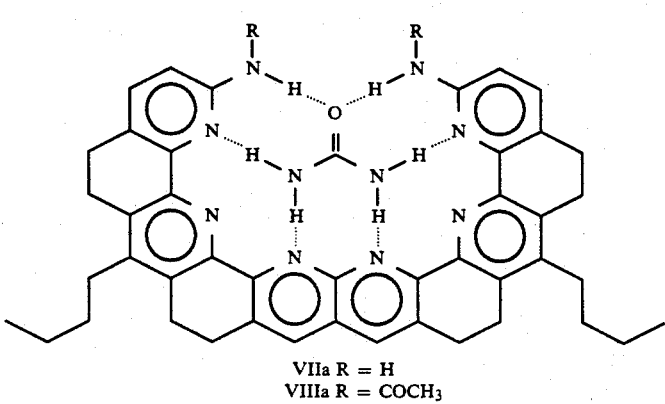
VIIa R = H
VIIIa R = COCH₃

-continued
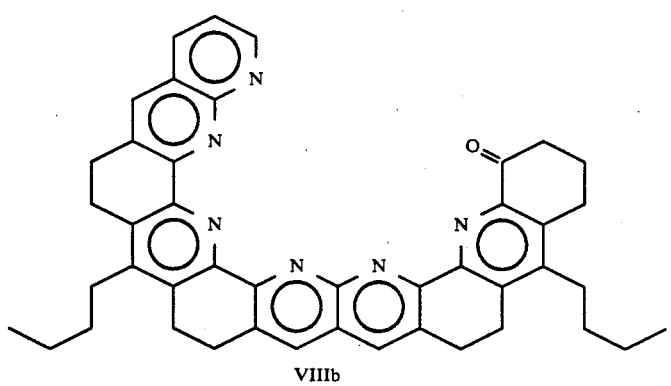
VIIIb
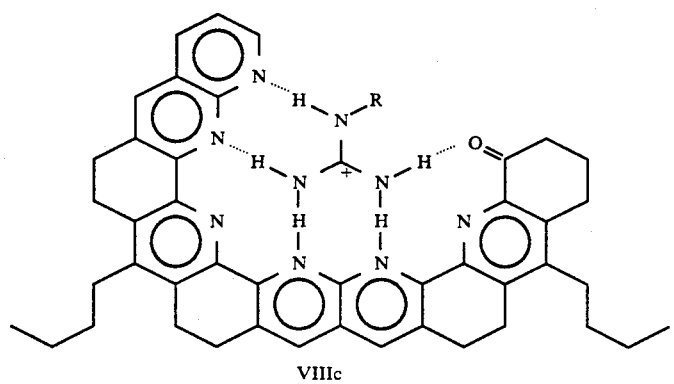
VIIIc
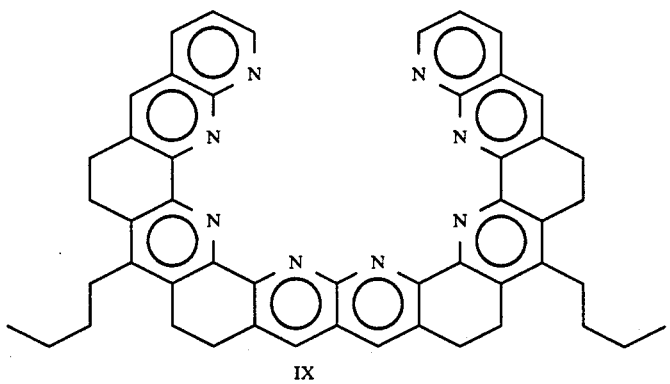
IX
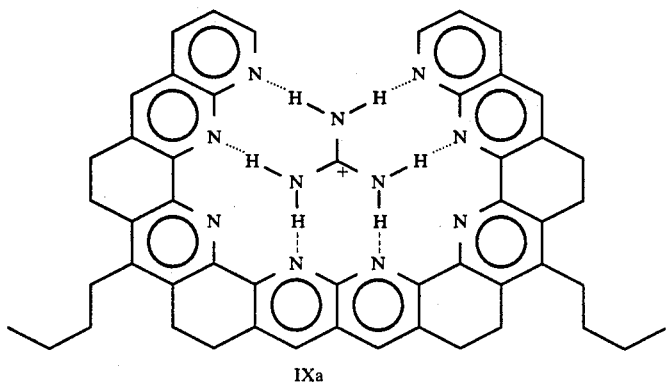
IXa

-continued
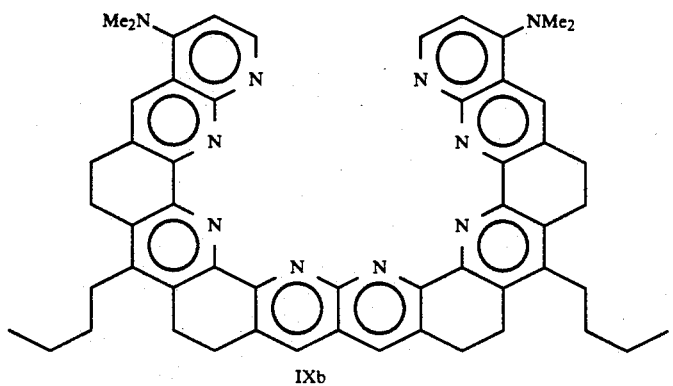
IXb
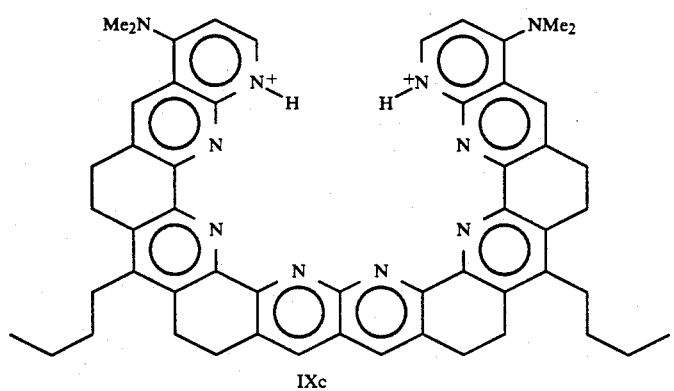
IXc
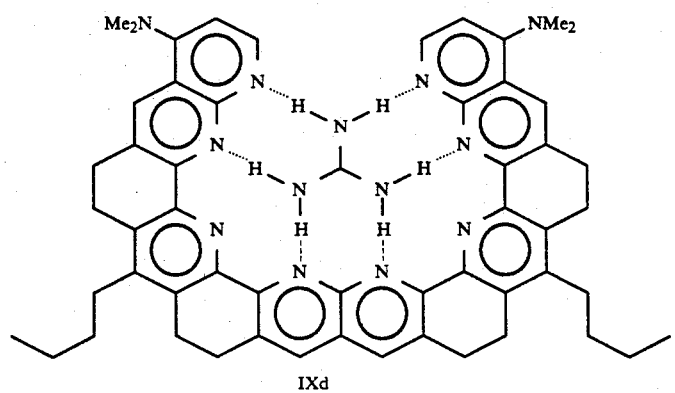
IXd

-continued
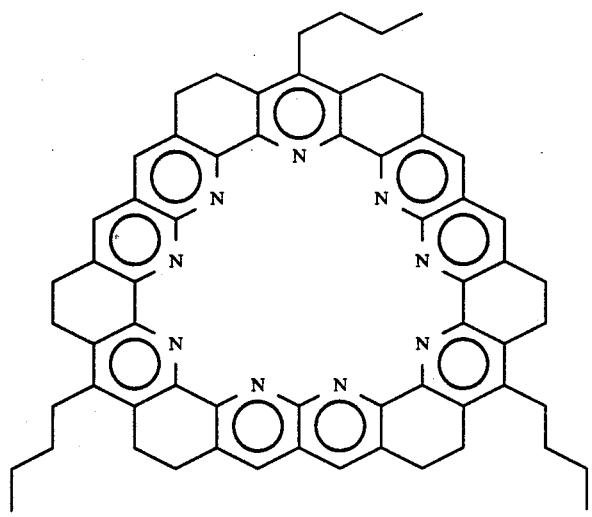
IXe
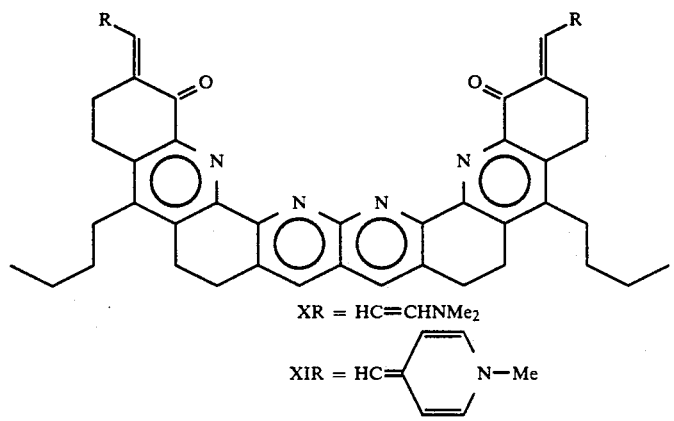
X R = HC=CHNMe₂
XI R = HC=$\begin{smallmatrix}\text{pyridine}\\\text{N—Me}\end{smallmatrix}$
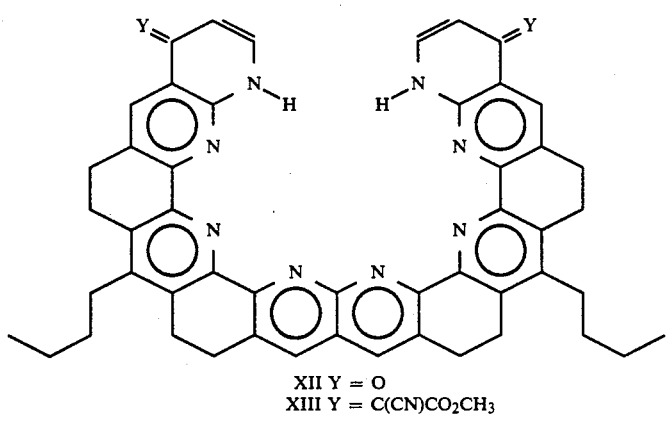
XII Y = O
XIII Y = C(CN)CO₂CH₃
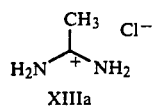
XIIIa
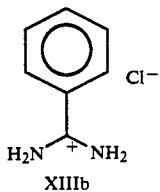
XIIIb

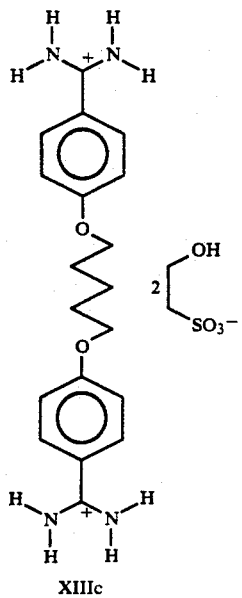

XIIIc

-continued

In such complexes, urea may be thiourea. The urea, guanidine and amidine compounds may be in the form of ions, such as those in their acid addition salts. The acid addition salt may be formed by treating urea, guanidine and amidine with any acid, such as HCl, HBr, $HNO_3$, $H_2SO_4$, p-toluenesulfonic acid, acetic acid, or benzoic acid.

All of the structures shown above as IV-XIII have at least two n-butyl groups attached to pyridine rings. These butyl groups could be replaced by hydrogen atoms or by any other substituent as discussed above. Moreover, either of the n-butyl substituents or their replacement could be moved to any other position on the ring except for the nitrogen atoms that form hydrogen bonds with a hydrogen atom of the urea, guanidine or amidine molecule as shown in complexes IVa-IXd. These nitrogen atoms correspond to D and T in structures A-G.

The butyl groups at the positions shown in structures IV-IX are convenient for inducing solubility in non-polar solvents such as chloroform. As discussed below, such molecules are easily synthesized.

Compounds IV and V are typical examples of compounds of the present invention. They bind both urea, guanidine and amidine compounds and are especially suitable for binding guanidine that is disubstituted on one nitrogen atom or urea. Compounds IV and V are specific examples of structures A and D, respectively.

Compound VI adds a group having a D—H (i.e. N—H, O—H or S—H) bond to the structure of compound V at a position that allows the added hydrogen atom to form a hydrogen bond with the oxygen atom of urea as shown in complex VIa or with the corresponding nitrogen atom of a guanidine compound. Compounds VII and VIII are examples of compound VI wherein the D—H group is an amino or amido group. The R groups in VII and VIII and anywhere else in the specification may be any of the substituents discussed above in regard to substituents on the rings in structures A-G.

Compound VIIIb is similar to compound IV except that a naphthyridine ring system has been fused to one of the terminal cyclohexanone rings. This compound is a specific example of a molecule encompassed by structure C. Compound VIIIb is especially well suited to form complexes with mono-substituted guanidine compounds, such as arginine, guanidinoacetic acid, guanidinopropionic acid, guanidinosuccinic acid, methyl guanidine, and the like, as shown in complex VIIIc. These complexes have five hydrogen bonds, and are very stable.

Compound IX is similar to compound VIIIb, except that both terminal cyclohexanone rings of IV have been converted to naphthyridine rings. This structure is a specific example of structure F. Compound IX is especially suited to form complexes with guanidine as shown in structure IXa.

Compound IXb is similar to compound IX except for the addition to the terminal naphthyridine ring of a dialkylamino group para to the ring nitrogen atom on both sides of the molecule. The ring nitrogen atoms of the terminal rings are so basic in these molecules that it is protonated in neutral aqueous solution as shown in IXc. The protons are well suited to form hydrogen bonds with the oxygen of urea as shown in compound IXd. As shown in compound IXd, compound IXc is capable of forming six hydrogen bonds with urea.

Compound IXe is a specific example of structure G. Guanidine and guanidinium ion are especially stably complexed by compound IXe.

The compounds of the present invention may be used to dissolve urea, guanidine and amidine compounds in solvents in which they are otherwise insoluble. For example, urea, guanidine and amidine compounds and their acid addition salts may be dissolved in chloroform containing compounds encompassed by host compounds A-G. This selective complexing ability of compounds A-G can be used to separate urea, guanidine and amidine compounds and their acid addition salts from other water soluble compounds by contacting a solid mixture or aqueous solution containing urea, guanidine, or amidine compounds or their salts with chloroform containing a receptor molecule according to structures A-G. When D in structures A-G represents $sp^2$ or $sp^3$ hybridized nitrogen, the urea, guanidine or amidine compounds may be extracted from the chloroform solution by washing the chloroform solution with aqueous acid. This method provides a convenient way to purify urea, guanidine and amidine compounds. If receptor molecules A-G contain an alkyl substituent such as butyl, the receptor molecule remains in the chloroform.

In addition, urea, guanidine and amidine compounds and their salts may be extracted from fluids such as bodily fluids. The removal of urea from blood is desirable to correct renal dysfunction, for example, in dialysis. For this purpose, it is convenient to immobilize receptors A-G. Immobilization can be accomplished by binding the receptors to a polymer, such as those used in protein synthesis. For example, polystyrene can be prepared with electrophilic groups such as chloromethyl. If the receptors contain a nucleophilic group, such as amino or hydroxy, they can be bound to the polymer.

It may also be desirable to bind urea, guanidine and amidine compounds and their salts for the purpose of conducting diagnostic assays. As mentioned above, abnormal concentrations of urea and guanidinium compounds in the blood or urine of a patient may indicate certain renal disfunctions. Since the amino acid arginine has a guanidinium group, it can be selectively complexed in the presence of other amino acids.

In addition to the above utilities, the compounds of the invention selectively form complexes with amidines, such as acetamidine, benzamidine and their acid addition salts, i.e. X111a and X111b, respectively. Dibenzamidines are particularly important compounds, since they are antiprotozoal agents. Pentamidine isethionate (XIIIc) is a particularly important dibenzamidine, since it is effective in treating Pneumocystis carinii pneumonia in AIDS patients. It is desirable to monitor the level of pentamidine isethionate in patients in order to minimize side effects. Pentamidines may be assayed by first removing them from body fluids, such as from blood, through complexation with compounds of the invention and extraction of the complexes into organic solvents, such as chloroform. Compounds IV and V form especially stable complexes with dibenzamidines. Such a complex between compound IV and pentamidine isethionate is shown in structure IVb.

Methods for determining the concentration of complexes formed by the compounds of the present invention include spectroscopic methods such as, for example, NMR spectroscopy, UV-visible spectroscopy, and fluorescence spectroscopy. For this purpose, it is desirable to have chromophoric substituents that can be detected by UV-visible and fluorescence spectroscopy wherein the electrons of the chromophoric group are conjugated with the electrons of an atom that forms a hydrogen bond to urea or guanidine. Examples of such molecules are shown as compounds X-XIII.

The chromophoric compounds of the present invention bind urea, guanidine and amidine compounds very strongly. When they do, the wavelengths of radiation absorbed by the chromophores shift as a result of the conjugation between the chromophores and the atoms forming hydrogen bonds. This shift may be used as the basis of a spectroscopic determination of the concentration of the complex by standard analytical techniques.

In compounds X-XIII, the following chromophoric groups are shown:

—(HC=CH)$_{1-4}$NMe$_2$

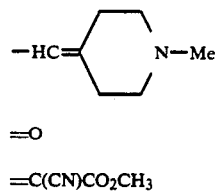

=O

=C(CN)CO$_2$CH$_3$

Other chromophores known in the art may be used as well. In principle, any chromophore that absorbs ultraviolet or visible radiation and that has orbitals conjugated with an orbital on an atom that forms a hydrogen bond in the complex will be suitable.

In an alternative embodiment, the compounds of the present invention selectively form strong complexes with creatinine in addition to the urea, guanidine or amidine compounds. Creatinine is a biologically important metabolite found in body fluids. Clinically, creatinine concentration in serum is an important indicator of renal, muscular and thyroid function. Normal physiological levels of creatinine in serum range from about 40 to about 110 $\mu$M.

In particular, the host molecules in this embodiment demonstrate improved binding and complexing with guest compounds such as urea, thiourea, guanidine, guanidine monosubstituted on one or two nitrogen atoms, creatinine, arginine or amidine compounds or an addition salt thereof. The superior complexes formed in this embodiment are achieved by the use of $\pi$ stacking interactions between the receptor host molecule and the guest analyte molecule. The advantage of $\pi$ stacking interactions lies in their ability to exert a stabilizing effect in various complexation reactions. Although the strong attractive interactions between $\pi$ systems have been known generally, suitable analytical reagents, ionophores or optical probes taking advantage of $\pi$ stacking interactions have been heretofore unavailable.

The sensitivity of an analytical method which relies on complexation of the analyte with a synthetic receptor is proportional to the stability of the complex formed between the receptor-host and the analyte-guest. In view of the desire to provide improved sensitivity for the above-described biologically important analytes, $\pi$ stacking groups are included in the receptors of this embodiment of the present invention.

The inclusion of additional monosubstituted or disubstituted aromatic rings in the receptors provides at least two advantages over other complexation methods. First, the increased sensitivity afforded by $\pi$ stacking detection of analytes even when the concentration is in amounts of only $10^{-8}$M. This feature is especially advantageous in situations where it is unlikely that hydrogen bonding alone between the receptor and guest will produce sufficiently stable complexes to allow detection. For example, some therapeutic agents such as pentamidine or other organic compounds of interest are present in the blood in concentrations ranging from only $10^{-7}$ to $10^{-8}$M. However, the inclusion of at least one $\pi$ stacking group in the receptor molecule allows for more sensitive detection of the analyte using, for example, ion-selective electrode techniques.

A second advantage afforded by including $\pi$ stacking groups such as monosubstituted or disubstituted aromatic rings in the host molecule is realized when the target analyte has no electric charge. In the past, neutral analyte molecules such as urea or creatinine have been difficult to detect using potentiometric electrode systems. As a result of including π stacking groups in the receptor molecules of the present invention, an alternative mode of detection is afforded which does not rely on a charge. The use of π stacking groups allows an optical response to be produced upon complexation between the receptor molecule and guest analyte. The optical response may be chromogenic or fluorogenic and occurs as a result of π—π interactions between the π systems of the host receptor molecule and the guest analyte molecule, such as creatinine. The optical signal generated may be used to quantify the analyte concentration by means of a UV-visible spectrophotometer or fluorometer.

In this embodiment, the molecules capable of forming stable complexes with urea, thiourea, guanidine, guanidine monosubstituted on one or two nitrogen atoms, creatinine, arginine or amidine compounds or an addition salt thereof have structures H-S, below, wherein C represents carbon atoms;
D independently represents nitrogen or oxygen atoms;
X independently represents (A)m;
A and G independently represent carbon, sulfur, nitrogen or oxygen atoms;
J independently represents carbon or nitrogen;
m=0-5;
s=1-7;
p and q independently represent 0-2;
V₁ and V₂ independently represent hydrogen, D or DαAr except that V₁ and V₂ are not both hydrogen and are not simultaneously hydrogen and D;
αAr is selected from the group consisting of OCH₂Ar, CH₂OAr, (CH₂)ₙAr wherein n=1-5, NCH₂Ar, OCOAr, CH₂COAr₂, NCOAr, SCOAr, OCH₂OAr, CH₂NAr, CO₂Ar, COCH₂Ar, CONAr, COSAr, wherein Ar is a monosubstituted aromatic group;
βAr is selected from the group consisting of CH₂Ar, (CH₂)ₘAr wherein m=1-4, COAr, OAr, NAr, SAr;
α independently represents OCH₂, (CH₂)ₙ, wherein n=1-5, NCH₂, OCO, CH₂CO, NCO, SCO, OCH₂O, CH₂N, CO₂, COCH₂, CON or COS, CH₂O;
β independently represents (CH₂)d, wherein d=1-4, CO, O, N or S;
Ar' is a disubstituted aromatic group; and
W₁ and W₂ independently represent hydrogen, nitrogen, oxygen or βAr; except that W₁ and W₂ are not both hydrogen, nitrogen and oxygen and at least one of W₁ and W₂ is βAr.

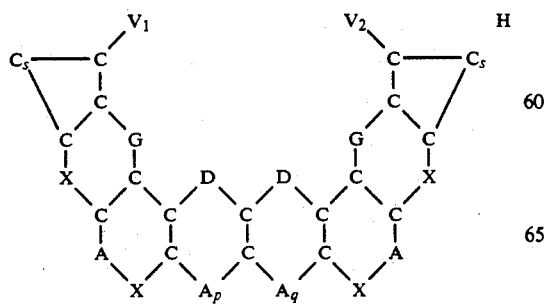

H

-continued

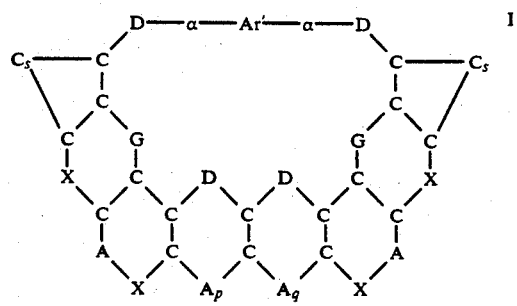

I

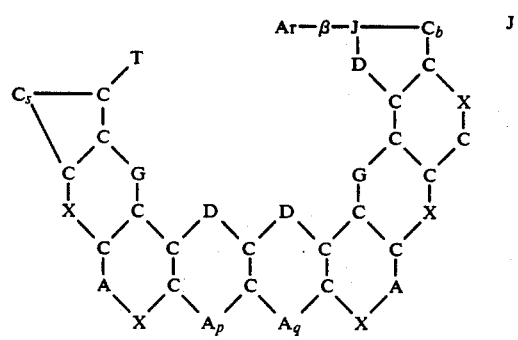

J

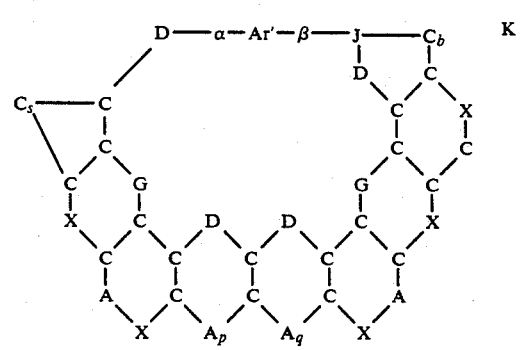

K

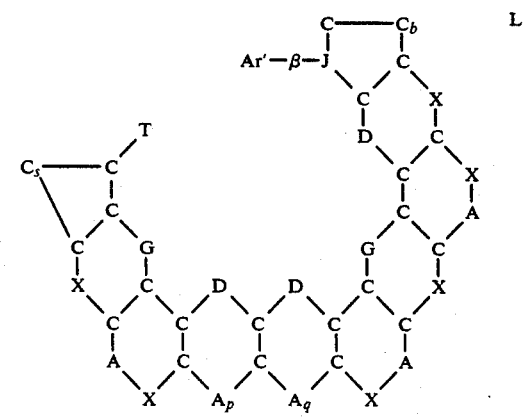

L

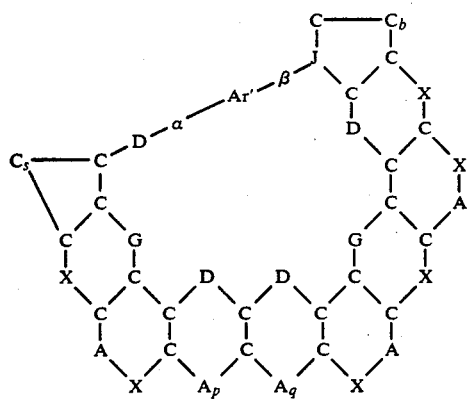

M

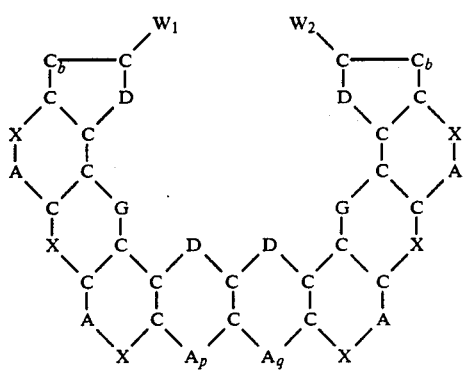

N

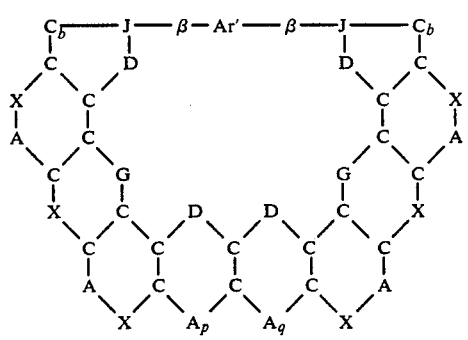

O

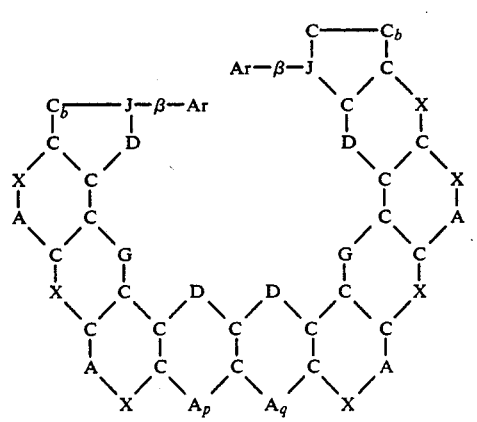

P

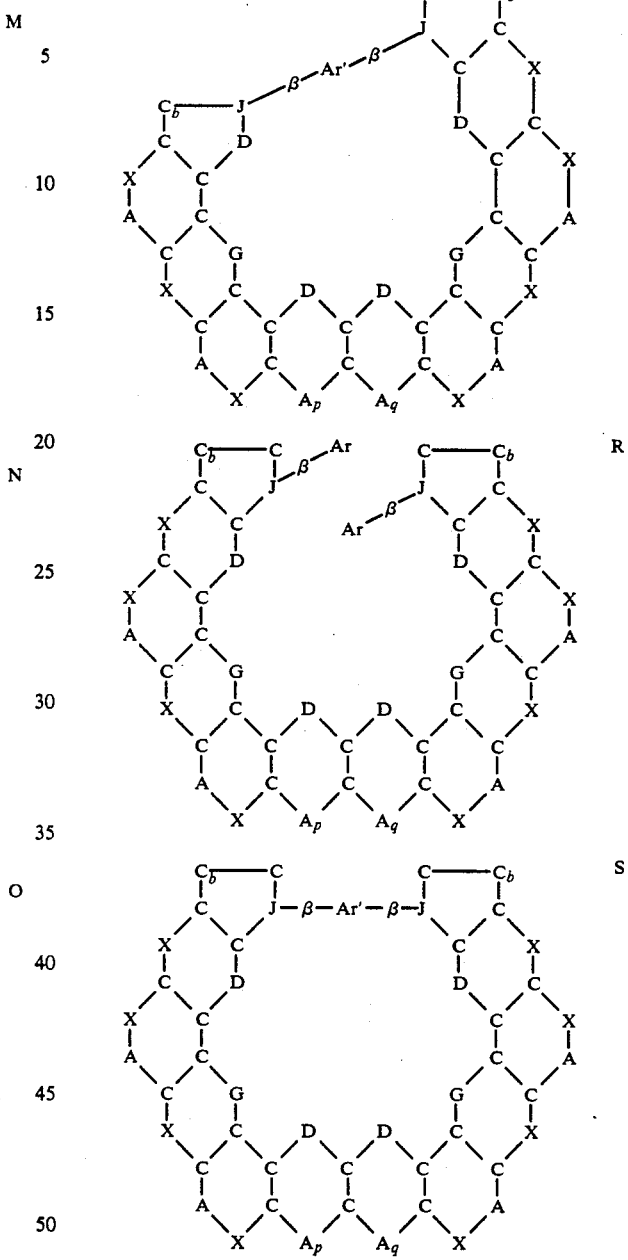

In this embodiment, a critical aspect of the molecules capable of forming stable complexes with the metabolites disclosed above is that they have at least one $\pi$ stacking group contained on the molecule. In a preferred embodiment, there are two $\pi$ stacking groups on the molecule. When so arranged, strong interactions can occur between the receptor and the guest compound searched for, such as pentamidine or creatinine. While not wishing to be bound to any particular theory, it is thought that at least part of the improved binding of complexing agents of the present invention is achieved by the use of spacer groups, designated herein as $\alpha$, $\beta$ and D$\alpha$. The $\pi$ stacking groups, designated herein as Ar and Ar' are attached to the spacer groups and thus can be positioned in planes that are parallel to the main receptor plane but 3-5 Å above or below this plane.

This arrangement effects maximum binding between the complexing agent and the sought after guest molecule by maximizing the π stacking interaction between the aromatic rings of the host, Ar and Ar' and the aromatic ring(s) of the guest.

As stated above, the π stacking groups may also serve a "reporter group" function. Upon the formation of a stable complex, the aromatic groups Ar, a monosubstituted aromatic ring group, and Ar', a disubstituted aromatic group, produce a shift in wavelength of absorption or emission and provide a chromophoric or fluorophoric optical response.

Ar and Ar' may be selected from carbocyclic or heterocyclic classes of aromatic rings. Examples of such aromatic rings include benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone and fluorene.

In preferred embodiments, Ar and Ar' may be aromatic rings bearing additional polar and/or ionizable substituents so that they function as chromogenic or fluorogenic reporter groups to signal complexation of the guest molecule. Chromogenic examples of Ar and Ar' include picrylamines, azulenes, nitrophenols, quinones, azo dyes and merocyanine dyes (e.g. phenol blue). Fluorogenic examples of Ar and Ar' include coumarins, fluorescein, Lucifer Yellow, 8-hydroxyquinoline, dansyl derivatives, porphyrins and phthalocyanines.

Some specific examples of molecules encompassed by the formulae H-S are shown below as compounds XXII-XXIV. These molecules form strong complexes with urea, guanidines, amidines and creatinine. The compounds may be in the form of ions such as those in their acid addition salts. The acid addition salt may be formed by treating urea, guanidine, and amidine with any acid such as HCl, HBr, etc. Some structures of complexes formed between compounds XXII-XXIV and guests such as urea, guanidine, amidine, creatinine, their acid addition salts and the derivatives thereof are shown as complexes XXIIa, XXIIb, XXIIIa, XXIIIb, XXIVa and XXIVb.

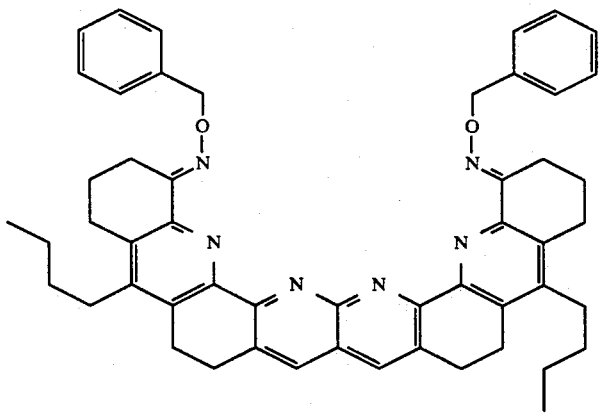

XXII

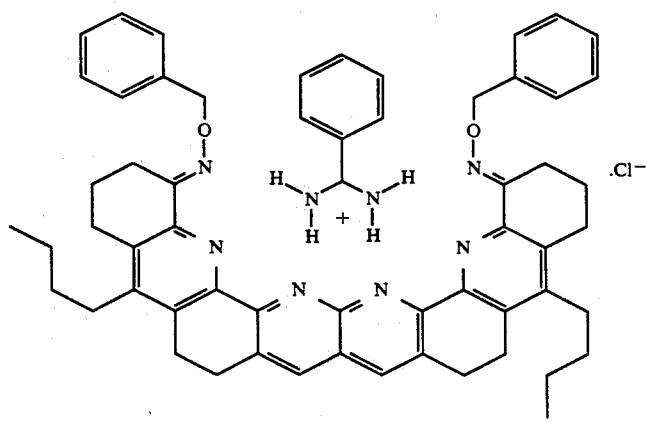

XXIIa

XXIIb
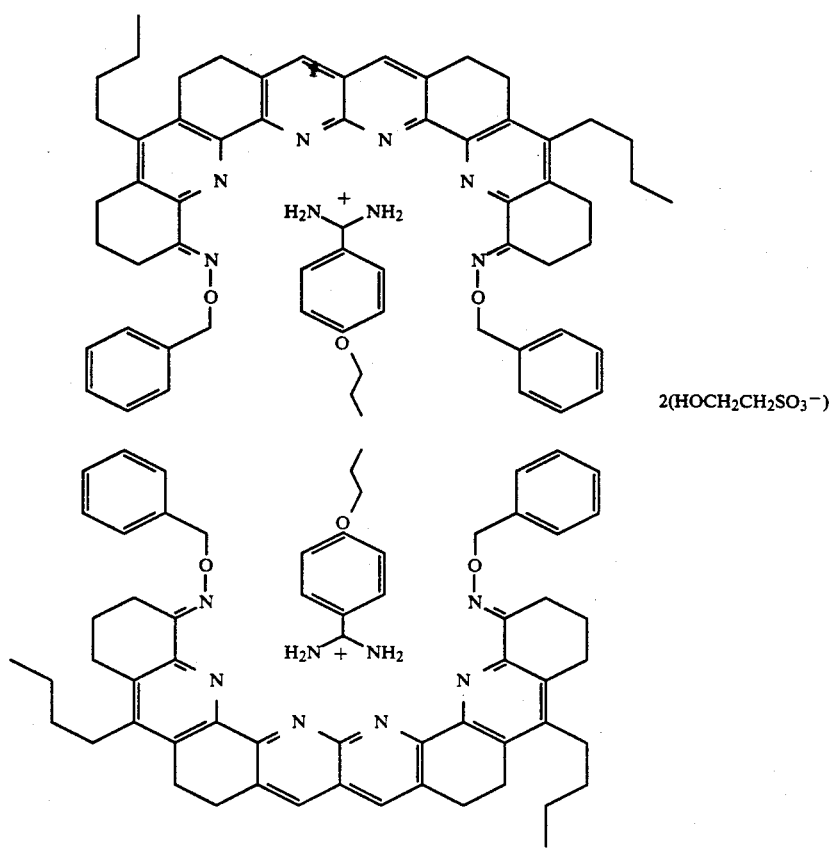
2(HOCH$_2$CH$_2$SO$_3^-$)
XXIII
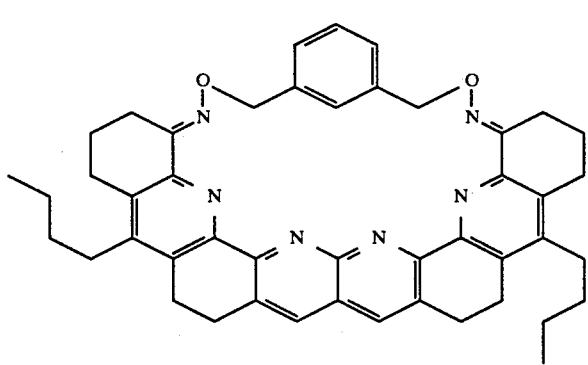
XXIIIa
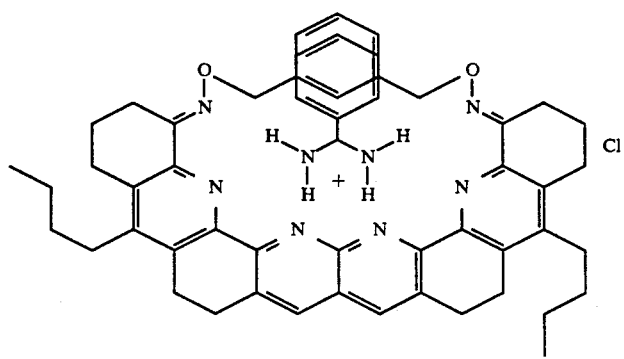

XXIIIb
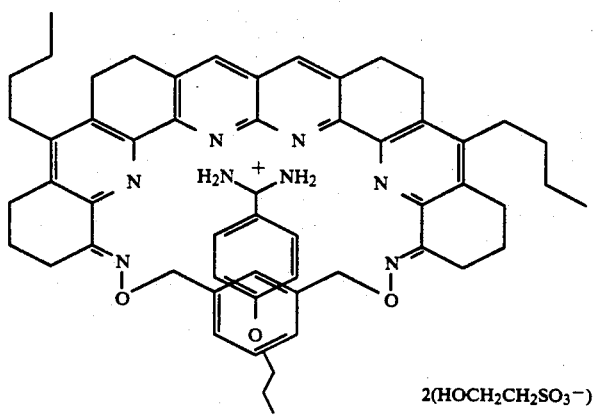
2(HOCH$_2$CH$_2$SO$_3^-$)
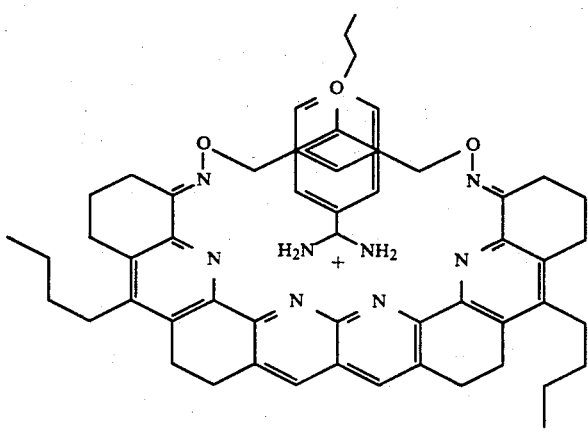
XXIV
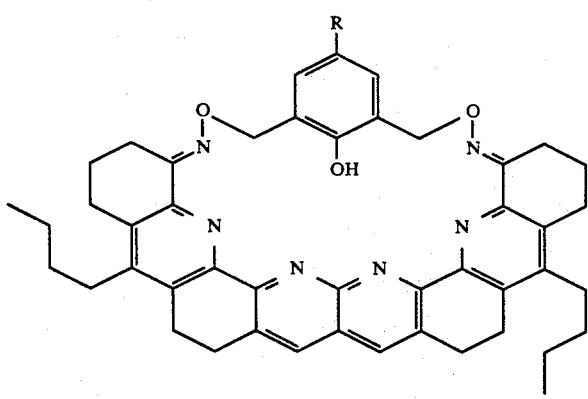
XXIVa
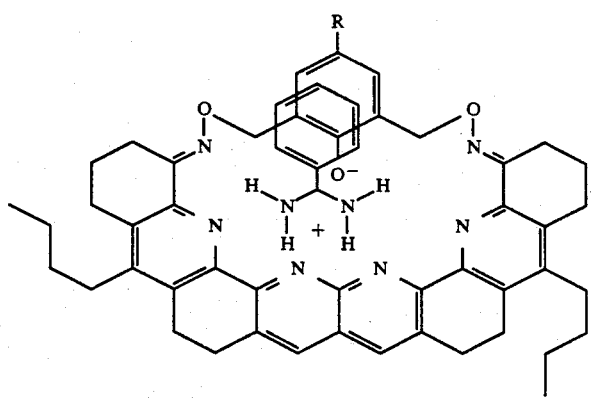

XXIVb

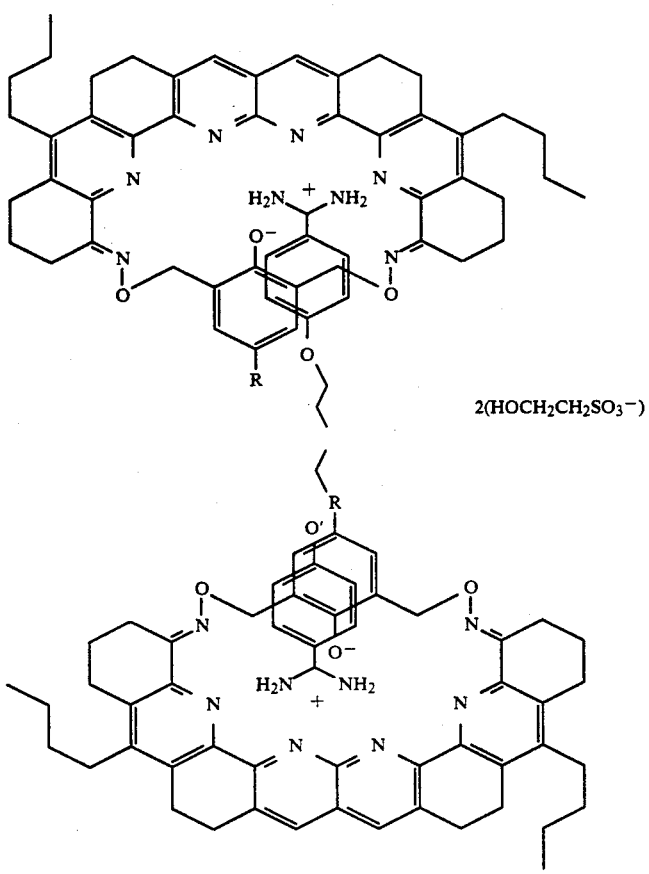

2(HOCH$_2$CH$_2$SO$_3^-$)

Compounds XXII and XXIII are typical examples of this embodiment. They both bind urea, guanidine and amidine and are especially well suited for binding benzamidines and their derivatives such as pentamidine. Compounds XXII and XXIII are specific examples of FIGS. H and I, respectively.

Compound XXIV is a specific example of FIG. I in which the disubstituted aromatic ring Ar' ring contains additional substituents which increase the strength of the $\pi$ stacking interaction and increase the optical response upon binding benzamidines.

Compound XXIVa shows a complex of this compound with benzamidinium. This complex is stabilized by an ionic interaction between the negatively charged oxygen atom on the disubstituted aromatic ring and the positive charge on the guest molecule.

Compound XXIVb shows compounds XXIV complexed with pentamidine, a specific molecule with clinical interest. The ionic interaction between the $\pi$ stacked aromatic rings of the host and guest in XXIVa and XXIVb enhances the optical response by a donor-acceptor electronic exchange.

In a further embodiment, the complexing agents of the present invention also provide an ionophoric or chromophoric response when the complex has been formed by including in-plane dye groups within the complexing agents. These novel features allow the complexing agents to be included in highly selective sensors which can indicate the concentration of a given analyte such as sulfur guanidine or aminoguanidine, creatine and urea, amidine-based therapeutic agents such as pentamidine in a given sample and provide a measurable electrical or optical signal response.

In accordance with this embodiment, the complexing agents of the present invention may be included in, for example, ion-selective electrodes and/or fiber optic fluorosensors. Ion-selective electrodes (ISE) generally denote membrane electrodes which respond selectively toward an ion species even in the presence of other ions. The membrane denotes a thin section of electrically insulating material separating two solutions across which a potential develops at the membrane interface. A rapid ion-exchange process takes place between the free ions in solution and the same ions bound to the complexing molecules. The selectivity of the electrode depends primarily on the selectivity of the ion-exchange process. An ionophore is impregnated into the membrane and the particular ionophore used endows the membrane with its selectivity.

The complexing agent compounds of this embodiments have structures T-Y and are shown below, wherein:

C represents carbon atoms;
D independently represents nitrogen or oxygen atoms;
X independently represents (A)m;
A and G independently represent carbon, sulfur, nitrogen or oxygen atoms;
T independently represents oxygen, nitrogen or sulfur;
m=0-5;
s=1-7;

p, q, p' and q' independently represents 0-2;
τ is selected from the group consisting of O, N, S, OH, OR, OAr, NH₂, NHAr, NHCOR, NHOH, NHOR, NR₂, NHR, SH, SR, SAr, wherein Ar is a monosubstituted aromatic group and wherein R is an alkyl or substituted alkyl; and
L independently represents a hydrocarbon or heterocarbon group having from about three to about ten members.
T
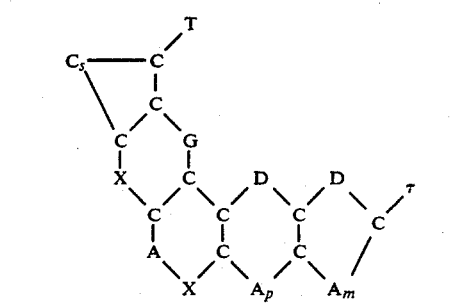
U
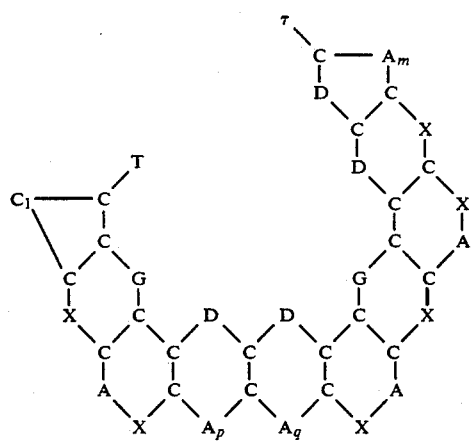
V
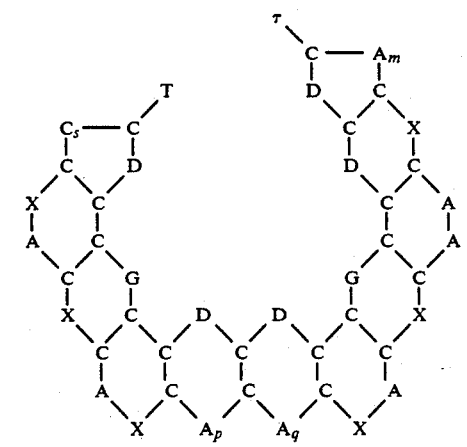
W
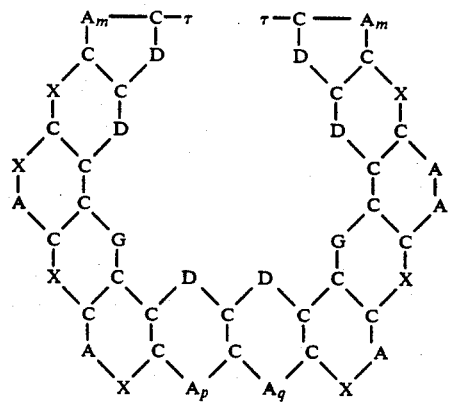
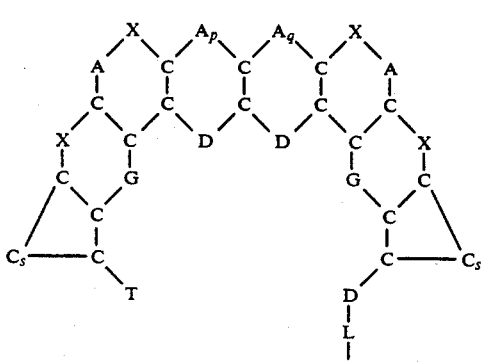
X
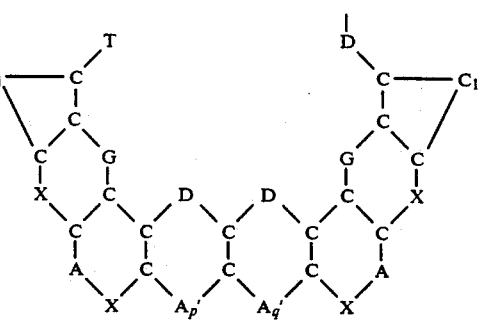
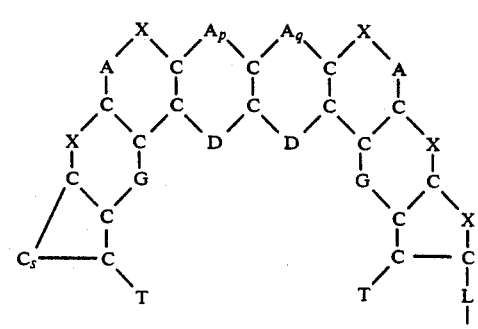

-continued

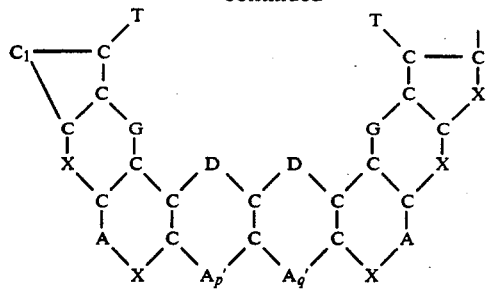

The structures shown above as T–Y comprise the nucleus of atoms of the complexing agents shown in this preferred embodiment. Each atom indicated in the structure possesses a sufficient number of bonds either to adjacent atoms or to other atoms not shown to form stable compounds.

In this embodiment, a critical aspect of the claimed molecules is that they have in plane dye groups that strengthen the complexes formed between the host molecule and guest molecule by forming additional hydrogen bonds or ionic interactions and/or provide an optical response to complexation. Key groups to achieving these effects are shown as T and τ in the positions shown in FIGS. T–Y. In addition, it is preferred that these compounds have additional substituents that extend the conjugated dye chromophores. It is desirable to have chromophoric substituents that can be detected by UV-visible and fluorescence spectroscopy wherein the electrons of the chromophoric group are conjugated with the electrons of an atom that forms a hydrogen bond to a guest such as urea or guanidine. Examples of such substituents include CN, $CO_2R$, $CO_2H$, $CONH_2$, CONHR, $CONR_2$, aryl, $NH_2$, NHR, $NHR_2$, COAr, NHAr, $NAr_2$, $CH=CH_2$, CH=CHR, CH=CHAr, SH, SR, SAr, and the like wherein Ar is a monosubstituted aromatic group and R is an alkyl or substituted alkyl.

In FIGS. X and Y, there is shown an advantageous linking group L. In situations where the guest of interest contains two urea, guanidine or amidine moieties, it is advantageous to link two receptor molecules by means of a linking group L. A principal purpose for L is to position the two receptor units at the correct distance to bind the guest of interest.

Moreover, L may function to extend the dye chromophore when L contains unsaturated groups and/or hetero atoms such as oxygen, nitrogen or sulfur. Examples of linking groups, L, include, for example, a hydrocarbon or heteroatom-containing having from about three to about ten members. The group may also include aromatic rings.

The basic molecules prepared in accordance with this embodiment consist of atoms shown in FIGS. T–Y and include as many additional hydrogen or other atoms required to render the molecules stable. As discussed previously, any other atoms are possible although they are usually selected from among carbon, oxygen, nitrogen, sulfur, phosphorous, fluorine, chlorine, bromine or iodine. Moreover, the additional atoms may also constitute any organic or inorganic moiety as set forth in the above-described embodiments and include, for example, inorganic moieties such as halo, nitro, amino and the like while suitable organic moieties include, for example, alkyl, aryl, and the like.

In general, the substituents added to compounds T–Y may be the same as those added to compounds A–G.

Some specific examples of the molecules encompassed by formulas T–Y are shown as compounds XXV–XXXI. These molecules provide an ionophoric or chromophoric response when a complex has been formed between one of the compounds XXV–XXXI listed above and a guest molecule such as urea, creatinine, guanidine, amidine or their addition salts. Examples of complexes formed between compounds XXV–XXXI and a guest of interest and derivatives thereof are shown as XXVa, XXVIa, XXVIIa, XXVIIIa, XXIXa, XXXa, XXXb, XXXIa and XXXIb. In this embodiment, the observable optical changes which occur when complexes are formed may occur by proton transfer between the chromogenic unit found on the complexing agent and the guest which is complexed thereto. Other chromophores and/or ionophores known in the art may be used as well, so long as the integrity of the complexing agent is preserved.

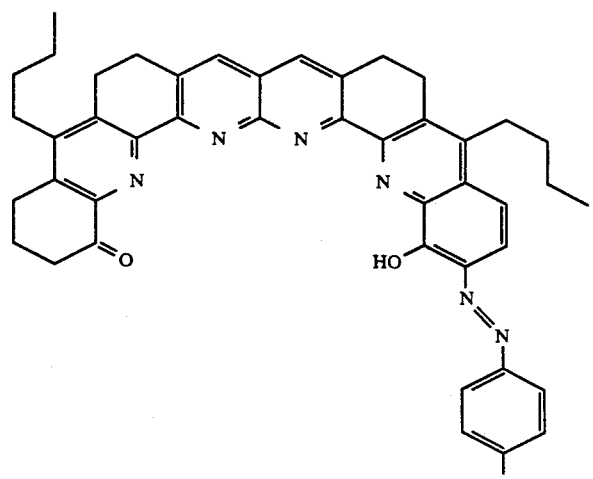

-continued
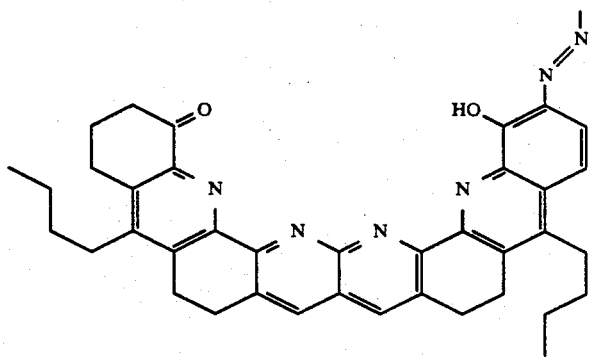
XXV
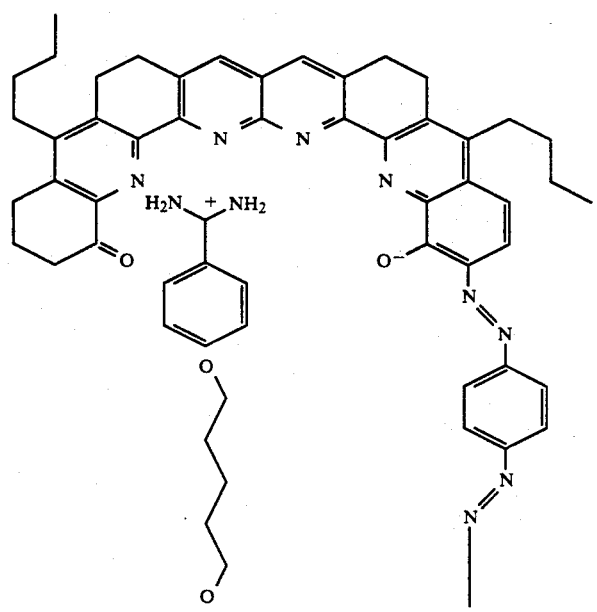
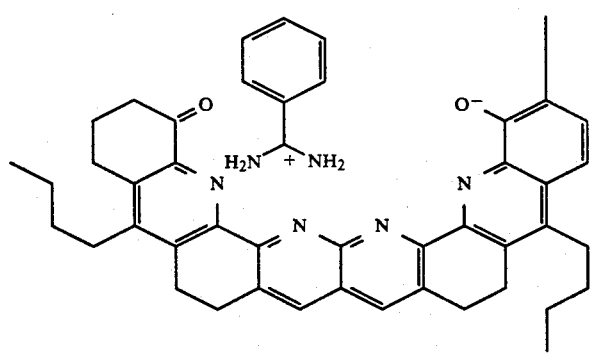
XXVa
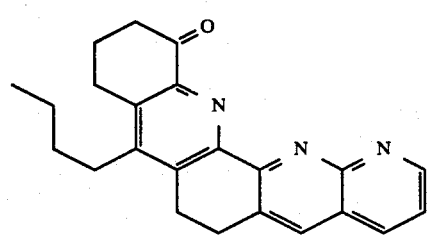
XXVI

-continued
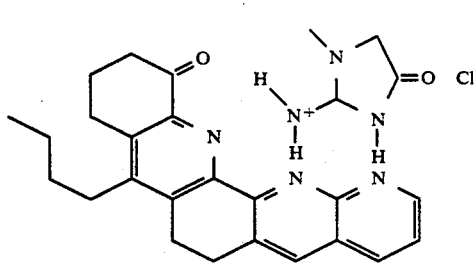
XXVIa
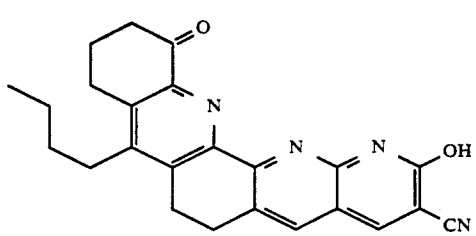
XXVIII
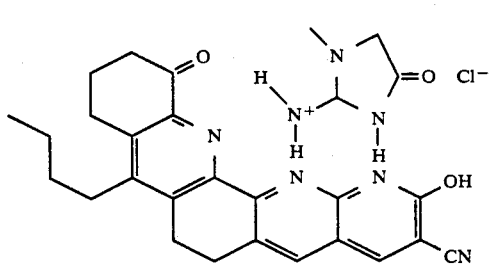
XXVIIIa
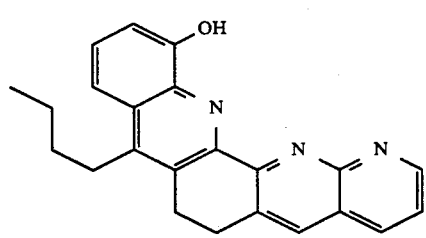
XXIX
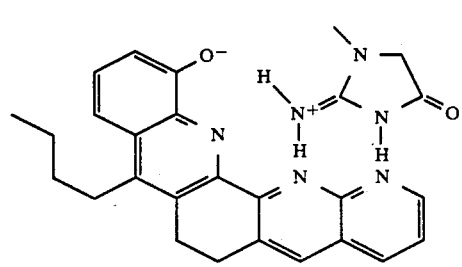
XXIXa -continued
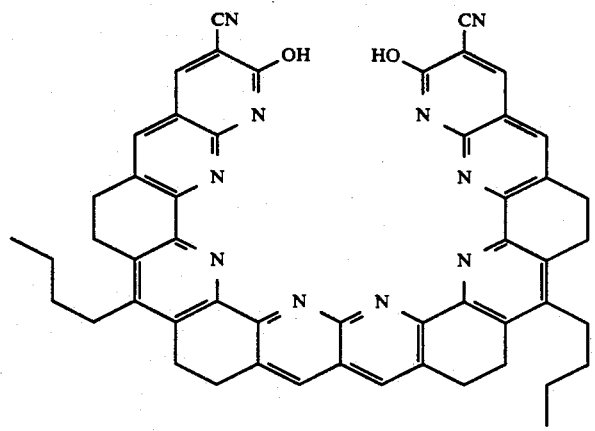
XXX
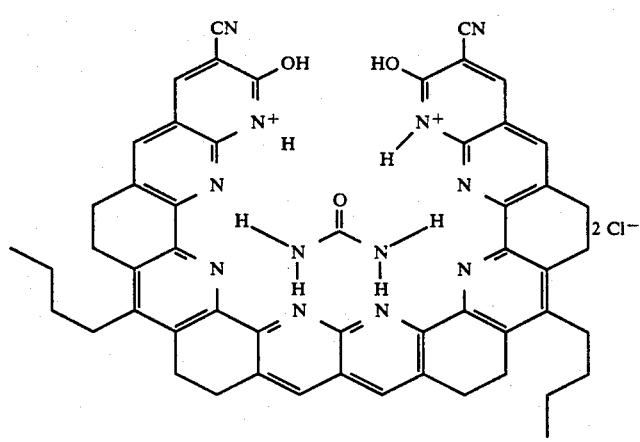
XXXa
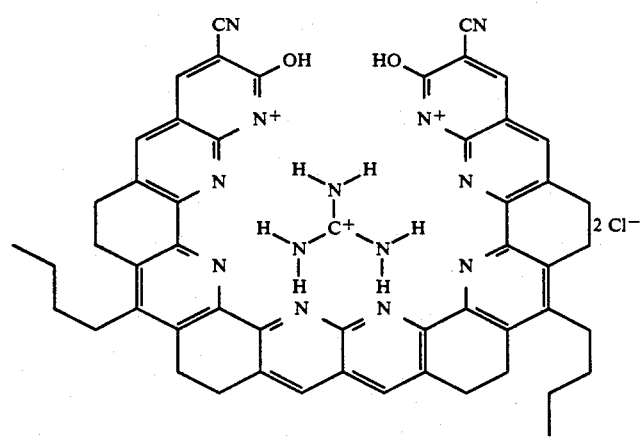
XXXb

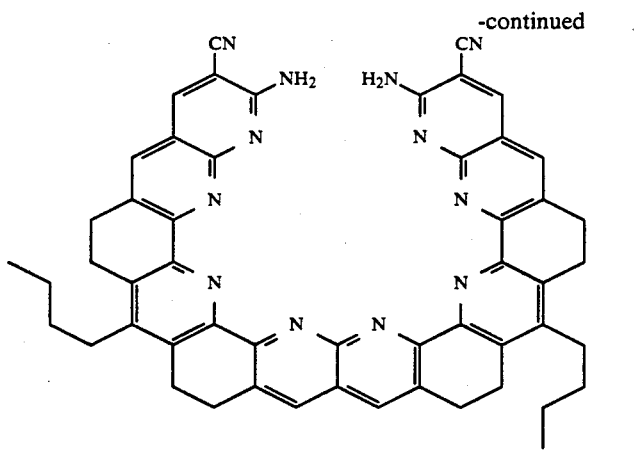

XXXI

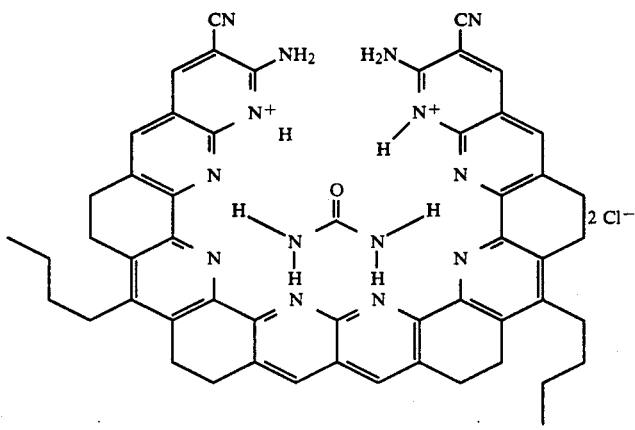

XXXIa

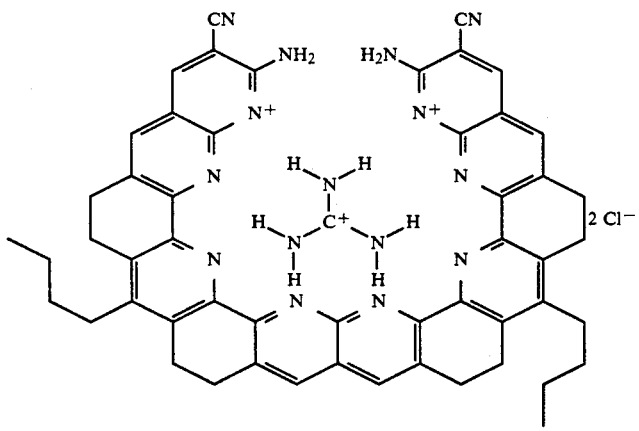

XXXIb

Compounds XXV–XXXI are specific examples of this preferred embodiment represented by FIGS. T–Y. Each compound is capable of bind urea, guanidine, amidines and creatinine.

Compound XXV is a specific example of FIG. Y and contains two receptors and chromogenic groups linked together by an aromatic bis(azo) linker group. The linker group serves two important purposes. First, the linker positions the receptor's benzamidine binding sites at a distance appropriate for binding pentamidine as shown in XXVa. Secondly, the azo groups are conjugated to the terminal phenol rings of each benzamidine binding site. This increases the acidity of each hydroxyl group so that ionization takes place upon binding and causes a substantial change in the color of the receptor.

Compound XXVII is a specific example of FIG. T in which the $\tau$ group is amino and the dye chromophore is extended by conjugation with a carbonyl group (T) at one end and the CN group at the other end of the receptor. The water soluble addition salt of this molecule with HCl is fluorescent and the fluorescence is quenched by binding creatinine to form the complex shown as XXXIIa. This quenching can be used to determine the concentration of creatinine in an aqueous solution.

The compounds of the present invention may be prepared by methods generally known in the prior art. The synthesis of compounds IV, V, IX, IXe, XXIII and XXVII will be used for illustration purposes. Modifications of the illustrated reactions will be apparent to those skilled in the art for making other compounds of the invention.

A first key intermediate in the synthesis of compounds IV–IX is 8-n-butyl-2-hydroxytricyclo[7.3.1.0$^{2,7}$]tridecan-13-one, XIV, which may be prepared by treating cyclohexanone with valeraldehyde in a mole ratio of at least 2:1 in the presence of strong base such as potassium hydroxide in ethyl alcohol in accordance with reaction 1. The reaction appears to involve the following sequence: aldol condensation to form 2-pentylidenecyclohexanone, Michael addition of cyclohexanone enolate, and intramolecular aldol condensation of the resulting 1,5-diketone. Many aldol products are formed and the yield of ketoalcohol depends strongly on: 1) reaction temperature; 2) use of a large excess of cyclohexanone; and 3) prolonged addition of the aldehyde. The ease of product isolation is particularly dependent on its crystallinity and solubility. Since ketoalcohol is capable of undergoing a reverse aldol condensation, reactions of XIV may be considered to constitute reactions of the resulting diketone.

A second key intermediate is 9-n-butyl-1,2,3,4,5,6,7,8-octahydroacridine, XV. This intermediate may conveniently be prepared by the well-known reaction of a 1,5-diketone with ammonium, as described by Bell et al., Tetrahedron Lett., 28, 4817–4820 (1987). As reported in the Bell et al. article, it has surprisingly been discovered that a cupric salt such as cupric acetate enhances the yield and purity of the product formed. It is especially desirable to conduct this reaction in the presence of at least two equivalents of the cupric salt in the absence of an oxidizing agent such as oxygen. This improved method for converting 1,5-diketones to the corresponding pyridine compound is applicable to any such reaction of a 1,5-diketone with ammonia. The preferred cupric salt is the cupric salt of a carboxylic acid, such as cupric acetate, cupric propionate and cupric butyrate. Cupric acetate is especially preferred. The solvent may conveniently be the corresponding carboxylic acid.

Ketoalcohol XIV may be converted to 9-n-butyl-1,2,3,4,5,6,7,8-octahydroacridine, XV, by treatment with ammonia in accordance with reaction 2. Suitable conditions for this reaction include treatment with ammonium acetate in refluxing acetic acid under nitrogen in the presence of cupric acetate, such as a molar ratio of cupric acetate to XIV of at least about 2.0, and preferably at least about 2.5.

Compound XV may be converted to compound XVII as shown in reactions 3 and 4 by causing the rearrangement of the acetate of the corresponding N-oxide (XVI) of compound XV and isolating the resulting alcohol XVII.

Reaction 3 describes two alternate methods for conversion of a pyridine to its N-oxide: MCPBA and Oxone (potassium hydrogen persulfate). Whereas MCPBA oxidation is relatively standard, the availability of 85% pure MCPBA is limited. Pyridine N-oxides may also be prepared with hydrogen peroxide in acetic acid, but reaction time is variable and removal of acetic acid is inconvenient for large scale preparations. Potassium hydrogen persulfate (Oxone) is an inexpensive alternative to MCPBA in many oxidation reactions. (Trost, et al. *Tetrahedron Lett.* 1981, 22, 1287–1290; Gallopo, et al., *J. Org. Chem.* 1981, 46, 1684–1688; Cicala, et al. idid. 1982, 47, 2670–2673; Jeyaraman, et al., *J. Am. Chem. Soc.* 1984, 106, 2462–2463; Murray, et al., *J. Org. Chem.* 1985, 50, 2847–2853; Davis, et al., ibid. 1988, 53, 2087–2089.)

The oxidation procedure given below in the examples avoids the formation of volatile peroxides, which occurs in ketone-catalyzed N-oxidation of pyridine by persulfate. A 50% excess of Oxone is used, but less oxidant leads to inconveniently long reaction time.

Synthesis of compounds IV–IX from 1,2,3,4,5,6,7,8-octahydroacridines requires oxidative functionalization of the 4-position ($CH_2$ group bonded to the pyridine 2-position). In reaction 4, this is accomplished by "Katada" or "Boekelheid" rearrangement of the N-oxide. Deoxygenation of the acetic anhydride prior to addition results in slightly higher yields.

Compound XVIIa, which is obtained by benzaldehyde condensation from XVII, may be converted to IV as shown in reaction 5. Swern oxidation of XVIIa yields ketone XVIII, which undergoes a Friedlander condensation with a 4-aminopyrimidine-5-carboxaldehyde to afford XIX. (Bredereck et al., Chem. Ber., 100, 3664–3670 (1967)). The pyrimidine ring of XIX undergoes hydrolysis to aminoaldehyde XX, which is condensed with another equivalent of ketone XVIII. The resulting dibenzylidine derivative XXI is then ozonized to diketone IV. This synthesis is effective mainly because two efficient Friedlander condensations are used to form the new 1,8-naphthyridine ring. The synthesis affords diketone IV in 20–35% overall yield.

Additional Friedlander condensation reactions can be employed to convert compound IV into other compounds of the invention. Thus, treatment of IV with two equivalents of 2-methylacrylic acid yields V. Treatment of IV with one equivalent of 2-aminopyridine-3-carboxaldehyde yields VIIIb. A second equivalent yields IX.

Similarly, three additional rings may be added to structure IX, which is shown generically as structure F, to complete the macrocyclic structure of fused rings as shown in structure IXe, which is shown generically as structure G. This type of macrocyclic structure is referred to as a torand. Torand IXe may be prepared, for example, by a double condensation of 2-amino-7-n-butyl-11-oxo-5,6,8,9,10,11-hexahydrobenzo[b][1,10]-phenanthroline-3-carboxaldehyde, XXI, as shown in reaction 6. Structure XXI may, in turn, be prepared by oxidation of the corresponding benzylidine, XX with CsOH.

Chromophoric groups can be added by methods known in the art. For example, IV may be converted to X by the method of Krasnaya, et al. or of Nair, et al. (Krasnaya, et al. Akad. Nauk, Eng. Trans., 102–107 (1978); Nair, et al. Tetrahedron Lett., 21, 3155–3158 (1980), J. Org. Chem., 46, 4759–4765 (1981)).

Alternatively, torand IXe may be prepared by ozonolysis of benzylidineketone XVIIa, which gives an octahydroacridinediketone that may be condensed with two equivalents of 4-aminopyrimidine-5-carboxaldehyde. The terminal pyrimidine rings of the resulting seven-ring intermediate are then hydrolyzed to give a bis(aminoaldehyde) analogous to the mono(aminoaldehyde) XX. Friedlander condensation of this intermediate with diketone IV gives a 15-ring macrocylcle containing three pyridines and three 1,8-naphthyridines.

The 24-membered ring cavity of this macrocycle has a bearly ideal shape and size to form a stable, lipophilic complex having six hydrogen bonds with guanidinium.

Receptor XXIII is synthesized in three steps using standard synthetic procedures. In the first step, intermediate XXXII is prepared from α,α'-dibromometaxylene and N-hydroxyphthalimid. In the second step, XXXII is hydrolized to XXXIII. XXXIII is then condensed with receptor IV, forming π stacking receptor XXIII.

The synthesis of receptor XXVII begins with compound XX which was used previously as an intermediate in the synthesis of receptor IV. The HCl salt of XX is condensed with malononitrile forming intermediate XXXIV. As in the synthesis with other ketones described herein, the benzylidine group of intermediate XXXIV is cleaved by ozonolysis. This procedure gives the fluorescent HCl salt of receptor XXVII which can be used directly for analysis of creatinine by fluorescence quenching.

EXAMPLES

A.
8-n-Butyl-2-hydroxytricyclo[7.3.1.0$^{2,7}$]tricedan-13-one.(XIV)

A 2-L, three necked flask is equipped with a magnetic stirring bar, a thermometer, a 500-mL pressure equalizing dropping funnel, and a reflux condenser equipped with a nitrogen gas inlet tube, which is attached to a mineral oil bubbler. The flask is charged with 1.0 L (947 g, 9.65 mol) of cyclohexane (Note 1) then flushed with nitrogen. The cyclohexane is heated to 70°-75° C. under nitrogen, then a solution of 9.0 g (0.14 mol) of potassium hydroxide (Note 2) in 85 mL of absolute ethanol is added in one portion, followed by a solution of 150 mL (122 g, 1.4 mol) of valeraldehyde (Note 3) in 140 mL of absolute ethanol, added dropwise over a period of 8 hrs. The stirred reaction mixture is maintained at 70°-75° C. throughout the addition period and for 11-14 hrs. after the addition is complete. The reaction flask is then immersed in an ice bath and crystallization is initiated by scratching with a glass rod or by adding seed crystals. Crystallization is complete within four hours at 0° C. and the colorless product is collected by vacuum filtration and washed with cooled ether (200 mL) (Note 4). The product is recrystallized from methanol, washed with water and dried (1 mm, 60° C.) to give 146 g (40%) of 8-n-butyl-2-hydroxytricyclo[7.3.1.0$^{2,7}$]tridecan-13-one, mp 140°-141° C. (Note 5).

B. 9-n-Butyl-1,2,3,4,5,6,7,8-octahydroacridine.(XV)

A 500 mL, one-necked flask equipped with a magnetic stirring bar, a Claisen adapter, and a reflux condenser equipped with a nitrogen inlet attached to a bubble (Note 6) is charged with 17.0 g (0.22 mol) of ammonium acetate, 82 g (0.41 mol) of cupric acetate monohydrate and 200 mL of glacial acetic acid, then flushed with nitrogen. The mixture is stirred and heated at reflux under a static atmosphere of nitrogen for 15 min., then the resulting solution is cooled slightly as 53 g (0.20 mol) of 8-n-butyl-2-hydroxytricyclo[7.3.1.0$^{2,7}$]-tridecan-13-one is added in several portions. The blue-green reaction mixture is stirred and heated at reflux under nitrogen for 3 hrs., then the reaction flask is cooled in an ice bath for 2-3 hours. Precipitated cuprous acetate is removed by vacuum filtration using a fitted glass funnel (medium or coarse porosity) and washed with 100 mL of acetic acid. The combined filtrates are diluted with 500 mL of water, cooled in ice and carefully neutralized by slow addition of aqueous sodium hydroxide (Note 7). The resulting cloudy mixture is transferred to a separatory funnel and extracted with ether (400 mL, then 2×200 mL). The combined ether extracts are washed with 140 mL of 3% aqueous sodium hydroxide and 70 mL of saturated aqueous sodium chloride, then dried using anhydrous magnesium sulfate with 1 g of decolorizing charcoal (Norit). The solids are removed by filtration and washed with at least 200 ml of ether. The combined filtrates are concentrated to minimum volume using a rotary evaporator and residual solvent is removed under vacuum (1 mm). The product is obtained as a beige crystalline solid, mp 35°-37° C., 47 g (97%) (Note 8).

C.
9-n-Butyl-1,2,3,4,5,6,7,8-octahydroacridine-N-oxide(XVI)

Method 1:

Into a 2 L round-bottomed flask equipped with a magnetic stirrer and a reflux condenser fitted with a nitrogen inlet are placed 38.0 g (0.16 mol) of 9-n-butyl-1,2,3,4,5,6,7,8-octahydroacridine, 72.0 g (0.12 mol) of Oxone (Note 9), 28.5 g (0.34 mol) of NaHCO$_3$, 790 mL of methanol and 240 mL of water. The resulting suspension is stirred at 45°-50° C. in an atmosphere of nitrogen for 24 hrs. (Note 10). The cooled reaction mixture is vacuum filtered, washing the residual salts with methanol (2×50 mL). The methanol is removed from the combined filtrates by means of a rotary evaporator and the resulting mixture is extracted with methylene chloride (3×100 mL). The combined extracts are washed with water (2×50 mL), dried using anhydrous magnesium sulfate and concentrated to dryness by means of a rotary evaporator. Residual solvent is removed at 0.1 mm, yielding 39 g (96%) of 9-n-butyl-1,2,3,4,5,6,7,8-octahydroacridine-N-oxide as a pale yellow solid, mp 89°-92° C. (Note 11).

Method 2:

Into a 1 L round-bottomed flask equipped with a magnetic stirrer, a reflux condenser and a 250 ml addition funnel are placed 56.3 g (0.26 mol) of m-chloroperoxybenzoic acid (Note 12) and 350 mL of methylene chloride. The resulting suspension is stirred as a solution of 38.0 g (0.16 mol) of 9-n-butyl-1,2,3,4,5,6,7,8-octahydroacridine in 120 mL of methylene chloride is added rapidly. When the reaction mixture ceases to boil gently from the heat of reaction, the reaction flask is warmed to extend the reflux period to a total of 2.5 hrs. (Note 10). The reaction mixture is cooled to room temperature, extracted with 0.5M aqueous sodium hydroxide (4×450 mL), dried using anhydrous sodium sulfate and concentrated under reduced pressure using a rotary evaporator. Residual solvent is removed at 0.1 mm, yielding 40 g (99%) of 9-n-butyl-1,2,3,4,5,6,7,8-octahydroacridine-N-oxide as a yellow crystalline solid, mp 96°-100° C.

D.
5-Benzylidene-9-n-butyl-1,2,3,4,5,6,7,8-octahydroacridine-4-ol HBr Salt.(XVIIa (HBr))

A mixture of 40 g of crude 9-n-butyl-1,2,3,4,5,6,7,8-octahydroacridine N-oxide and 300 mL of degassed acetic anhydride is heated under nitrogen at 100°-110° C. for 2 hours, then 100 mL (104 g, 1 mol) of benzaldehyde is added. The reaction mixture is heated under reflux for 18 hours, then 300 mL of distillate is collected by simple distillation under vacuum (25-35 mm). A solution of the residual dark oil in 150 mL of methylene chloride is washed with 2×100 mL of 2M aq. NaOH, then evaporated to dryness. A mixture of the residue, 150 mL of 48% aq. HBr and 800 mL of water is distilled at atmospheric pressure until 600 mL of distillate is collected. The port liquid is cooled with ice for 2 hours, then the aqueous layer is decanted. The residual dark, viscous oil is taken up in about 200 mL of acetone and the resulting mixture is stored at 0°–5° C. for several hours. The crude product is collected by vacuum filtration and recrystallized from acetone/ethyl acetate, yielding 34.8 g (50.1%) of yellow crystalline product, m.p. 183.5°–184.5° C.

E.
5-Benzylidene-9-n-butyl-2,3,5,6,7,8-hexadro-4(1H)-acridinone.(XVIII)

A mixture of 21.4 g of 5-benzylidine-9-butyl-1,2,3,4,5,6,7,8-octahydroacridin-4-ol HBr salt, 100 mL of methylene chloride and 100 mL of 1M aq. NaOH is shaken in a separator funnel until all solids have dissolved in the methylene chloride layer. The organic layer is collected and dried with anhydrous $Na_2SO_4$. After removing solvent by rotary evaporator and high vacuum (0.1 mm), the residue is dissolved in 140 mL of DMSO. Acetic anhydride (90 mL) is added to the DMSO solution and the reaction mixture is stirred for 6 hours. Water (600 mL) is added and the mixture is extracted with 3×200 ml of ether. The combined ether layers are washed with 3×100 mL of 1M NaOH solution and dried over anhydrous $Na_2SO_4$. Solvent is removed under vacuum and the residue is recrystallized from ethylacetate/hexane to give 12.5 g (72%) of crystalline product, m.p. 119.5°–112.5° C.

F.
1,16-Dibenzylidene-5,12-di-n-butyl-1,2,3,4,6,7,10,11,13,14,15,16-dodecahydrodibenzo[b,g][1,10]phenanthrolino[2,3-b][1,10]phenanthroline. (XXI)

To a refluxing solution of 3.47 g of 5-benzylidene-9-n-butyl-2,3,5,6,7,8-hexahydro-4(1H)-acridinone and 1.24 g of 4-amino-pyrimidine-5-carboxaldehyde in 800 mL of methanol is added 0.1 mL of 15% methanolic KOH. The mixture is refluxed for 24 hours and 2.58 g precipitate is collected by vacuum filtration after cooling. The solution of this intermediate in 500 mL of 2M HCl is heated under reflux for 3 hours. The reaction mixture is cooled and filtered, yielding 2.53 g of orange solid, which is then mixed with 2.08 g of 5-benzylidene-9-n-butyl-2,3,5,6,7,8-hexahydro-4(1H)-acridinone and 250 mL of methanol and heated to reflux, then 4 mL of 15% methanolic KOH is added and the refluxing is continued for 24 hours. Yellow solid product is obtained by vacuum filtration, 3.82 g (52.2%), m.p. 282° C. (dec.).

G.
5,12-Di-n-butyl-2,3,4,6,7,10,11,13,14,15-decahydrodibenzo[b,g,][1,10]phenanthrolino[2,3-b][1,10]phenanthroline1,16-dione.(IV)

1,16-Dibenzylidene-5,12-di-n-butyl-1,2,3,4,6,7,10,11,13,14,15,16-dodecahydrodibenzo[b,g][1,10]phenanthrolino[2,3-b][1,10]phenanthroline (0.3 g) is dissolved in a mixture of 110 mL of methylene chloride and 40 mL of methanol. At −78° C. ozone is bubbled through the orangish-yellow solution until the color of the solution is changed to pale greenish-yellow. The solution is then purged with $N_2$ for 5 minutes. Dimethyl sulfide (0.5 mL) is added and the reaction mixture is warmed to room temperature. The solvents are removed by rotary evaporation. The residue is washed with 100 ML of ether, yielding 0.24 g of crude product (100%), which is recrystallized with a mixture of methylene chloride and isopropanol. Slow evaporation of methyl chloride yields 0.11 g (46%) of crystalline product, m.p. 296°–300° C. (dec.).

H.
7,14-Di-n-butyl-5,6,8,9,12,13,15,16-octahydrodiquino[8,7-b,g][1,10]-phenanthrolino[2,3-b][1,10]phenanthroline.(V)

A solution of 5 mmol of 5,12-di-n-butyl-2,3,4,6,7,10,11,13,14,15-decahydrodibenzo[b,g][1,10]-phenanthroline-1,16 dione, 12 mmol of o-allylhydroxylamine hydrochloride, 1 g of anhydrous sodium acetate, 1.2 g of anhydrous sodium carbonate and 30 ml of ethanol is stirred under reflux for 6 hours. The ethanol is evaporated and the residue is extracted with chloroform. The combined chloroform extracts are washed with water, dried over $MgSO_4$ and evaporated to obtain the oxime intermediate, which is purified by recrystallization or chromatography. The intermediate is heated at 180°–185° C. in a sealed glass tube for 48 hours. The cooled tube is opened and the contents are dissolved in chloroform. The chloroform solution is washed with water, dried over $Na_2SO_4$ and evaporated. The crude product is purified by recrystallization or chromatography.

I.
8,15-Di-n-butyl-6,7,9,10,13,14,16,17-octahydrodi(benzo[b][1,8]naphthyridino)[9,8-b,g][1,10]-phenanthrolino[2,3-b][1,10]phenanthroline(IX)

A suspension of 117 mg (0.2 mmol) of diketone (IV) and 60 mg (0.49 mmol) of 2-aminopyridine-3-carboxaldehyde is stirred under $N_2$ and heated under reflux as 0.01 mL of 15% methanolic KOH solution is added. The reaction mixture is heated under reflux an additional 20 hr., then cooled to room temperature and filtered. The precipitate is recrystallized by slow evaporation of a solution in dichloromethane/ethanol to yield 67.2 mg (44%) of crystalline product.

J.
2-Amino-7-n-butyl-11-oxo-5,6,8,9,10,11-hexahydrobenzo[b][1,10]phenanthroline-3-carboxaldehyde (XXXI)

A solution of 0.46 g (1 mmol) of 2-amino-11-benzylidene-7-n-butyl-5,6,8,9,10,11-hexahydrobenzo[b][1,10]-phenanthroline-3-carboxaldehyde HCl salt (XX) in 40 mL of dichloromethane and 20 mL of methanol is stirred at approximately −78° C. and ozone is bubbled through the orangish-yellow solution. When the color of the reaction mixture changes to pale greenish-yellow, the solution is immediately purged by bubbling in $N_2$ for 5 minutes. Dimethylsulfide (1.0 mL) is added and the reaction mixture is allowed to warm to room temperature. The solvents are removed by rotary evaporation and the residue is triturated with 100 mL of ether, yielding 0.39 g (100%) of product.

K. Torand (IXe)

A solution of 0.39 g of 2-amino-7-n-butyl-11-oxo-5,6,8,9,10,11-hexahydrobenzo-[b][1,10]-phenanthroline-3-carboxaldehyde(XXI) in 50 mL of ethanol is added by syringe pump over 2 hr. to a rapidly stirred solution of 0.15 mL of 50% aq. CsOH in 50 mL of ethanol, which is heated at reflux under $N_2$. The reaction mixture is heated under reflux for an additional 22 hr., then cooled to room temperature. The solvent is removed by rotary evaporation and 5 ml of $CHCL_3$ is added to the residue. The mixture is cooled overnight in a refrigerator, then filtered to collect 0.20 g (55%) of torand IXe, which may be further purified by recrystallization from 95% a8. ethanol.

L. urea complex of Diketone IV (Compound IVa)

Method 1:

A solution of 22.2 mg (0.04 mmol) of compound IV in 2 ml of CHCl$_3$ or CDCl is shaken in a tightly stoppered centrifuge tube with a solution of 0.24 g (4 mmol) of urea in 2 ml of water or D$_2$O for 1–16 hours at room temperature. At least 0.95 equivalents of urea are extracted into the organic layer, as determined by NMR, gravimetric or colorimetric analysis.

Method 2:

A solution of 118 mg (0.20 mmol) of compound IV in 10 ml of methylene chloride is mixed with a solution of 12 mg (0.20 mmol) of urea in 5 ml of methanol. Removal of solvents by rotary evaporation and recrystallization from ethanol gave the 1:1 complex as a fine yellow powder.

M. Complex of Compound IX with Guanidinium Chloride (Compound (IXa)

A suspension of 585 mg (1 mmol) of diketone (IV) and 300 mg (2.5 mmol) of 2-aminopyridine-3-carboxaldehyde is stirred under N$_2$ and heated under reflux as 0.05 mL of 15% methanolic KOH solution is added. The reaction mixture is heated under reflux an additional 48 hr., then cooled to room temperature. Guanidinium chloride (600 mg, 6.3 mmol) is added and the mixture is heated under reflux for one hr., m then cooled to room temperature. Vacuum filtration gives 642 mg (75%) of yellow solid, proven to be 1:1 complex IXa by $^1$H NMR spectroscopy of a solution in CDCl$_3$/DMSO-d$_6$.

N. Complex of Diketone (IV) with Pentamidine Isethionate

A suspension of 5.8 mg (0.01 mmol) of compound IV in 1 mL of CDCl$_3$ is shaken in a tightly stoppered centrifuge tube with 1 mL of 0.01M aq. pentamidine isethionate for 1 hr. at room temperature. The layers are separated and the CDCl$_3$ layer is observed to contain a 2:1 ratio of compound IV and pentamidine isethionate, according to $^1$H NMR spectroscopy.

O. α,α'-Dioxyphthalamido-meta-xylene(XXXII)

To a 100 mL round bottomed flask with side arm equipped with a septa, stir bar, condenser, and N$_2$ inlet were added 2.93 g (11.1 mmol) α,α'-Dibromo-meta-xylene, 3.68 g (22.6 mmol) N-Hydroxyphthalimide and 60 mL of CH$_3$CN. The system was flushed with N$_2$ then heated to reflux and 3.5 mL of Triethylamine was added via syringe. Heating was continued under N$_2$ for 15 h. then the mixture was allowed to cool to room temperature and finally in an ice bath for 30 min. Vacuum filtration and washing with cold CH$_3$CN (3×30 mL) yielded 3.17 g (66%) α,α'-Dioxyphthalamide-meta-xylene after drying at room temperature and 0.3 mm Hg pressure for 3 h. mp=222°-224° C. $^1$HNMR (CDCl$_3$ δ7.26 ppm) δ7.82-7.71 (m, phthal.—ArH, 8H); 7.67 (bs,ArH,1H); 7.59 (dd,J$^3$=8, 1 Hz, ArH,2H); 7.43 (t,J$^3$=8 Hz, ArH, 1H) ppm. $^{13}$CNMR(CDCl$_3$, δ77.00 ppm): δ163.41, 134.72, 134.41, 130.99, 130.68, 128.86, 123.51, 79.48 ppm. IR (KBr): 1785(w), 1728(s), 1465(w), 1388(M), 1185(m), 1134(m), 1082(w), 976(m), 798(w), 788(w), 700(s), 519(w)cm$^{-1}$. MS m/z (relative intensity): 429(M$^+$,18), 367(100), 272(20), 266(30), Anal. Calc'd. for C$_{24}$H$_{16}$N$_2$O$_6$: C,67.29%; H,3.76%; N,6.54%. Found: C,66.99%; H,367%; N,6.48%.

P. α,α'-Dioxyamino-meta-xylene dihydrochloride(XXXIII)

To a 100 mL round bottomed flask equipped with a side arm, septa, stir bar, condenser and N$_2$ inlet were added 0.754 g (1.76 mmol) of α,α'-Dioxyphthalamido-meta-xylene and 35 mL absolute EtOH. The system was flushed with N$_2$ then brought to reflux and 0.12 mL (0.12 g, 3.84 mmol) of anhydrous Hydrazine was added via syringe. Heating was continued for 23 h. and the system was allowed to cool to room temperature and finally in an ice bath for 1 h. The byproduct was filtered and to the filtrate was added 1.0 mL of concentrated HCl then placed in an ice bath for 1 h. Vacuum filtration and washing with 4 mL of cold EtOH afforded 0.365 g (86%) of product as a white solid after drying at 0.5 mm Hg pressure and room temperature for 5 h. The crude product is suitable for use in the next step without further purification, mp=228°-230° C. $^1$H-NMR (DMSO-d$^6$, δ2.49 2.49 ppm) δ11.25 (bs, 2×NH$_3$+, 6H), 7.45 (bs, ArH, 4H), 5.08 (s,2×ArCH$_2$, 4H). $^{13}$C-NMR (DMSO-d$^6$, δ39.7 ppm) δ134.30, 129.99, 129.90, 129.10, 75.45.

Q. Macrocyclic receptor (XXIII)

To a 100 mL round bottomed flask equipped with a side arm, septa and N$_2$ inlet were added 0.095 g (0.162 mmol) of 5,12-Di-n-butyl-3,4,7,10,11,13,14,15-octahydrobenzo[b]benzo[8,9][1,10]phenanthrolino[3,2-j][1,10]phenanthroline-1,16(2H,6H)-dione and 40 mL of absolute EtOH. The mixture was stirred for 30 min. until the solid dissolved then 0.042 g (0.174 mmol) of α,α'-Bis dioxyamino meta-xylene dihydrochloride was added in one portion and the system was flushed with N$_2$. Stirring was continued under N$_2$ for 4.5 h. and the solvent was removed by rotary evaporation. The crude product was dissolved in 45 mL CHCl$_3$ and washed with double distilled H$_2$O (3×40 mL). The CHCl$_3$ was removed by rotary evaporation and the product dissolved in a minimum amount of CH$_2$Cl$_2$ which was run on a short column of basic alumina (2.0 g, 80–200 mesh) with EtOH as eluent. The EtOH was removed by rotary evaporation and the crude solid was recrystallized by slow evaporation from CH$_2$Cl$_2$/isopropanol to give 0.057 g (49%) of product after drying at room temperature and 0.5 mm Hg pressure for 24 h. (mp>250° C.) $^1$H-NMR (CDCl$_3$,δ7.26 ppm) δ8.27 (bs, 1H), 7.85 (s,2H), 7.33 (s,3H), 5.54 (s,4H), 3.14–3.03 (m, 8H), 2.93 (t,4H), 2.81 (t,4H), 2.70 (t,4H) 1.94 (m,4H), 1.44 (m,8H), 0.97 (t,6H), IR (KBr) 9253(s), 2829(s), 2867(s), 1955(w), 1610(m), 1542(m), 1448(m), 1375(m), 1240(w), 1160(w), 1011(s), 862 (m). Anal. Calcd for C$_{46}$H$_{48}$N$_6$O$_2$2.5H$_2$O: C,72.51%; H,7.01%; N, 11.03%. Found: C,72.91%; H,6.75%; N,10.95%.

R. 2-Amino-12-benzylidene-8-n-butyl-3-cyano-6,7,9,10,11,12-hexahydrobenzo[b]pyrido[2,3-j][1,10]phenanthroline.(XXXIV)

To a 100 mL round-bottomed flask equipped with a stir bar, reflux condenser and N$_2$ inlet were added 1.0 g (2.0 mmol) of 2-amino-11-benzylidine-7-n-butyl-5,6,8,9,10,11 hexahydrobenzo[b][1,10]phenanthroline 3-aldehyde HCl salt, 0.144 g (2.0 mmol) of malononitrile, 0.2 mL piperidine and 12 mL absolute EtOH. The system was flushed with N2 then heated at reflux for 1.5 h. The mixture was cooled to room temperature and finally in an ice bath for 1 h. Vacuum filtration and washing with 5 mL cold EtOH yielded 0.81 g (79%) 2-amino-12benzylidine-8-n-butyl-6,7,9,10,11,12 hexahydrobenzo[b]pyrido[2,3-j][1,10]phenanthroline after drying at room temperature and 0.4 mmHg pressure for 2 h. If the crude product is not sufficiently pure it may be recrystallized with absolute EtOH. (mp=261°–263° C. DEC.)

$^1$H-NMR (CDCL$_3$,7.26 ppm) δ8.34 (s,C$^5$H,1H), 8.22(s,C$^3$H,1H), 7.80(s,ArCH,1H), 7.47–7.22(m,ArH,5H), 5.73(bs,NH$_2$,2H), 3.08–3.01(m,Pyr-CH$_2$-CH$_2$-Naph,4H), 2.70(t,J$^3$=6 Hz,C$^8$-CH$_2$-Prop,2H), 1.88(m,C$^{10}$H$_2$,2H), 1.48(m,C$^8$-CH$_2$-CH$_2$-CH$_2$-CH$_3$,4H), 1.00 (T,J$^3$=7 Hz,CH$_3$,3H).

$^{13}$H-NMR (CDCL$_3$, 77.0 ppm) δ158.74, 157.37, 156.93, 152.31, 147.97, 147.27, 143.51, 138.30, 135.70, 134.40, 132.64, 132.41, 129.93, 129.85, 128.14, 127.75, 126.30, 116.10, 115.54, 95.46, 31.03, 28.20, 27.63, 27.55, 26.71, 23.89, 23.13, 22.80, 13.86.

IR (KBr) 3395(w), 3300(m), 3181(w), 2956(m), 2932(m), 2861(w), 2206(m), 1611(s), 1563(m), 1439(m), 1213(w), 1082(m), 804(m), 696(m).

S.

2-Amino-8-n-butyl-3-cyano-6,7,10,11tetrahydrobenzo[b]pyrido[2,3-j][1,10]phenanthroline-12(9H)-one (XXVII)

To a 250 mL round bottomed flask were added 0.305 g (0.147 mmol) of crude 2-amino-12-benzylidene-8-n-butyl-3-cyano-6,7,9,10,11,12hexahydrobenzo[b]pyrido[2,3-j][1,10]phenanthroline, 40 mL of CH$_2$CL$_2$ and 115 mL of CH$_3$OH. The solution was cooled to approximately −78° C. by means of a dry ice/acetone bath and N$_2$ was passed through the solution for 5 min. A stream of O$_3$ was passed through the solution until the color turned from dark orange-brown to dark green-brown. N$_2$ was passed through the solution for an additional 5 min. then 0.6 mL of dimethyl sulfide was added via syringe. The solution was allowed to warm to room temperature overnight and the solvents removed by rotary evaporation. The crude product was washed with ether (3×50 mL) then recrystallized from CHCL$_3$/EtOH. Vacuum filtration gave 0.09 g (35%) of product as a yellow solid after drying at 0.5 mm Hg pressure and 61° C. for 48 hr. (mp>300° C.).

$^1$H-NMR (DMSO-d$^6$,2.49 ppm) δ8.71 (s,C$^4$H, 1H), 8.05 (s,C$^5$H, 1H), 7.18 (bs,NH$_2$, 2H), 3.07–3.02 (m,Pyr-CH$_2$-Naph, C$^{11}$H,6H), 2.77–2.68 (m,C$^8$-CH$_2$-Prop,C$^9$H$_2$,4H), 2.12 (m,C$^{10}$H$_2$,2H), 1.47 (m,C$^8$-CH$_2$-CH$_2$-CH$_3$,4H), 0.95 (t,J$^3$=5 Hz,CH$_3$,3H).

IR(KBr) 3406(w), 2952(w), 2215(w), 1627(s), 1610(s), 1559(s), 1541(w), 1507(m), 1434(m), 1221(m), 1178(m), 802(m).

NOTES FOR EXAMPLES

1. Cyclohexane (99%) was obtained from Lancaster Synthesis and was used without purification.

2. Potassium hydroxide (86.6%) was certified grade from Fisher Scientific.

3. Valeraldehyde (bp 98°–100° C.) was obtained from Aldrich Chemical Company, distilled under a static atmosphere of nitrogen and stored at −26° C.

4. Additional product may be isolated from the combined filtrates, which are concentrated to approximately 200 mL using a rotary evaporator. The white solid is collected by vacuum filtration and washed with water (2×200 mL) and cold ether (200 mL), then recrystallized from methanol and dried to give 84 g (23%), mp 140°–141° C.

5. The product has the following spectroscopic properties: $^1$H NMR (CDCl$_3$) δ: 0.88 (t, 3H, CH$_3$), 1.1–2.3 (m, 23H, CH$_2$, CH), 2.4 (m, 1H, CH$_2$), 2.6 (s, 1H, OH); IR (KBr)cm$^{-1}$: 3400(s), 2920(s), 2850(s), 1705(s), 1450(m), 1410(m), 1350(m), 1290(m), 1270(m), 1210(m), 1145(m), 970(m), 935(m); mass spectrum, m/z (relative abundance, 70 eV): 264 (M$^+$, 10%), 167 (85%), 166 (100%). A second recrystallization from methanol gave a sample for microanalysis. Anal. Calcd for C$_{17}$H$_{28}$O$_2$: C, 77.22; H, 10.67. Found: C, 77.34: H, 10.51%.

6. The condenser is fitted to the side-arm of the Claisen adapter.

7. Approximately 470 mL of 33.3% (w/w) aqueous sodium hydroxide was required to reach a final pH of 8–9. Lower pH leads to extraction of acetic acid, whereas higher pH (10) causes the formation of a white precipitate that makes phase separation difficult during extraction.

8. The product has the following spectroscopic properties: $^1$HNMR (CDCl$_3$) δ:0.96 (t, J=6 Hz, 3H, CH$_3$), 1.3–1.5 (m, 4H CH$_2$-CH$_2$-CH$_3$), 1.7–1.9 (m, 8H, H2, H3, H6, H7), 2.5–2.9 (m, 10H, Ar-CH$_2$); IR (neat) cm$^{-1}$: 2930(s), 2860(s), 1560(m), 1435(m), 1410(m), 1240(w); mass spectrum, m/z (relative abundance, 70 eV): 243 (M$^+$, 51%), 228 (6%), 214 (16%), 201 (64%), 200 (56%), 186 (100%). An analytical sample was obtained by bulb-to-bulb distillation (1 mm). Anal. Calcd for C$_{17}$H$_{25}$N: C, 83.89; H, 10.35; N 5.75. Found: C. 83.58; 10.07; N, 5.40%.

9. Oxone, the DuPont trade name for potassium peroxymonosulfate, has the composition 2KHSO$_5$ KHSO$_4$ K$_2$SO$_4$ and was supplied by Aldrich Chemical Company.

10. Oxidation may be monitored by thin-layer chromatography (alumina, ethyl acetate; N-oxide R$_f$0.2–0.3). Trace amounts of unreacted 9-n-butyl-1,2,3,4,5,6,7,8-octahydroacridine (R$_f$0.7) do not effect subsequent product yields, but reaction time may be extended to effect complete conversion.

11. The crude product is sufficiently pure to be used directly in part D, but may be purified by recrystallization from ethyl acetate/hexanes, mp 98°–99° C.; $^1$HNMR (CDCl$_3$) δ: 0.96 (t, J=6 Hz, 3H, CH$_3$), 1.41 (m, 4H, CH$_2$-CH$_2$-CH$_3$), 1.7–1.9 (m, 8H, H2, H3, H6, H7), 2.50 (m, 2H, 9-CH$_2$), 2.68 (m, 4H, H1, H8), 2.96 (m, 4H, H4, H5).

12. MCPBA was technical grade (80–85%) supplied by Aldrich Chemical Co. or Lancaster Synthesis Ltd.

REACTIONS
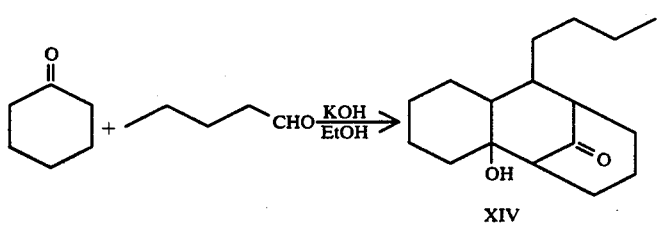
(1)
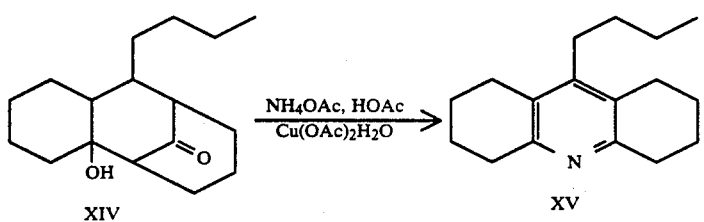
(2)
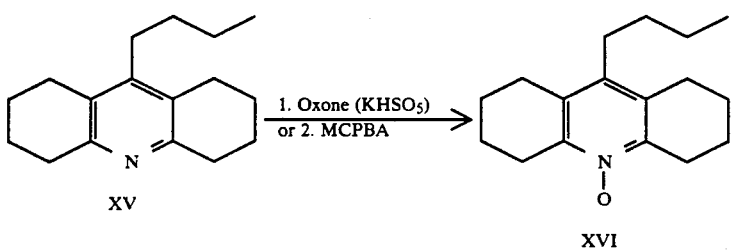
(3)
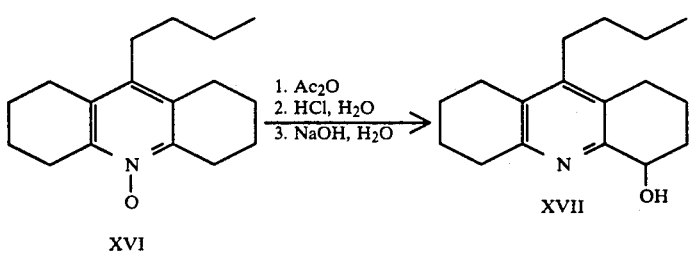
(4)
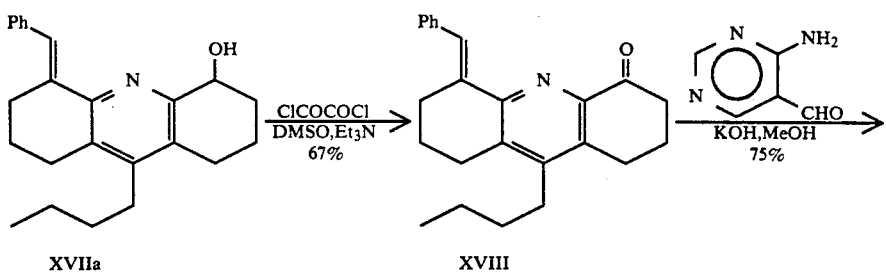
(5)
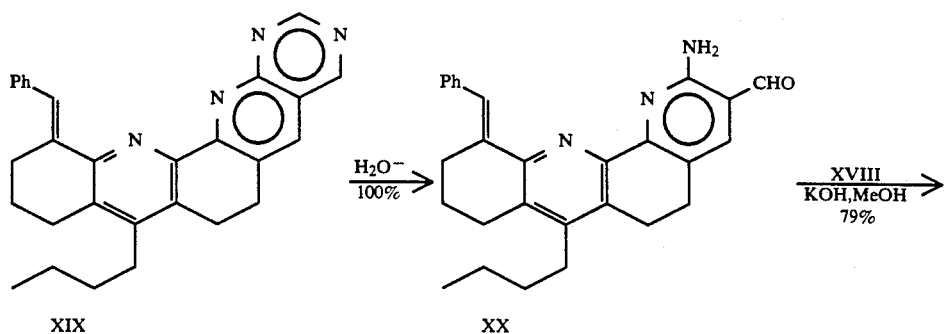

-continued
REACTIONS
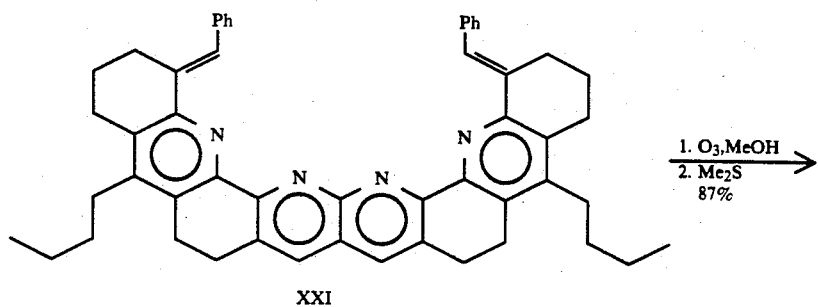
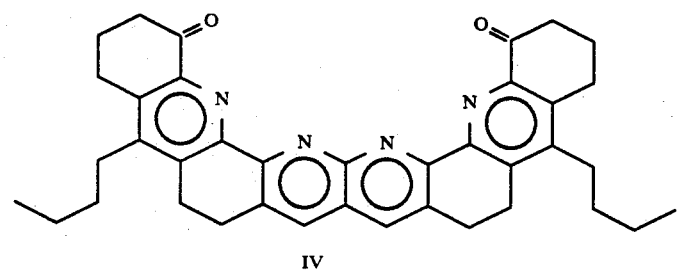
(6)
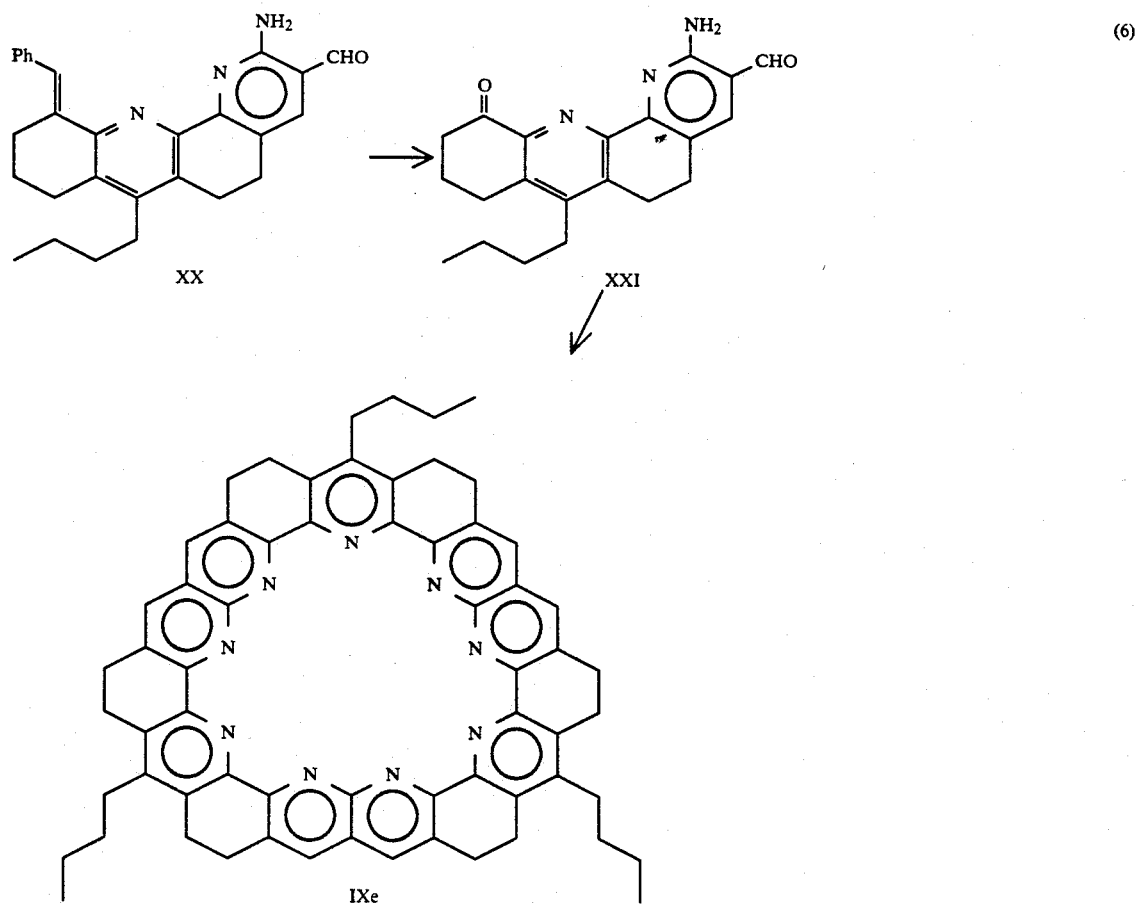

-continued
REACTIONS
(7)
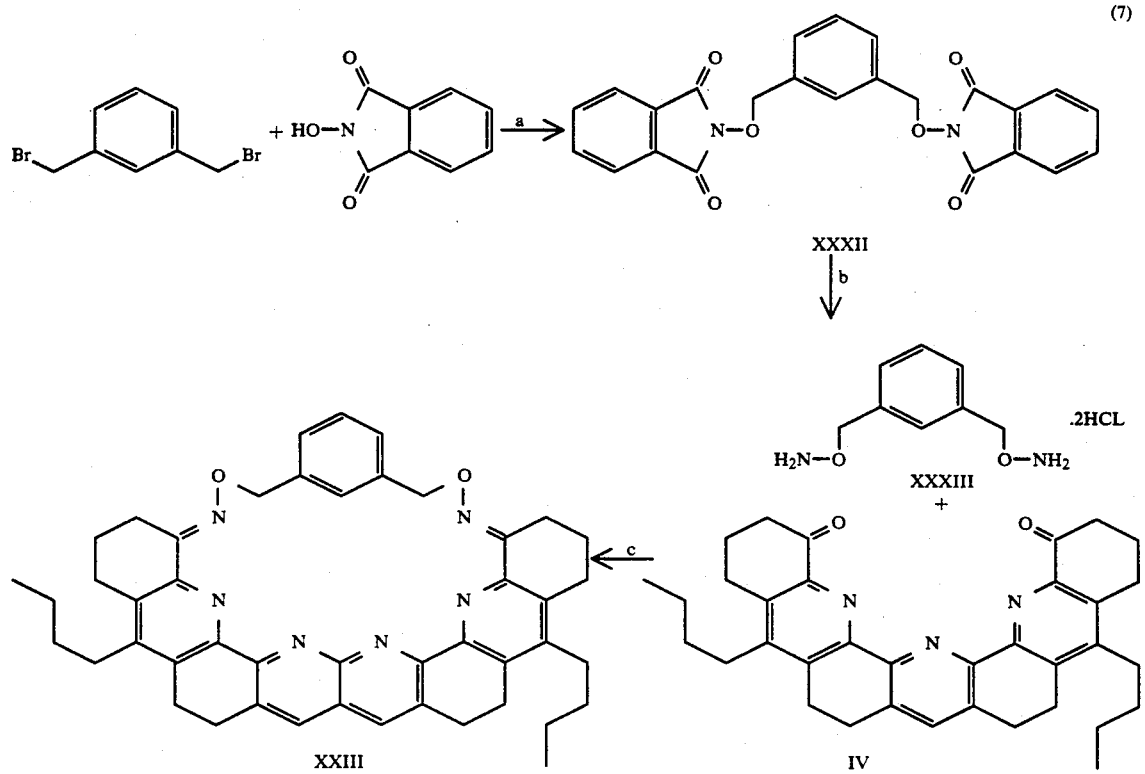
Synthesis of macrocyclic receptor XXIII: (a) Et₃N, CH₃CN, reflux (66%); (b) H₂NNH₂, EtOH, reflux, HCl(86%); (c) EtOH, room temp. (49%).
(8)
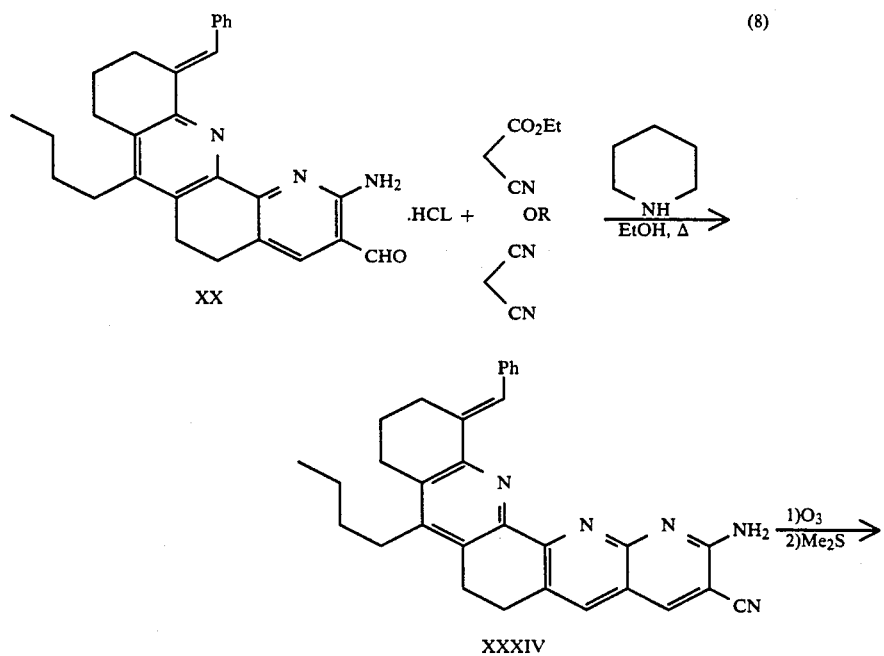

-continued

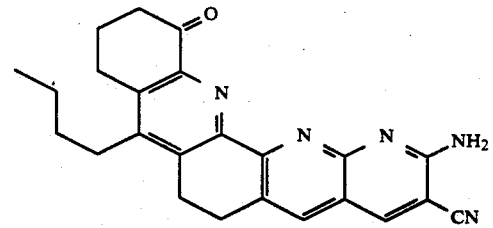

XXVII

What is claimed is:

1. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

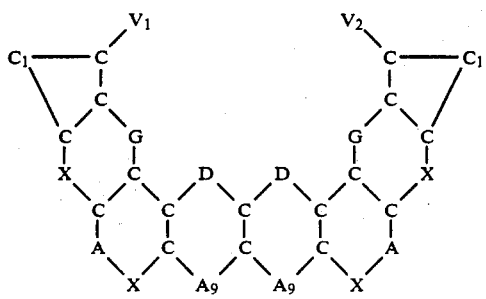

wherein
C represents carbon atoms;
D independently represents nitrogen or oxygen atoms;
X independently represents (A)m;
A and G independently represent carbon, sulfur, nitrogen or oxygen atoms;
m=0-5;
s=1-7;
p and q independently represent 0-2;
$V_1$ and $V_2$ independently represent hydrogen, D or DαAr except that $V_1$ and $V_2$ are not both hydrogen and are not simultaneously hydrogen and D;
αAr is selected from the group consisting of OCH$_2$Ar, CH$_2$OAr, (CH$_2$)$_n$Ar wherein n=1-5, NCH$_2$Ar, OCOAr, CH$_2$COAr$_2$, NCOAr, SCOAr, OCH$_2$OAr, CH$_2$NAr, CO$_2$Ar, COCH$_2$Ar, CONAr, COSAr; and
wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

2. The molecule of claim 1, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

3. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

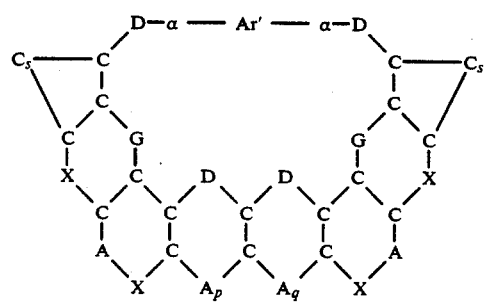

wherein
C represents carbon atoms;
D independently represents nitrogen or oxygen atoms;
X independently represents (A)m;
A and G independently represent carbon, sulfur, nitrogen or oxygen atoms;
m=0-5;
s=1-7;
p and q independently represent 0-2;
α independently represents OCH$_2$, (CH$_2$)$_n$ wherein n=1-5, NCH$_2$, OCO, CH$_2$CO, NCO, SCO, OCH$_2$O, CH$_2$N, CO$_2$, COCH$_2$, CON, COS or CH$_2$O; and
wherein Ar' is a disubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

4. The molecule of claim 3, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

5. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

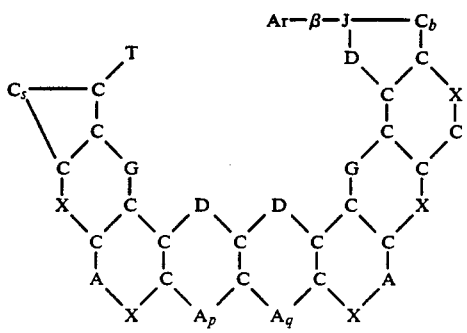

wherein
C represents carbon atoms;
D independently represents nitrogen or oxygen atoms;
X independently represents (A)m;
A and G independently represent carbon, sulfur, nitrogen or oxygen atoms;
J independently represents carbon or nitrogen;
m=0-5;
b=0-6;
s=1-7;
p and q independently represent 0-2;
T=DαAr;
wherein αAr is selected from the group consisting of $OCH_2Ar$, $CH_2OAr$, $(CH_2)_nAr$ wherein n=1-5, $NCH_2Ar$, $OCOAr$, $CH_2COAr_2$, $NCOAr$, $SCOAr$, $OCH_2OAr$, $CH_2NAr$, $CO_2Ar$, $COCH_2Ar$, $CONAr$, $COSAr$;

βAr is selected from the group consisting of $(CH_2)_d Ar$ wherein d=1-4, COAr, OAr, NAr, SAr; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

6. The molecule of claim 5, complexed with a guest analyte molecule selected from the group consisting of urea, thiourea, guanidine, guanidine monosubstituted on one nitrogen atom, guanidine disubstituted on one nitrogen atom, creatinine, arginine compounds, or amidine compounds or an addition salt of the guest analyte molecule.

7. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

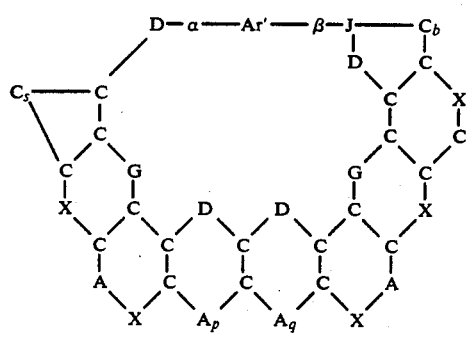

wherein
C represents carbon atoms;
D independently represents nitrogen or oxygen atoms;
X independently represents (A)m;
A and G independently represent carbon, sulfur, nitrogen or oxygen atoms;
J independently represents carbon or nitrogen;
m=0-5;
b=0-6;
s=1-7;
p and q independently represent 0-2;
α independently represents $OCH_2$, $(CH_2)_n$ wherein n=1-5, $COCH_2$, $NCH_2$, $OCO$, $CH_2O$, $CH_2CO$, $NCO$, $SCO$, $OCH_2O$, $CH_2N$, $CO_2$, $CON$ or $COS$;
β independently represents $(CH_2)_d$ wherein d=1-4, CO, O, N or S; and
wherein Ar' is a disubstituted aromatic group selected from the group consisting of benzene, naphthalene, phenanthrene, anthracene, pyrene, benzpyrene, naphthacene, pyridine, guinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-guinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

8. The molecule of claim 7, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

9. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

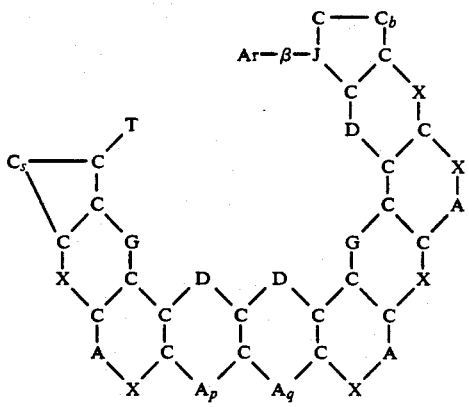
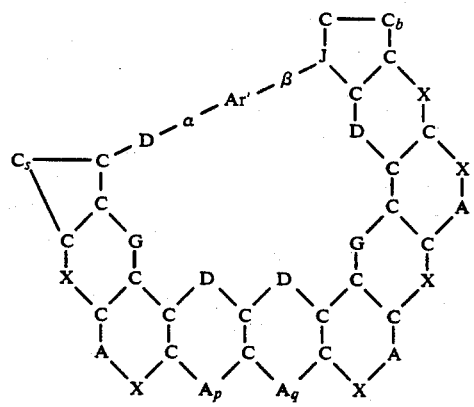

wherein

C represents carbon atoms;
D independently represents nitrogen or oxygen atoms;
X independently represents (A)m;
A and G independently represent carbon, sulfur, nitrogen or oxygen atoms;
J independently represents carbon or nitrogen;
m=0-5;
b=0-6;
s=1-7;
p and q independently represent 0-2;
T=DαAr;
wherein αAr is selected from the group consisting of: $OCH_2Ar$, $(CH_2)n$ AR wherein n=1-5, $NCH_2Ar$, OCOAr, $CH_2OAr$, $CH_2COAr_2$, NCOAr, SCOAr, $OCH_2OAr$, $CH_2NAr$, $CO_2Ar$, $COCH_2Ar$, CONAr, COSAr;
βAr is selected from the group consisting of $CH_2Ar$, $(CH_2)_dAr$ wherein d=1-4, COAr, OAr, NAr, SAr; and
wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

10. The molecule of claim 9, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

11. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

wherein

C represents carbon atoms;
D independently represents nitrogen or oxygen atoms;
X independently represents (A)m;
A and G independently represent carbon, sulfur, nitrogen or oxygen atoms;
J independently represents carbon or nitrogen;
m=0-5;
b=0-6;
s=1-7;
p and q independently represent 0-2;
α independently represents $OCH_2$, $(CH_2)_n$ wherein n=1-5 $NCH_2$, OCO, $CH_2CO$, NCO, SCO, $OCH_2O$, $CH_2N$, $CO_2$, $COCH_2$, CON, $CH_2O$ or COS;
β independently represents $(CH_2)_d$ wherein d=1-4, CO, O, N or S; and
wherein Ar' is a disubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

12. The molecule of claim 11, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

13. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

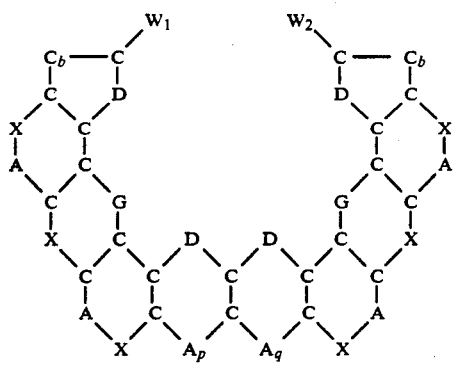

wherein

C represents carbon atoms;

D independently represents nitrogen or oxygen atoms;

X independently represents (A)m;

A and G independently represent carbon, sulfur, nitrogen or oxygen atoms;

m=0–5;

b=0–6;

p and q independently represent 0–2;

$W_1$ and $W_2$ independently represent hydrogen, nitrogen, oxygen or βAr; except that $W_1$ and $W_2$ are not both hydrogen, nitrogen, and oxygen; and at least one of $W_1$ and $W_2$ is βAr;

wherein βAr is selected from the group consisting of $(CH_2)_d$Ar wherein d=1–4, COAr, OAr, NAr, SAr; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

14. The molecule of claim 13, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

15. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

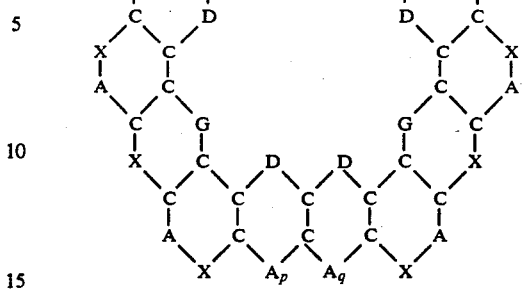

wherein

C represents carbon atoms;

D independently represents nitrogen or oxygen atoms;

X independently represents (A)m;

A and G independently represent carbon, sulfur, nitrogen or oxygen atoms;

J independently represents carbon or nitrogen;

m=0–5;

b=0–6;

p and q independently represent 0–2;

β independently represents $(CH_2)_d$ wherein d=1–4, CO, O, N or S; and wherein Ar' is a disubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

16. The molecule of claim 15, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

17. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

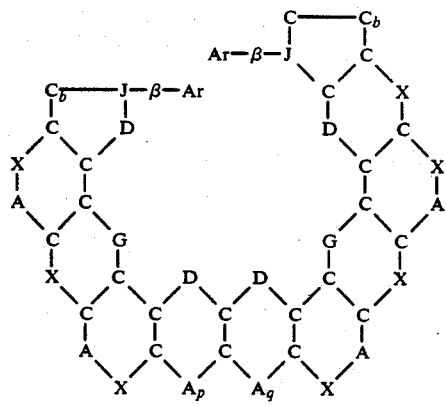
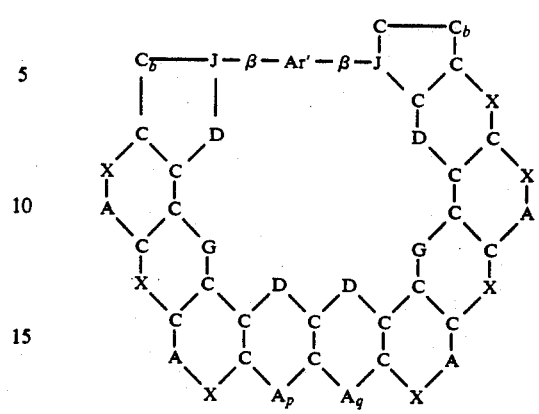

wherein

C represents carbon atoms;

D independently represents nitrogen or oxygen atoms;

X independently represents (A)m;

A and G independently represent carbon, sulfur, nitrogen or oxygen atoms;

J independently represents carbon or nitrogen;

m=0–5;

b=0–6;

p and q independently represent 0–2;

wherein βAr is selected from the group consisting of $(CH_2)_d$ Ar wherein d=1–4, COAr, OAr, NAr, SAr; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

18. The molecule of claim 17, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

19. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

wherein

C represents carbon atoms;

D independently represents nitrogen or oxygen atoms;

X independently represents (A)m;

A and G independently represent carbon, sulfur, nitrogen or oxygen atoms;

J independently represents carbon or nitrogen;

m=0–5;

b=0–6;

p and q independently represent 0–2;

β independently represents $(CH_2)_d$ wherein d=1–4, CO, O, N or S; and wherein Ar' is a disubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

20. The molecule of claim 19, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

21. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

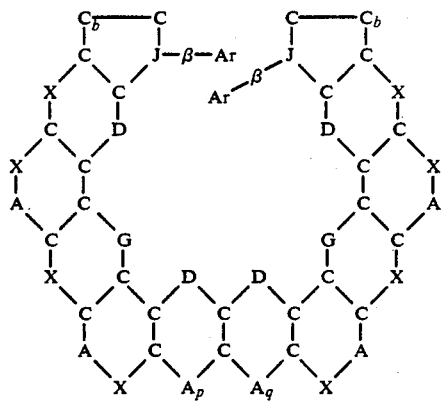

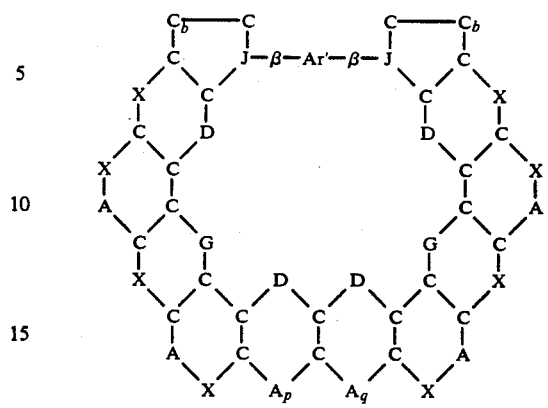

wherein

C represents carbon atoms;

D independently represents nitrogen or oxygen atoms;

X independently represents (A)m;

A and G independently represent carbon, sulfur, nitrogen or oxygen atoms;

J independently represents carbon or nitrogen;

m=0–5;

b=0–6;

p and q independently represent 0–2;

wherein $\beta$Ar is selected from the group consisting of $(CH_2)_d$Ar wherein d=1–4, COAr, OAr, NAr, SAr; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

22. The molecule of claim 21, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

23. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

wherein

C represents carbon atoms;

D independently represents nitrogen or oxygen atoms;

X independently represents (A)m;

A and G independently represent carbon, sulfur, nitrogen or oxygen atoms;

J independently represents carbon or nitrogen;

m=0–5;

b=0–6;

p and q independently represent 0–2;

$\beta$ independently represents $(CH_2)_d$ wherein d=1–4, CO, O, N or S; and wherein Ar' is a disubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

24. The molecule of claim 23, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

25. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

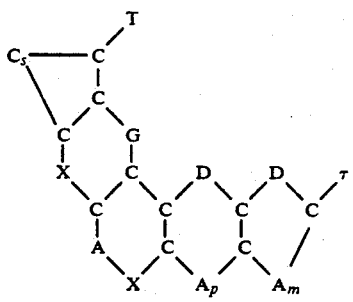

wherein

C represents carbon atoms;

D independently represents nitrogen or oxygen atoms;

X independently represents (A)m;

A and G independently represent carbon, sulfur, nitrogen or oxygen atoms;

T independently represents oxygen, nitrogen or sulfur;

m=0-5;

s=1-7;

p=0-2;

$\tau$ is selected from the group consisting of O, N, S, OH, OAr, NH$_2$, NHAr, NHCOR, NHOH, NHOR, NH$_2$, NHR, SH, SR and SAr; wherein R is an alkyl or substituted alkyl; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

26. The molecule of claim 25, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

27. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

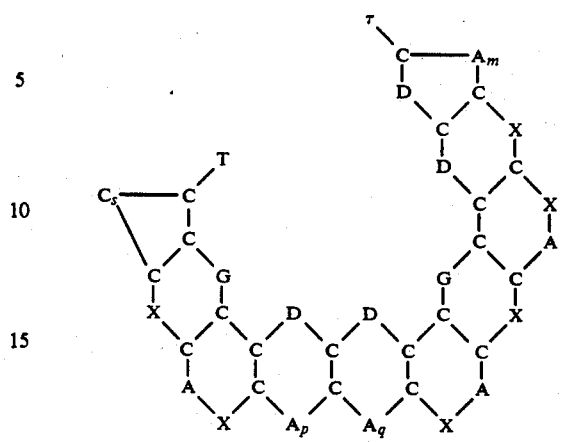

wherein

C represents carbon atoms;

D independently represents nitrogen or oxygen atoms;

X independently represents (A)m;

A and G independently represent carbon, sulfur, nitrogen or oxygen atoms;

T independently represents oxygen, nitrogen or sulfur;

m=0-5;

s=1-7;

p and q independently represent 0-2;

$\tau$ is selected from the group consisting of O, N, S, OH, OAr, NH$_2$, NHAr, NHCOR, NHOH, NHOR, NH$_2$, NHR, SH, SR and SAr; wherein R is an alkyl or substituted alkyl; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

28. The molecule of claim 27, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

29. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

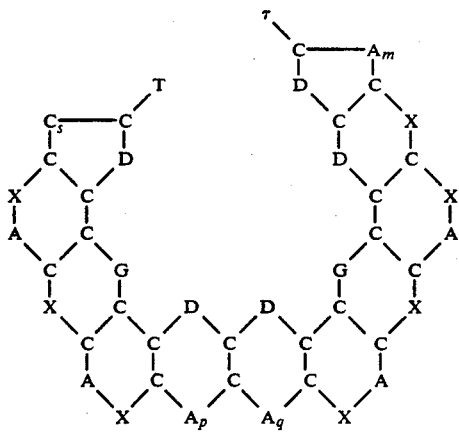

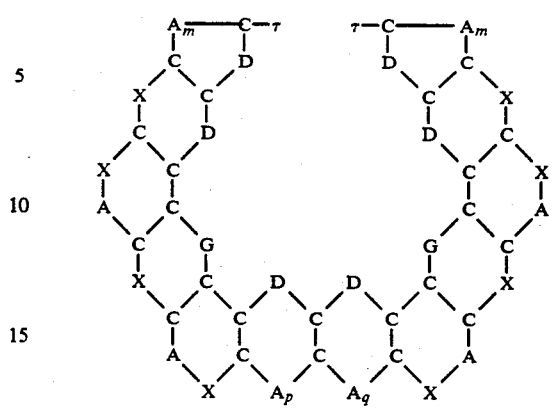

wherein

C represents carbon atoms;

D independently represents nitrogen or oxygen atoms;

X independently represents (A)m;

A and G independently represent carbon, sulfur, nitrogen or oxygen atoms;

T independently represents oxygen, nitrogen or sulfur;

m=0-5;

p and q independently represent 0-2;

τ is selected from the group consisting of O, N, S, OH, OAr, NH₂, NHAr, NHCOR, NHOH, NHOR, NH₂, NHR, SH, SR and SAr; wherein R is an alkyl or substituted alkyl; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

30. The molecule of claim 29, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

31. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

wherein

C represents carbon atoms;

D independently represents nitrogen or oxygen atoms;

X independently represents (A)m;

A and G independently represent carbon, sulfur, nitrogen or oxygen atoms;

m=0-5;

p and q independently represent 0-2;

τ is selected from the group consisting of O, N, S, OH, OAr, NH₂, NHAr, NHCOR, NHOH, NHOR, NH₂, NHR, SH, SR and SAr; wherein R is an alkyl or substituted alkyl; and wherein Ar is a monosubstituted aromatic group selected from the group consisting of benzene, naphthalene, phenanthrene, anthracene, pyrene, benzpyrene, naphthacene, pyridine, quinoline, isoquinoline, acridine, phenanthroline, pyrrole, indole, carbazole, imidazole, benzimidazole, furan, thiophene, purine, pyrimidine, 2-pyridone, 4-pyridone, 9-acridone, 2-quinolone, 4-quinolone, pyridazene, benzofuran, quinazoline, phenanthridine, anthrone, fluorene, picrylamines, azulenes, nitrophenols, quinones, azo dyes, merocyanine dyes, coumarins, fluorescein, Lucifer Yellow, 8-hydroxyquinoline, dansyl derivatives, porphyrins and phthalocyanines.

32. The molecule of claim 31, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

33. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

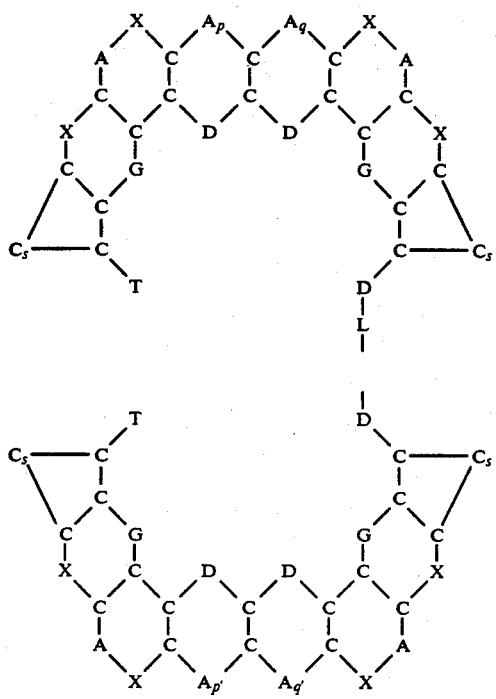

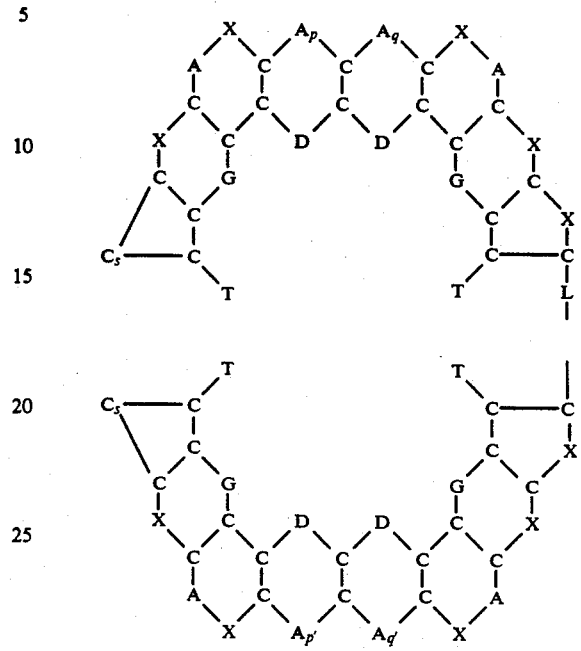

wherein
C represents carbon atoms;
D independently represents nitrogen or oxygen atoms;
X independently represents (A)m;
A and G independently represent carbon, sulfur, nitrogen or oxygen atoms;
T independently represents oxygen, nitrogen or sulfur;
s=1-7;
p, p', q and q' independently represent 0-2; and
L independently represents a hydrocarbon or heteroatom-containing group having from about 3 to about 10 members.

34. The molecule of claim 33, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

35. A molecule capable of forming stable complexes with a guest analyte molecule urea, thiourea, guanidine, guanidine monosubstituted on one nitrogen atom, guanidine disubstituted on one nitrogen atom, creatinine, arginine, amidine compounds or an addition salt of the guest analyte molecule comprising the structure:

wherein
C represents carbon atoms;
D independently represents nitrogen or oxygen atoms;
X independently represents (A)m;
A and G independently represent carbon, sulfur, nitrogen or oxygen atoms;
T independently represents oxygen, nitrogen or sulfur;
s=1-7;
p, p', q and q' independently represent 0-2; and
L independently represents a hydrocarbon or heteroatom-containing group having from about 3 to about 10 members.

36. The molecule of claim 35, complexed with a guest analyte molecule selected from the group consisting of urea, thiourea, guanidine, guanidine monosubstituted on one nitrogen atom, guanidine disubstituted on one nitrogen atom, creatinine, arginine compounds, amidine compounds or an addition salt of the guest analyte molecule.

* * * * *

UNITED STATES PATENT AND TRADEMARK OFFICE
CERTIFICATE OF CORRECTION

PATENT NO. : 5,283,333

DATED : February 1, 1994

INVENTOR(S) : Thomas W. Bell

It is certified that error appears in the above-indentified patent and that said Letters Patent is hereby corrected as shown below:

In Column 3 Line 40, Figure C     "

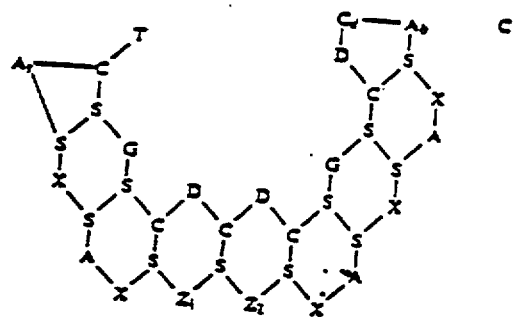

"

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

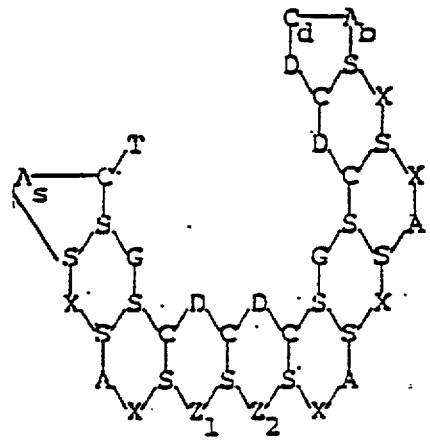

C        --;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 13, Figure IXd "

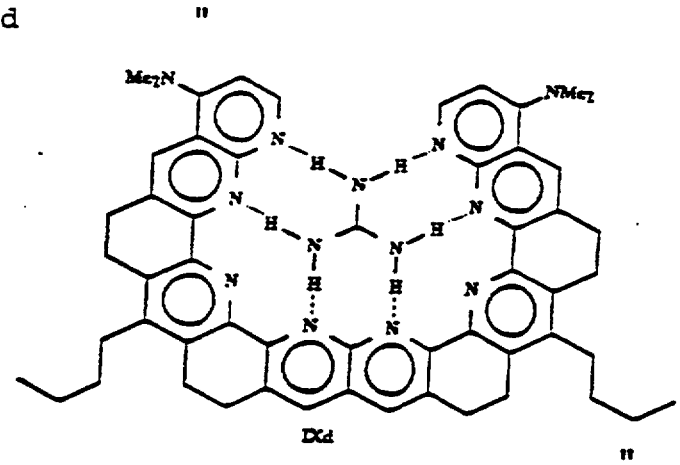

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

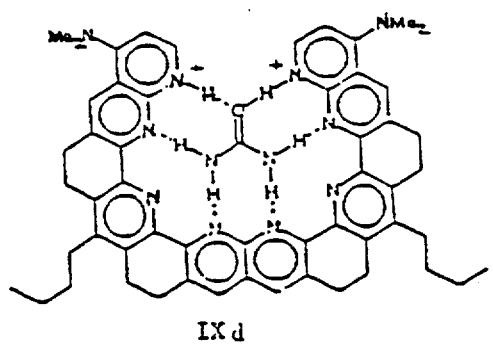

IXd

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 17, Figure XIIIc

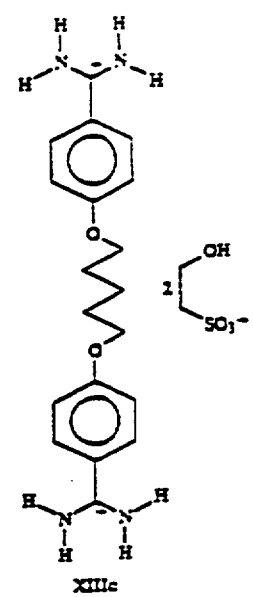

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

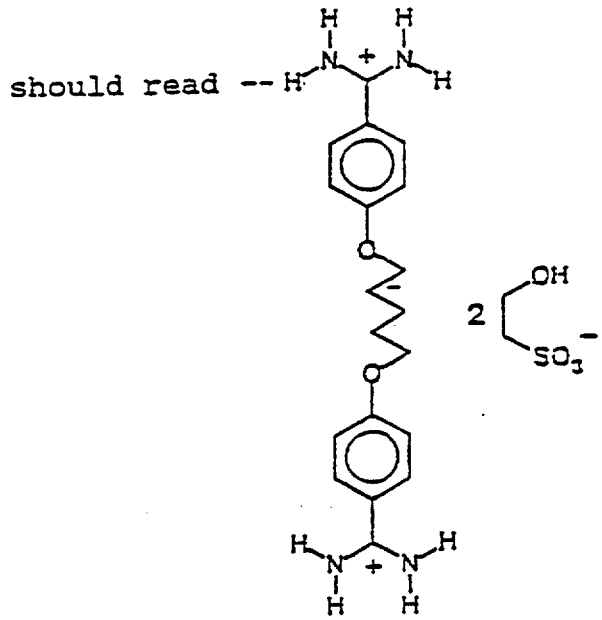

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 19, Line 29, the term "X111a and X111b" should read --XIIIa and XIIIb--;

In Column 24, Figure S

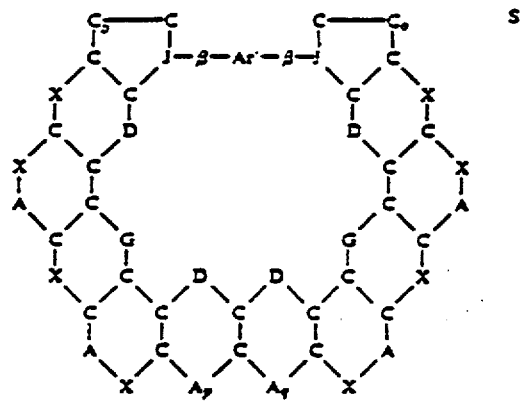

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

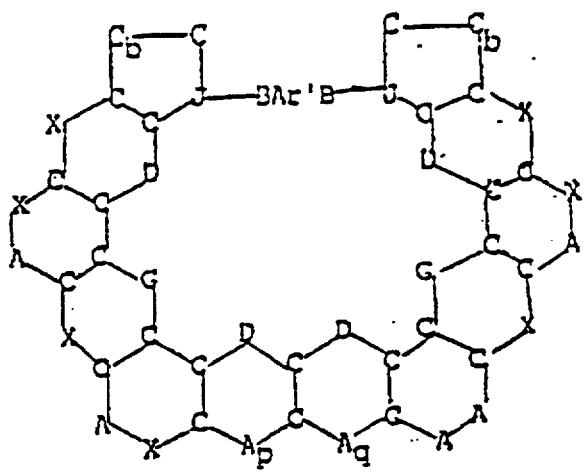

_S_ --;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 27, Figure XXIIb  "

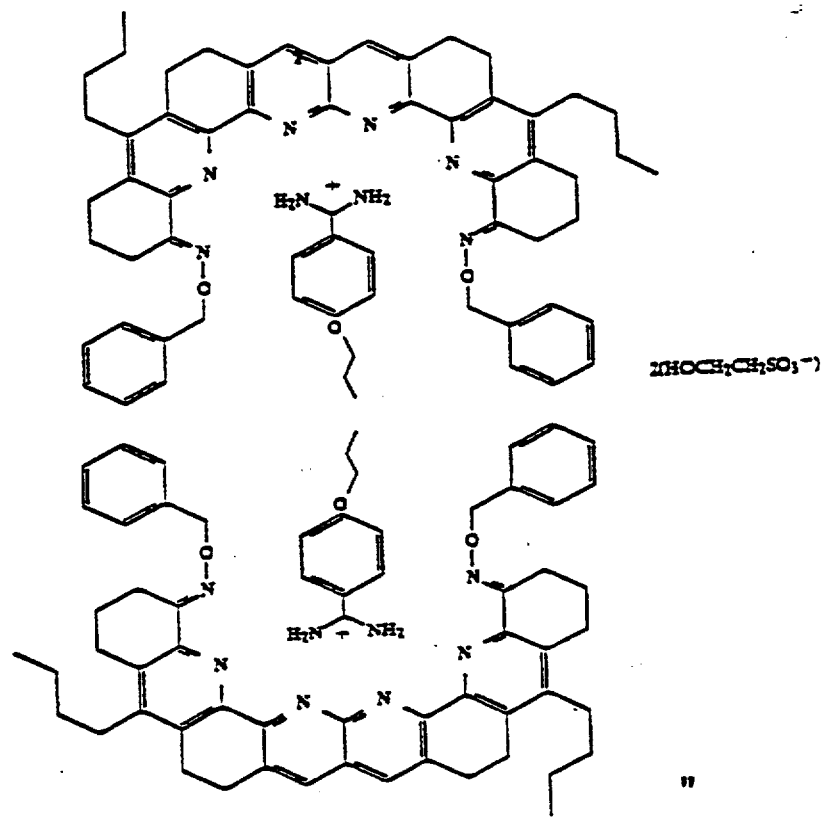

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

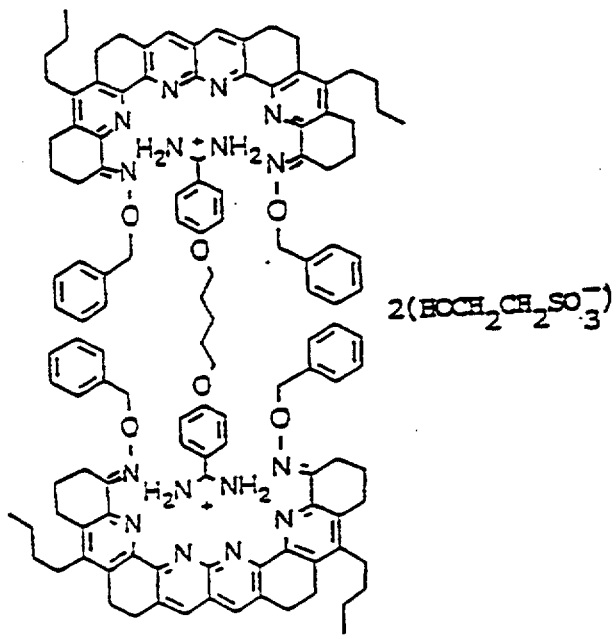

XXIIb

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 33, Line 12, the term "heter-carbon" should read --heterocarbon--;

Line 30, Figure U

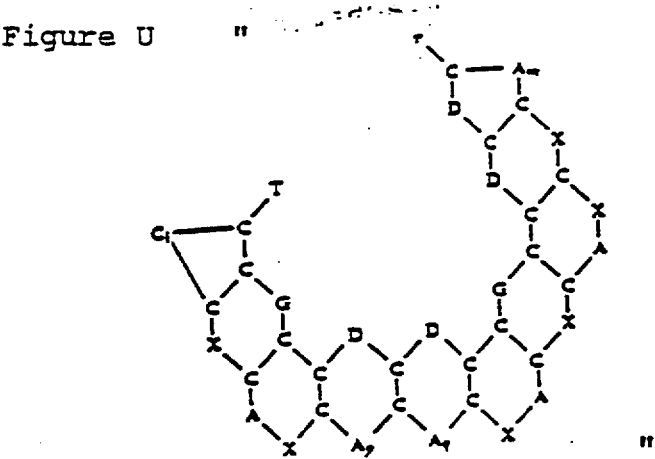

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

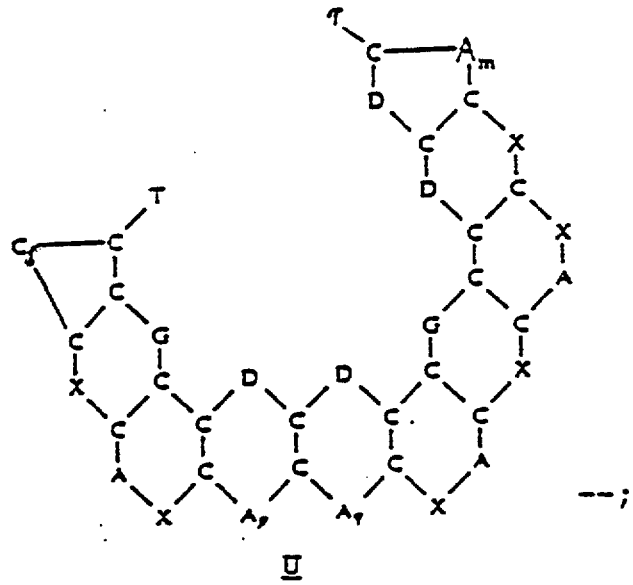

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

Line 50, Figure V   "

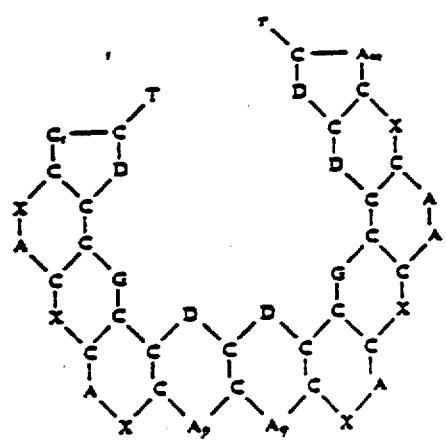

"

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

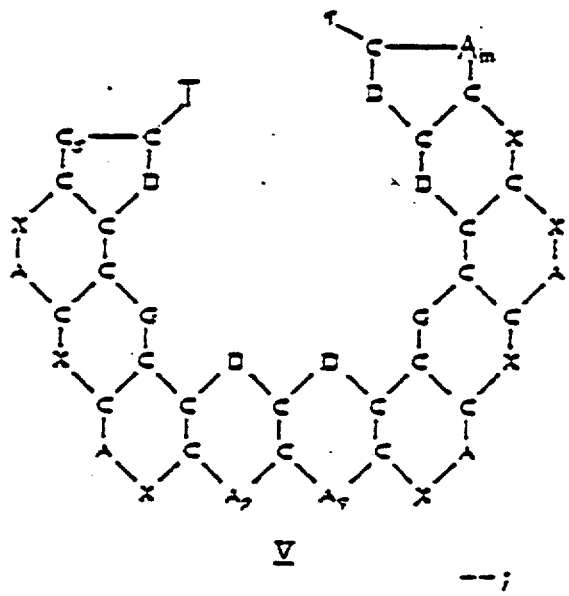

--;

// UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 34, Line 25, Figure X    "

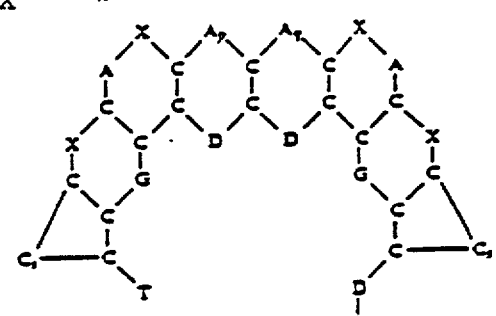

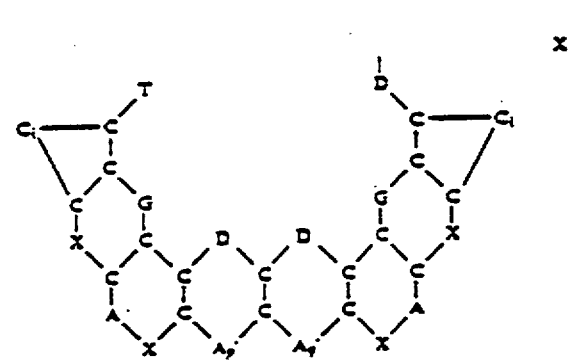

"

16T
UNITED STATES PATENT AND TRADEMARK OFFICE
CERTIFICATE OF CORRECTION

PATENT NO. : 5,283,333

DATED : February 1, 1994

INVENTOR(S) : Thomas W. Bell

It is certified that error appears in the above-indentified patent and that said Letters Patent is hereby corrected as shown below:

should read --

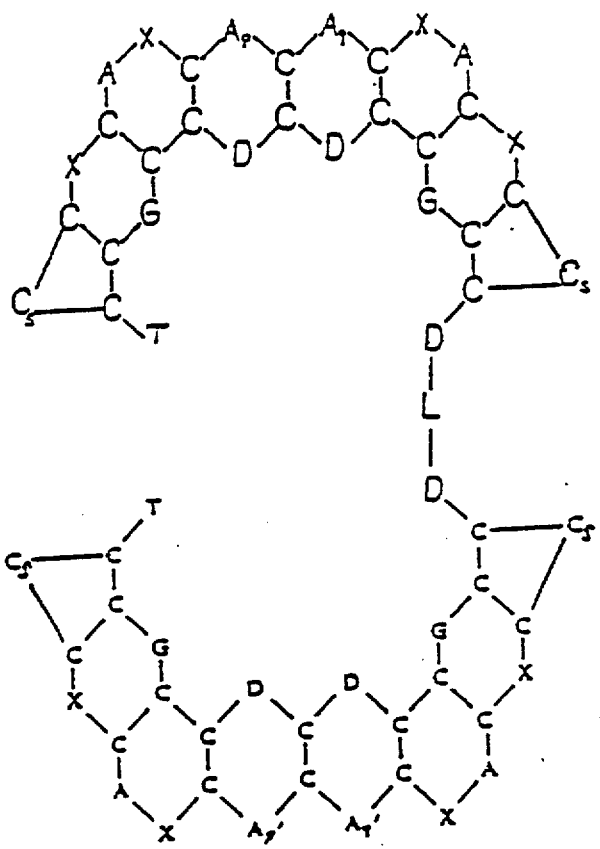

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 34, Line 56 to column 35, line 13, Figure Y

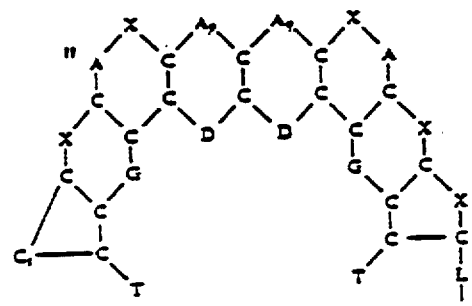

-continued

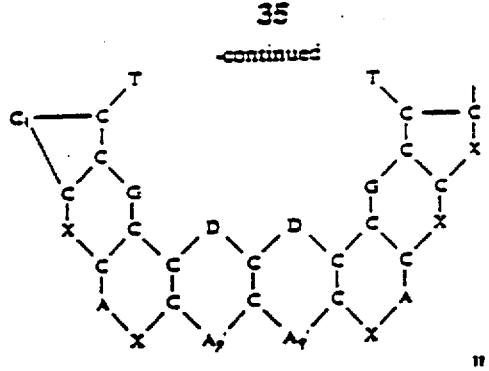

Y

UNITED STATES PATENT AND TRADEMARK OFFICE
CERTIFICATE OF CORRECTION

PATENT NO. : 5,283,333

DATED : February 1, 1994

INVENTOR(S) : Thomas W. Bell

It is certified that error appears in the above-indentified patent and that said Letters Patent is hereby corrected as shown below:

should read --

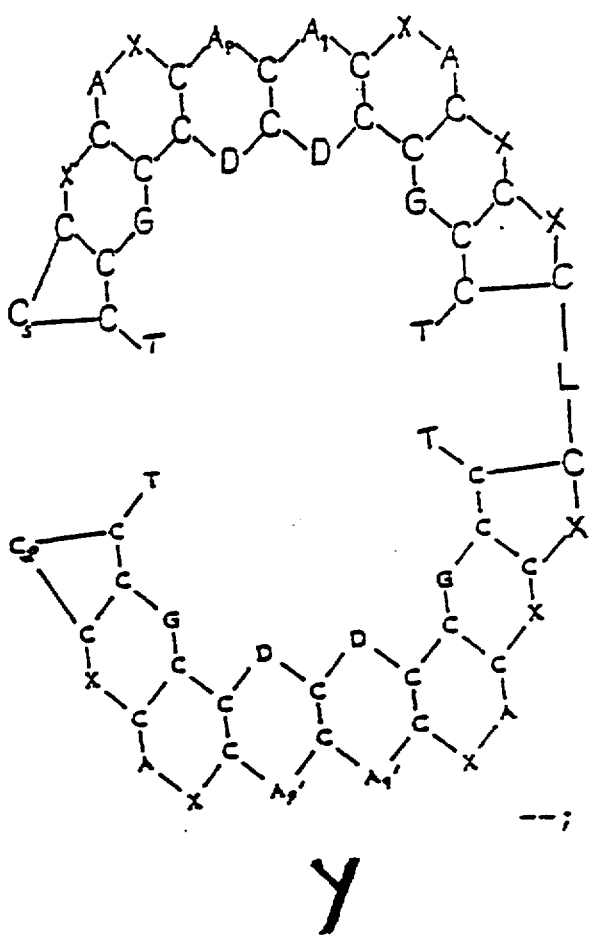

--;

UNITED STATES PATENT AND TRADEMARK OFFICE
CERTIFICATE OF CORRECTION

PATENT NO. : 5,283,333

DATED : February 1, 1994

INVENTOR(S) : Thomas W. Bell

It is certified that error appears in the above-indentified patent and that said Letters Patent is hereby corrected as shown below:

In Column 37, Figure XXVa

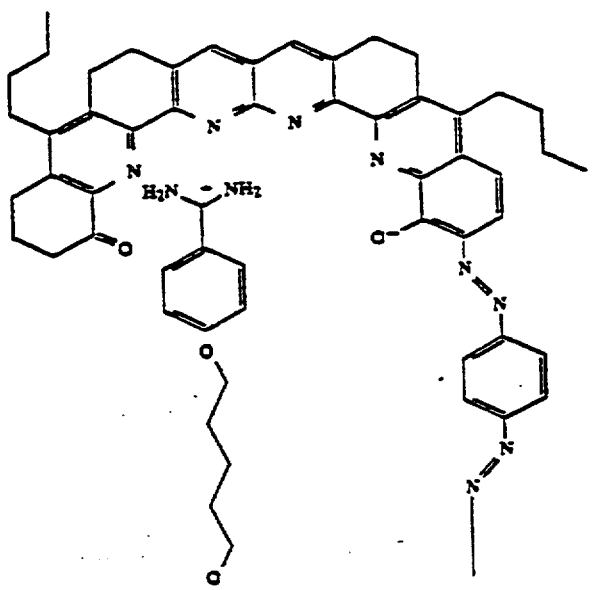

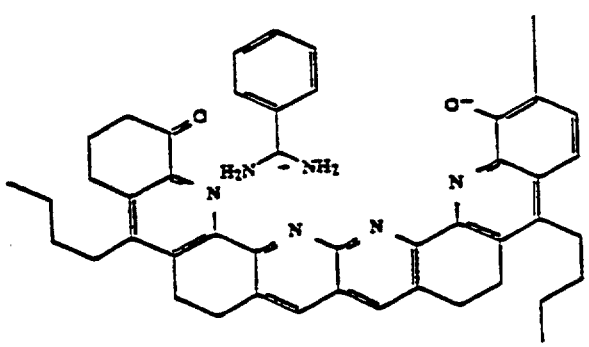

XXVa

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

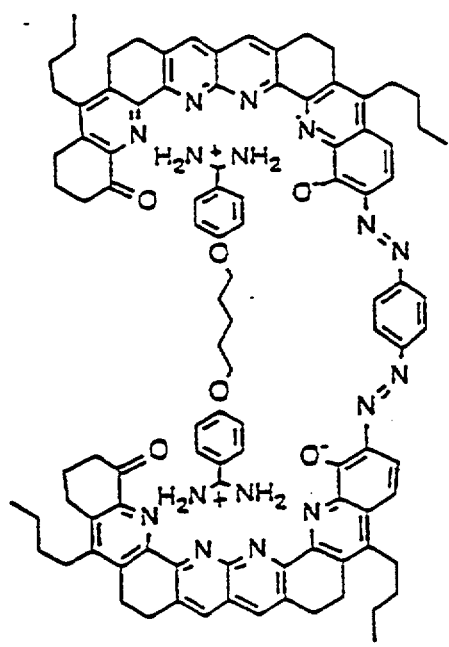

XXVa

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 39, Figure XXVIa   "

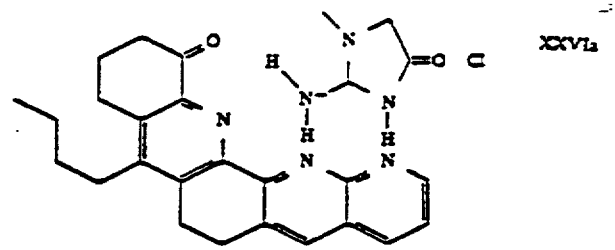

should read --

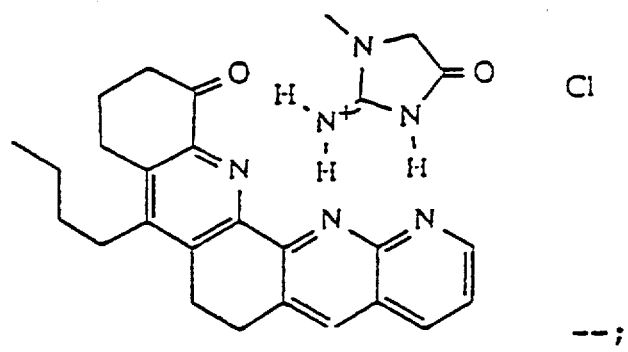

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 39, after Figure XXVIa please insert --

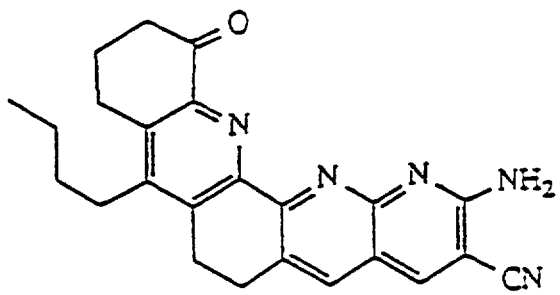

XXVII

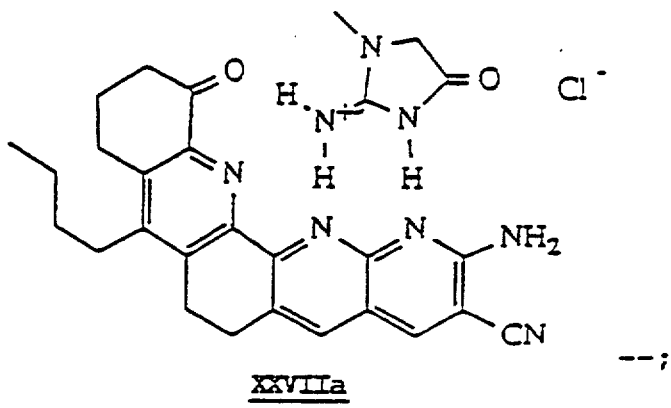

XXVIIa

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 42, Figure XXXa

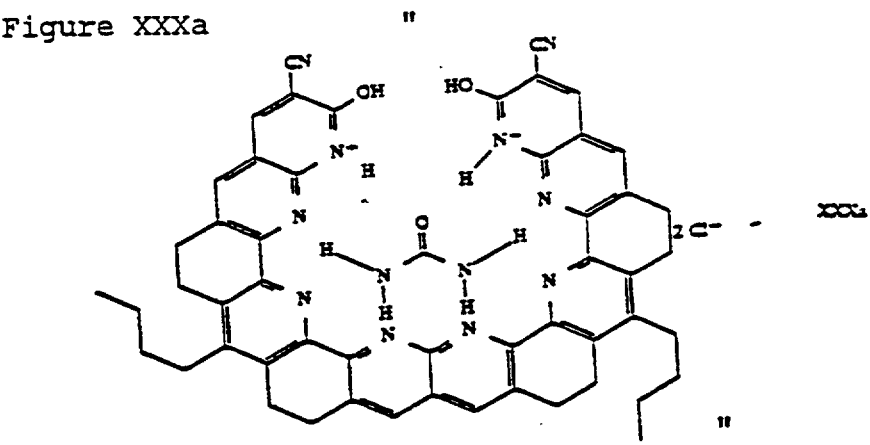

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

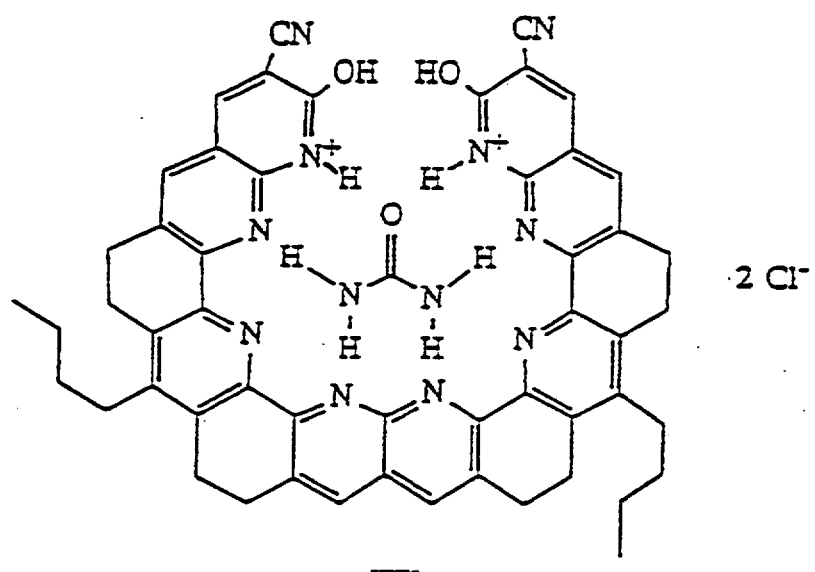

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 42, Figure XXXb         "

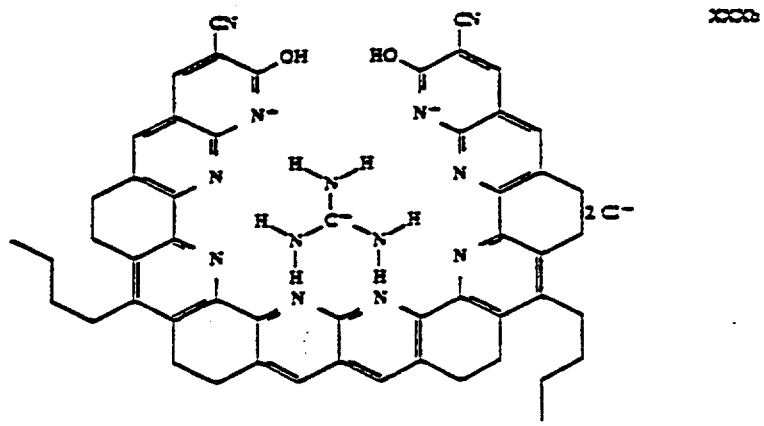

"

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

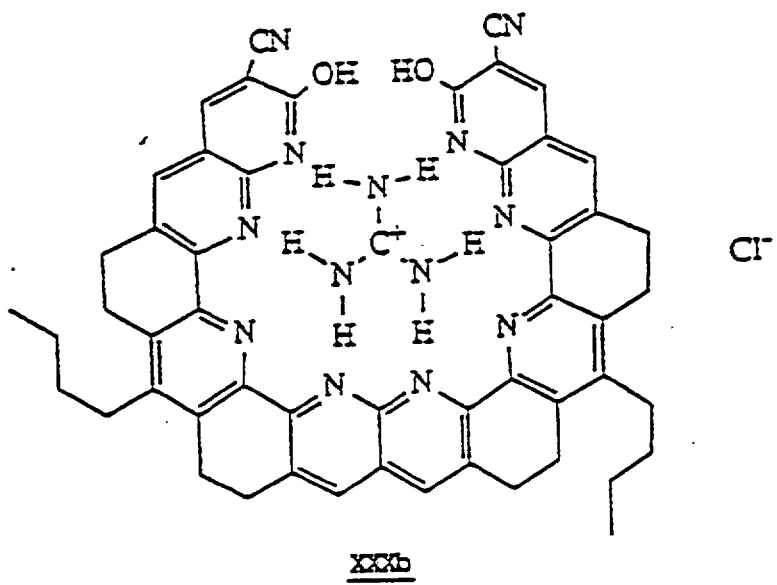

XXb

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 43, Figure XXXIa "

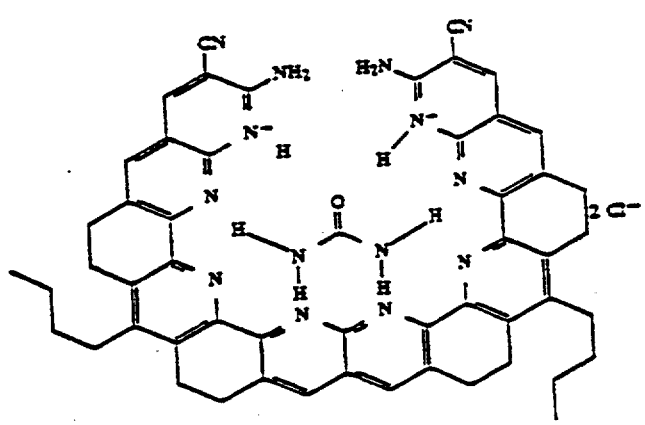

"

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

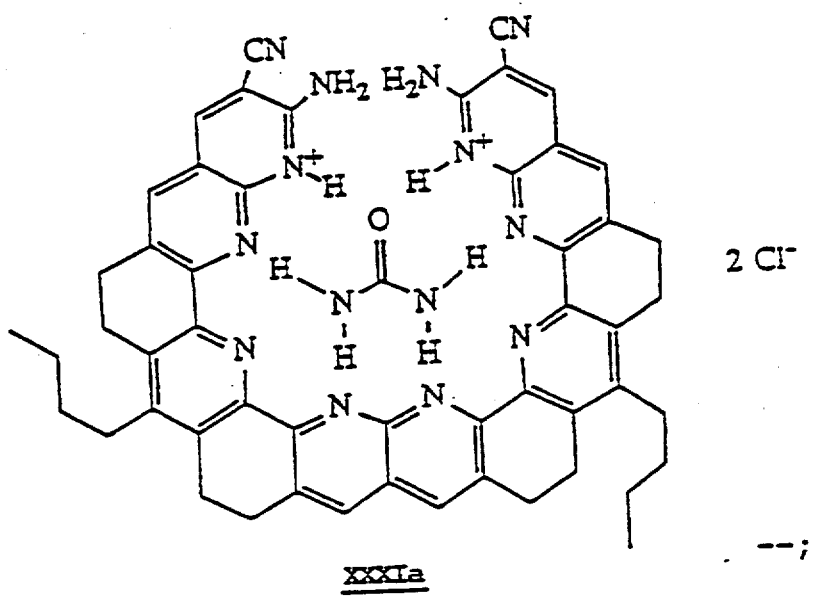

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 43, Figure XXXIb,

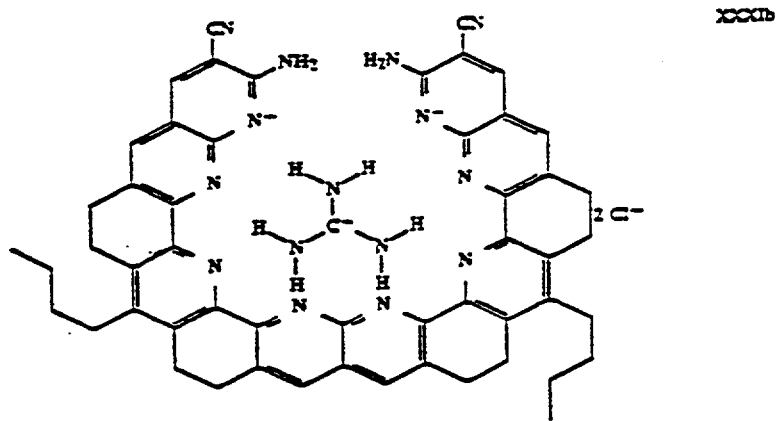

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

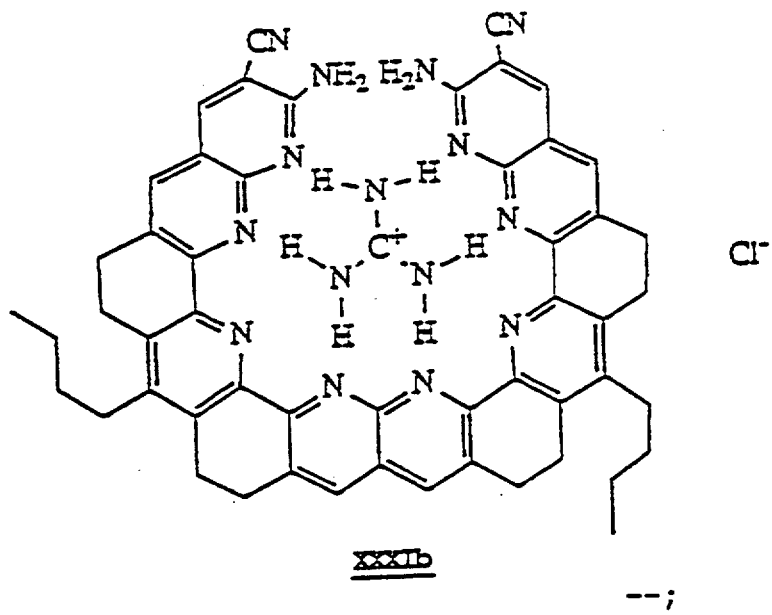

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 55 to Column 57, Reaction (5) "

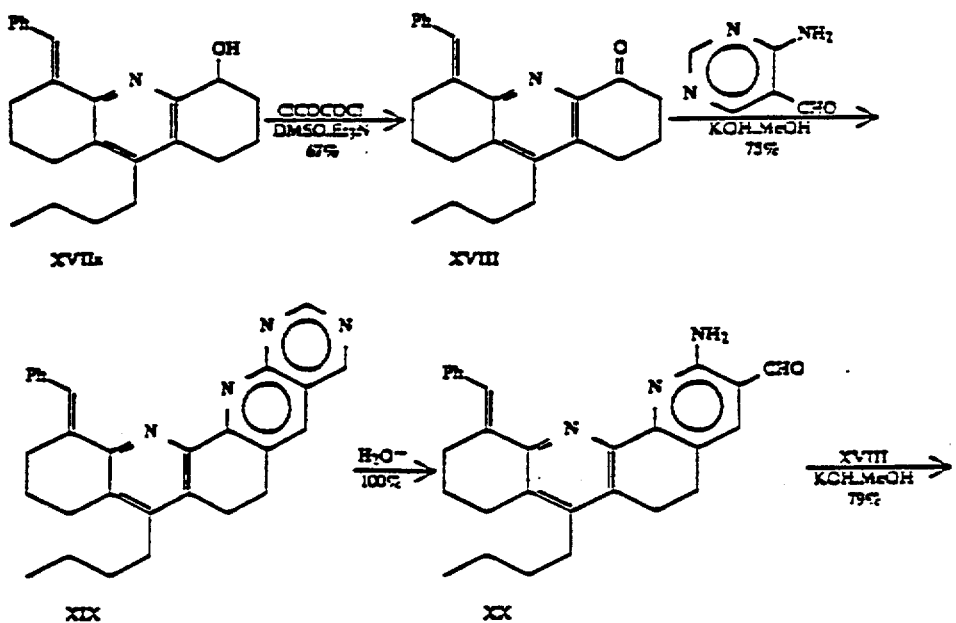

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

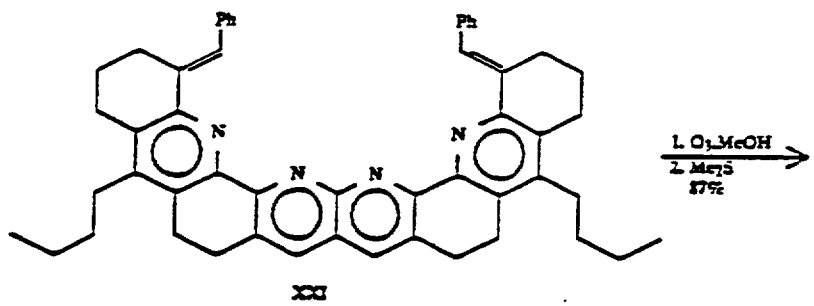

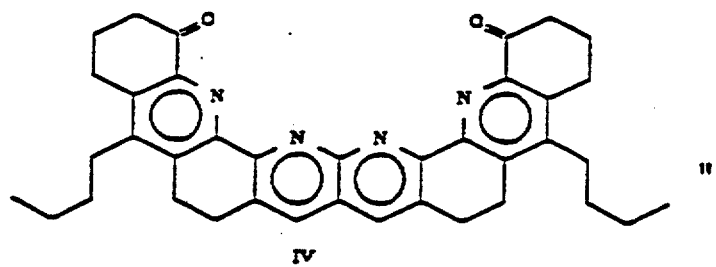

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

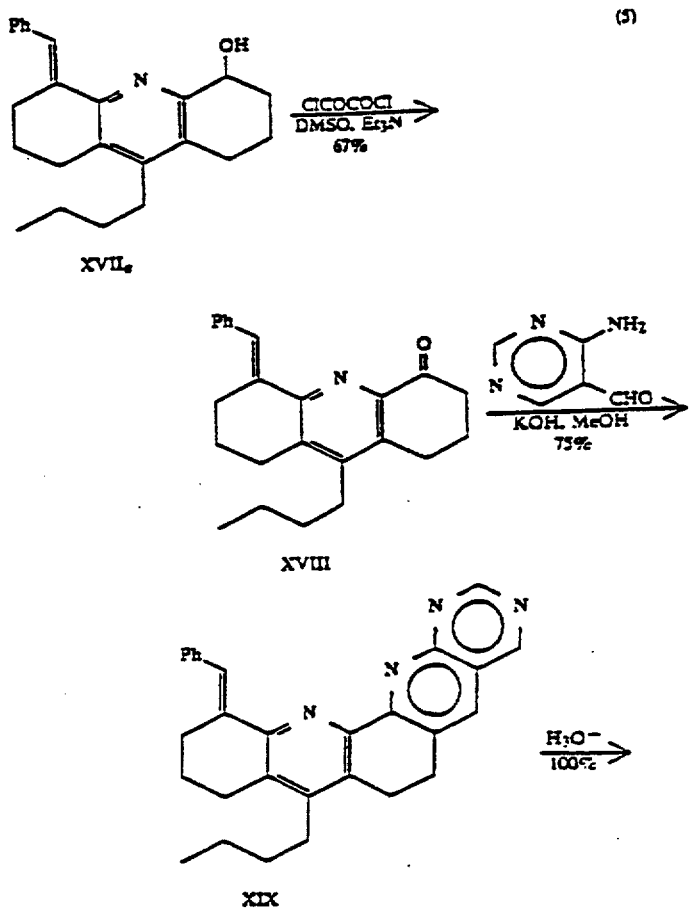

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

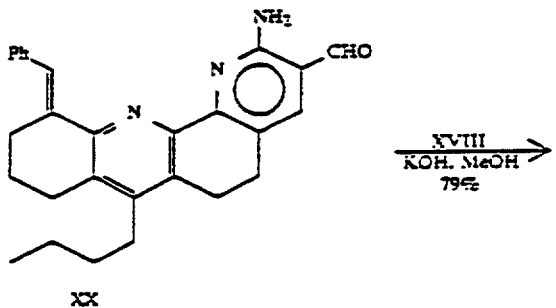

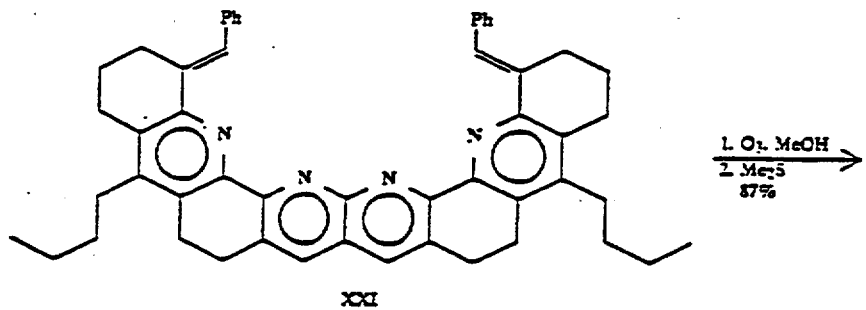

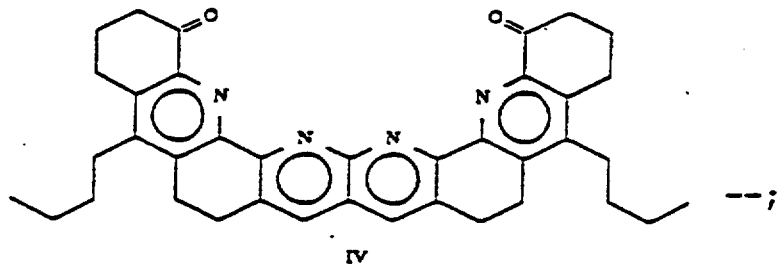

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Claim 1, structure "

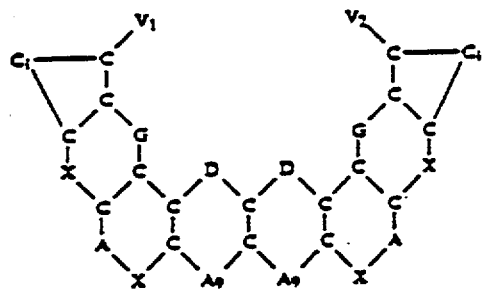

" should read --

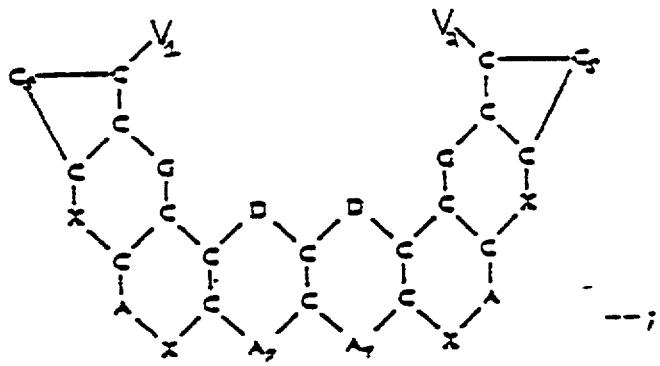

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Claim 33, structure "

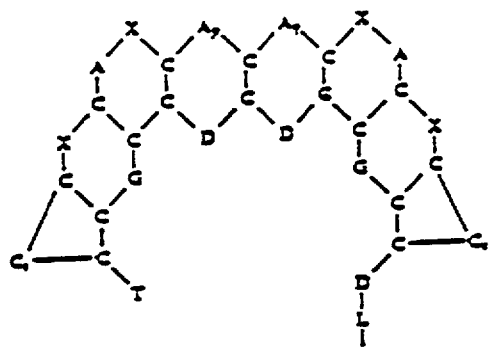

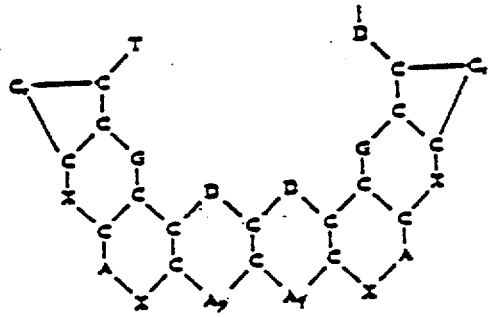

"

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

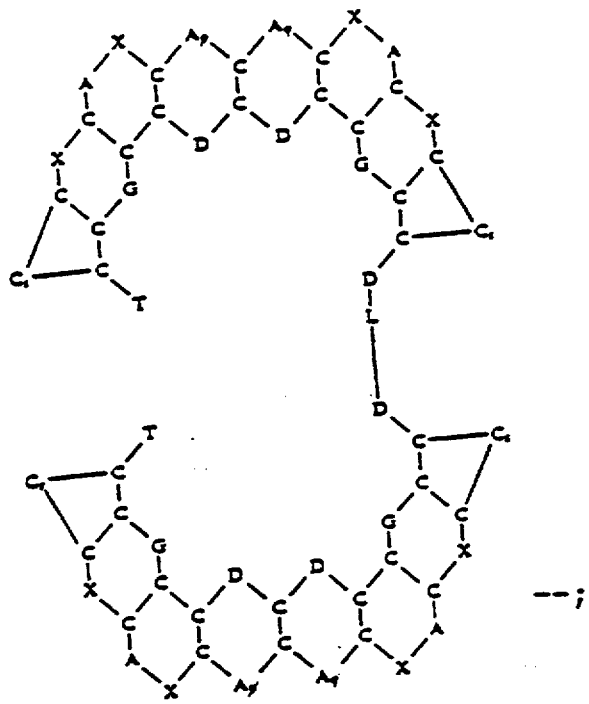

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Claim 35, structure "

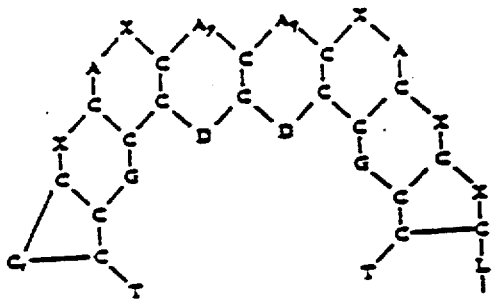

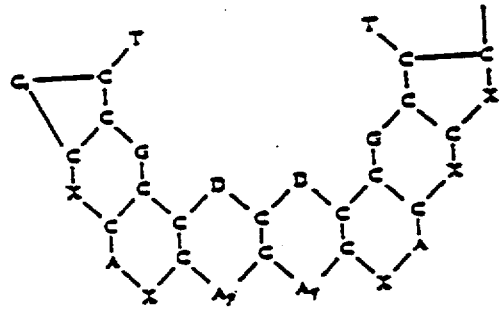

"

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

should read --

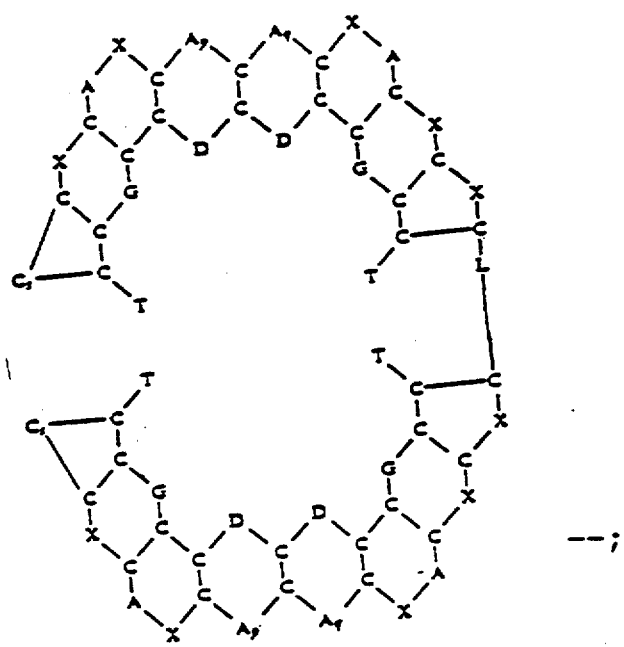

--;

UNITED STATES PATENT AND TRADEMARK OFFICE
CERTIFICATE OF CORRECTION

PATENT NO. : 5,283,333
DATED : February 1, 1994
INVENTOR(S) : Thomas W. Bell

It is certified that error appears in the above-indentified patent and that said Letters Patent is hereby corrected as shown below:

In Column 49, Line 14 — now reads "5-benzylidine-9-butyl-1,2,3,4,5,6,7,8-octahydroacridin-4-ol" should read --5-benzylidene-9-butyl-1,2,3,4,5,6,7,8-octahydroacridine-4-ol"--.

In Column 50, Line 9 — now reads "[1,10]-phenanthrolin-1,16" should read --[1,10]-phenathrolino [2,3-b] [1,10] phenanthroline -1,16--.

In Column 51, Line 60 — now reads "($CDCl_3 \delta 7.26$ ppm)" should read --($CDCl_3 \delta, 7.26$ ppm)--.

In Column 52, Line 51 — now reads "2.70 (t,4H) 1.94 (m,4H)" should read --2.70 (t,4H), 1.94 (m,4H)--.

Signed and Sealed this

Fourth Day of July, 1995

Attest:

BRUCE LEHMAN

Attesting Officer    Commissioner of Patents and Trademarks